US010688289B2

(12) United States Patent
Finson et al.

(10) Patent No.: US 10,688,289 B2
(45) Date of Patent: Jun. 23, 2020

(54) SYSTEMS AND METHODS FOR SINUS ACCESS

(71) Applicant: Intersect ENT, Inc., Menlo Park, CA (US)

(72) Inventors: Sean Finson, Santa Clara, CA (US); John Joseph Stankus, San Jose, CA (US)

(73) Assignee: Intersect ENT, Inc., Menlo Park, CA (US)

( * ) Notice: Subject to any disclaimer, the term of this patent is extended or adjusted under 35 U.S.C. 154(b) by 0 days.

(21) Appl. No.: 16/436,363

(22) Filed: Jun. 10, 2019

(65) Prior Publication Data

US 2019/0374751 A1 Dec. 12, 2019

Related U.S. Application Data

(60) Provisional application No. 62/684,011, filed on Jun. 12, 2018.

(51) Int. Cl.
*A61B 1/07* (2006.01)
*A61K 31/58* (2006.01)
(Continued)

(52) U.S. Cl.
CPC ......... *A61M 25/10182* (2013.11); *A61B 1/07* (2013.01); *A61K 31/58* (2013.01);
(Continued)

(58) Field of Classification Search
CPC ...... A61M 25/10182; A61M 25/09041; A61M 25/1018; A61M 25/10187;
(Continued)

(56) References Cited

U.S. PATENT DOCUMENTS 5,209,732 A * 5/1993 Lampropoulos ...... A61M 5/315
604/224
5,562,619 A * 10/1996 Mirarchi ............. A61B 17/221
604/264
(Continued)

FOREIGN PATENT DOCUMENTS

JP 2008-099917 A 5/2008
WO WO-2006/107957 A2 10/2006
(Continued)

OTHER PUBLICATIONS

Extended European Search Report dated Dec. 5, 2018, for EP Application No. 16 740 876.4, filed on Jan. 22, 2016, 9 pages.
(Continued)

*Primary Examiner* — Pedro Philogene
(74) *Attorney, Agent, or Firm* — Cooley LLP

(57) ABSTRACT

This application is generally related to systems and methods for accessing the paranasal sinuses and other passages of the nose, ear, and throat. The systems and methods generally employ devices capable of maintaining a fixed handle orientation with respect to the patient while generating the appropriate applicator deflection angle required to rotationally align or orient the applicator tip to the intended target tissue/anatomy for treatment. Methods are also described for deploying drug delivery devices within these body structures using the systems to treat medical conditions associated therewith.

28 Claims, 28 Drawing Sheets

(51) Int. Cl.
*A61M 25/09* (2006.01)
*A61M 25/10* (2013.01)
*A61M 29/02* (2006.01)

(52) U.S. Cl.
CPC ...... *A61M 25/09041* (2013.01); *A61M 29/02* (2013.01); *A61M 2025/105* (2013.01); *A61M 2029/025* (2013.01); *A61M 2210/0681* (2013.01)

(58) Field of Classification Search
CPC ...... A61M 25/10185; A61M 25/10181; A61M 25/0058; A61M 25/09; A61M 25/10186; A61M 29/02; A61M 2025/105; A61M 2025/09116; A61M 2029/025; A61M 2210/0615; A61M 39/22; A61M 39/12; A61M 2039/1033; A61B 1/07; A61B 17/24; A61B 2017/00331; A61B 2017/00535; A61K 31/58; A61F 2/002
USPC ........ 600/249, 178, 104, 137; 606/193, 167, 606/170, 191, 2, 3
See application file for complete search history.

(56) References Cited

U.S. PATENT DOCUMENTS

| | | |
|---|---|---|
| 6,329,386 B1 | 12/2001 | Mollison |
| 6,533,772 B1 | 3/2003 | Sherts et al. |
| 7,105,013 B2 | 9/2006 | Durcan |
| 7,559,925 B2 | 7/2009 | Goldfarb et al. |
| 7,717,933 B2 | 5/2010 | Becker |
| 7,740,642 B2 | 6/2010 | Becker |
| 7,753,929 B2 | 7/2010 | Becker |
| 8,100,933 B2 | 1/2012 | Becker |
| 8,142,422 B2 | 3/2012 | Makower et al. |
| 8,414,473 B2 | 4/2013 | Jenkins et al. |
| 8,905,922 B2 | 12/2014 | Makower et al. |
| 9,138,569 B2 | 9/2015 | Edgren et al. |
| 9,381,328 B2 | 7/2016 | Xie et al. |
| 9,554,817 B2* | 1/2017 | Goldfarb ................ A61B 17/24 |
| 9,603,506 B2 | 3/2017 | Goldfarb et al. |
| 10,166,369 B2* | 1/2019 | Jenkins ................... A61B 1/07 |
| 10,441,757 B2 | 10/2019 | Kaufman et al. |
| 2002/0082584 A1* | 6/2002 | Rosenman ........ A61M 25/0014 604/523 |
| 2007/0250105 A1 | 10/2007 | Ressemann et al. |
| 2008/0065011 A1 | 3/2008 | Marchand et al. |
| 2009/0163890 A1 | 6/2009 | Clifford et al. |
| 2010/0198190 A1 | 8/2010 | Michal et al. |
| 2010/0211007 A1* | 8/2010 | Lesch, Jr. ............. A61M 29/02 604/97.02 |
| 2010/0272773 A1 | 10/2010 | Kangas et al. |
| 2011/0144577 A1 | 6/2011 | Stankus et al. |
| 2012/0143132 A1 | 6/2012 | Orlowski |
| 2012/0150142 A1 | 6/2012 | Weber et al. |
| 2013/0053947 A1 | 2/2013 | Kangas et al. |
| 2013/0066358 A1 | 3/2013 | Nalluri et al. |
| 2013/0142834 A1 | 6/2013 | Esfand et al. |
| 2014/0046255 A1 | 2/2014 | Hakimimehr et al. |
| 2014/0073911 A1 | 3/2014 | Munrow et al. |
| 2014/0074140 A1* | 3/2014 | Johnson .......... A61M 25/10182 606/192 |
| 2014/0100445 A1 | 4/2014 | Stenzel et al. |
| 2014/0200443 A1* | 7/2014 | Chang ................ A61B 17/1204 600/424 |
| 2015/0065810 A1 | 3/2015 | Edgren et al. |
| 2015/0112134 A1 | 4/2015 | Suehara et al. |
| 2015/0142046 A1 | 5/2015 | Andersen et al. |
| 2015/0273117 A1 | 10/2015 | Wang |
| 2016/0045718 A1 | 2/2016 | Pruitt et al. |
| 2016/0121088 A1 | 5/2016 | Fox et al. |
| 2016/0213890 A1 | 7/2016 | Kaufman et al. |
| 2017/0165064 A1 | 6/2017 | Nyuli et al. |
| 2019/0160266 A1 | 5/2019 | Ngo-Chu et al. |

FOREIGN PATENT DOCUMENTS

| | | |
|---|---|---|
| WO | WO-2006/107957 A3 | 10/2006 |
| WO | WO-2010/126912 A1 | 11/2010 |
| WO | WO-2010/132648 A1 | 11/2010 |
| WO | WO-2013/130464 A1 | 9/2013 |
| WO | WO-2014/066085 A1 | 5/2014 |
| WO | WO-2014/075513 A1 | 5/2014 |

OTHER PUBLICATIONS

Final Office Action dated Apr. 11, 2019, for U.S. Appl. No. 15/004,807, filed Jan. 22, 2016, 12 pages.
International Search Report dated Mar. 31, 2016, for PCT Application No. PCT/US2016/014622, filed Jan. 22, 2016, 2 pages.
Non-Final Office Action dated Dec. 31, 2018, for U.S. Appl. No. 15/004,807, filed Jan. 22, 2016, 10 pages.
St. Croix, B. et al. (2000). "Genes expressed in human tumor endothelium," *Science* 289:1197-1202.
Written Opinion of the International Searching Authority dated Mar. 31, 2016, for PCT Application No. PCT/US2016/014622, filed Jan. 22, 2016, 7 pages.
International Search Report dated Aug. 28, 2019, for PCT Application No. PCT/US2019/036506, filed Jun. 11, 2019, 3 pages.
Notice of Allowance dated Jul. 17, 2019, for U.S. Appl. No. 15/004,807, filed Jan. 22, 2016, 7 pages.
Notice of Allowance dated Aug. 13, 2019, for U.S. Appl. No. 15/004,807, filed Jan. 22, 2016, 6 pages.
Notice of Allowance dated Nov. 22, 2019, for U.S. Appl. No. 16/523,836, filed Jul. 26, 2019, 7 pages.
Written Opinion of the International Searching Authority dated Aug. 28, 2019, for PCT Application No. PCT/US2019/036506, filed Jun. 11, 2019, 12 pages.

\* cited by examiner

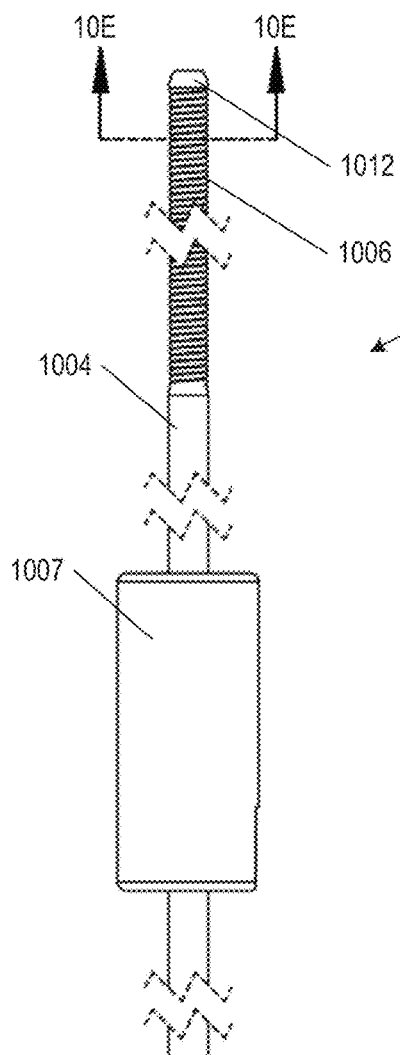
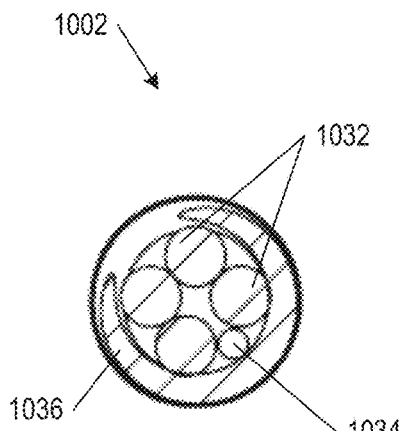
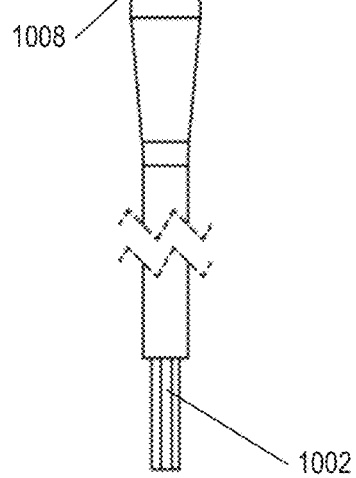
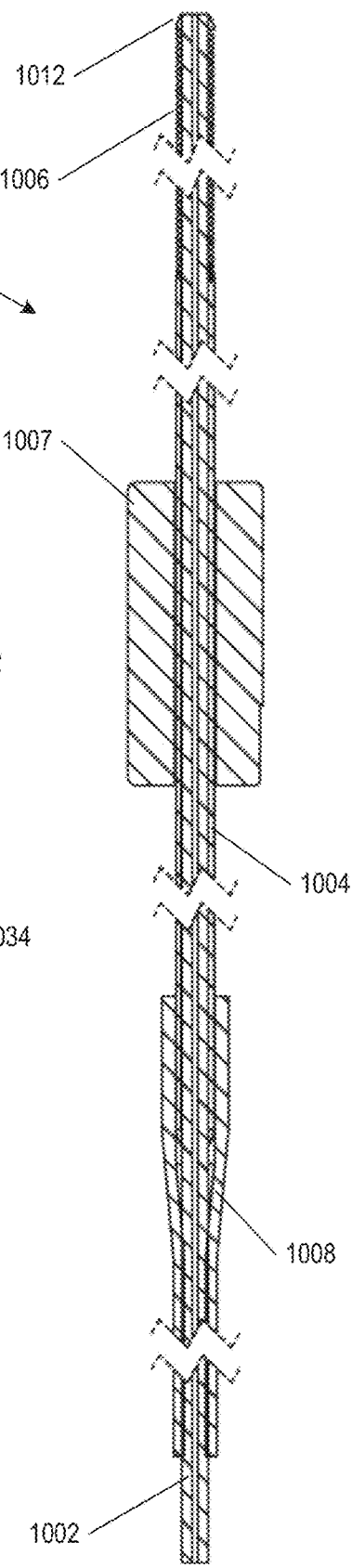
FIG. 10E
FIG. 10A
FIG. 10B

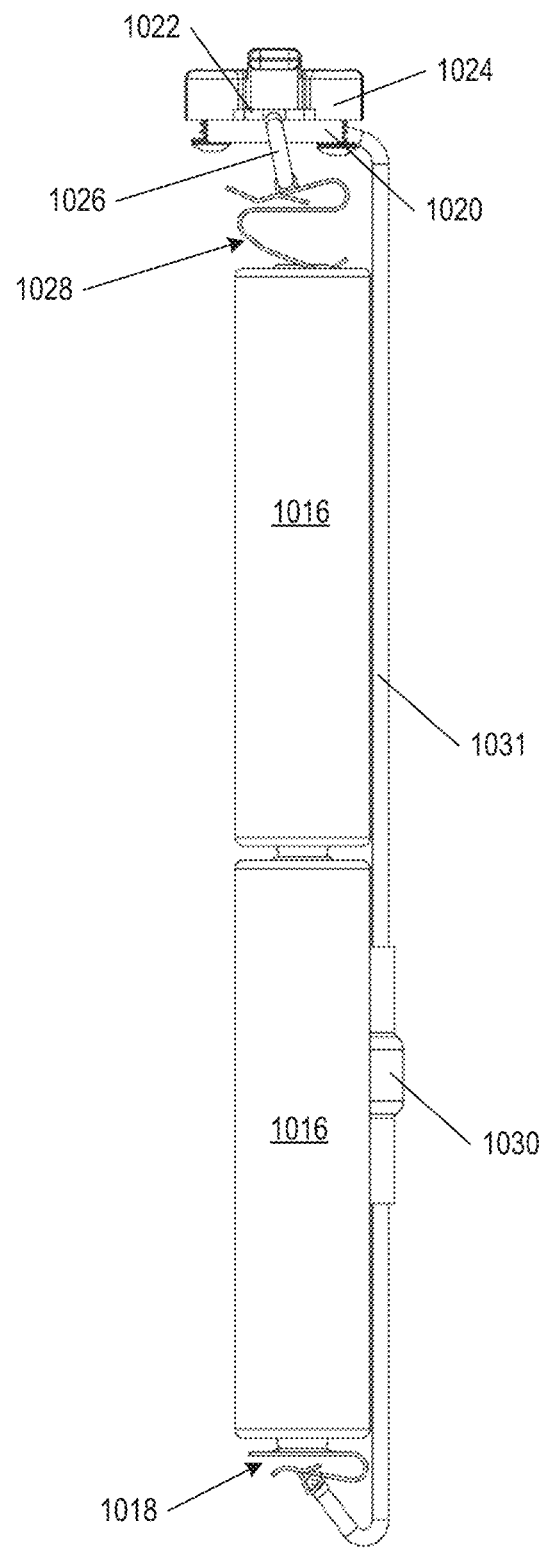
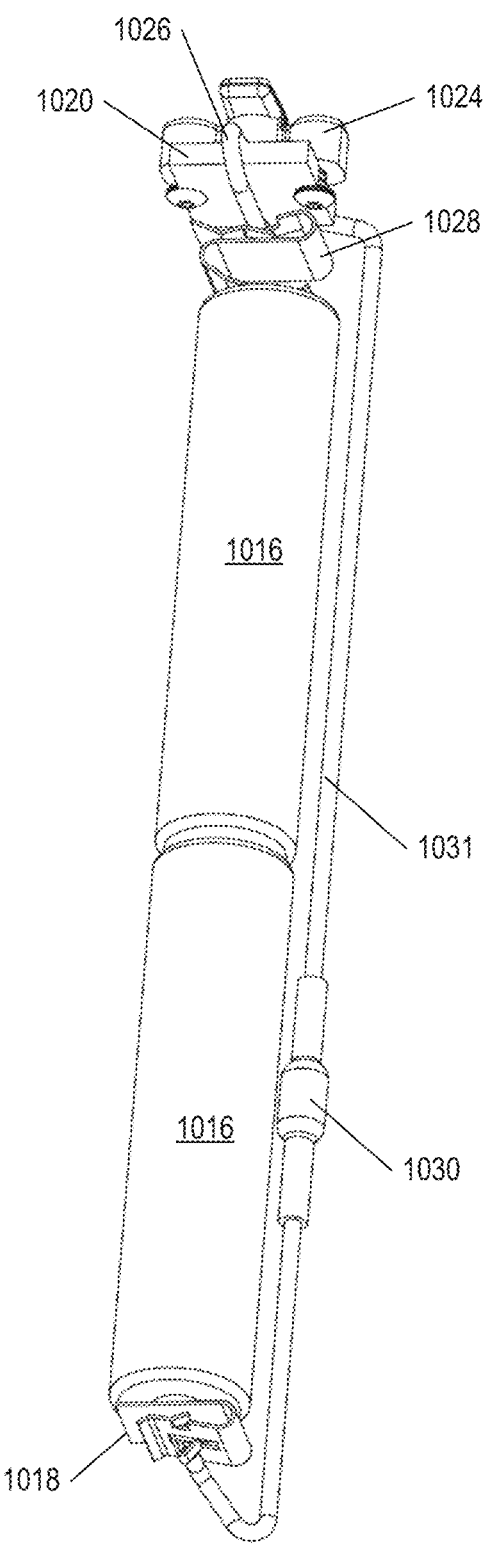
FIG. 10C
FIG. 10D

SYSTEMS AND METHODS FOR SINUS ACCESS

CROSS-REFERENCE TO RELATED APPLICATION

This application claims the benefit of priority from U.S. provisional application No. 62/684,011, titled "SYSTEMS AND METHODS FOR SINUS ACCESS" and filed on Jun. 12, 2018, which is hereby incorporated by reference in its entirety.

FIELD

This application is generally related to systems and methods for accessing the paranasal sinuses and other passages of the nose, ear, and throat. Methods are also described for deploying devices within these body structures, for example, expandable and/or drug delivery devices, using the systems to treat medical conditions associated therewith.

BACKGROUND

Rhinosinusitis is a common paranasal sinus condition that is generally understood as encompassing sinusitis and/or rhinitis. Typically, rhinosinusitis is characterized by major symptoms such as nasal discharge, nasal obstruction, facial congestion, facial pain/pressure, loss of smell, and fever, and minor symptoms such as headache, ear pain/pressure, halitosis, dental pain, cough, and fatigue.

Allergic rhinitis is associated with a group of symptoms affecting the nose that occurs when an individual with the condition breaths in an allergen, such as dust, mold, or animal dander. Allergens cause the release of histamine, which usually causes sneezing, itchy and watery eyes, runny nose, swelling and inflammation of the nasal passages, an increase in mucus production, and for some individuals, hives or other rashes. Allergic rhinitis due to pollen is commonly known as hay fever.

Current treatments for these and other nasal conditions, as well as certain otic and throat conditions, are primarily pharmaceutical. Drugs in pill form are widely available and easy to take, but can have several drawbacks. An orally administered drug may require considerable time to work through the body to become effective, and may have negative side effects that can impact the daily life of the patient. Also, the drug may need to be taken frequently for continued symptom relief. Nasal, otic, and throat topical drug delivery represents an attractive alternative approach for the treatment of local nasal, otic, and throat diseases. However, current technologies for local drug delivery of drugs in either liquid or powder form, and by spray or direct application, can be limited by poor patient compliance when repeated doses are required, or poor efficacy due to challenges in delivering a drug to more distal sinus and ear anatomies.

When sinusitis is recurrent, functional endoscopic surgery (FESS) can also be used to surgically open a natural ostium of a paranasal sinus in order to improve drainage from the sinus cavity. More recently, minimally invasive systems have been developed that enable the performance of FESS procedures and other ENT surgeries. In some of these minimally invasive systems, a balloon catheter is employed to dilate and/or deliver a therapeutic agent to the paranasal sinuses. Although the minimally invasive systems have led to advancements in sinusitis treatment, their further refinement would be useful. For example, minimally invasive systems with improved ergonomics and reduced profiles, and which integrate multiple system components into a single hand-held device would be useful. Additionally, minimally invasive systems capable of treating multiple paranasal sinuses with a single balloon catheter may be useful. It may also be beneficial to have minimally invasive systems capable of minimizing loss of the therapeutic agent from the balloon during balloon deployment.

SUMMARY

Described herein are systems and methods for accessing the paranasal sinuses and other passages of the nose, ear, and throat, and for treating medical conditions associated with them. Instead of using various removable, interchangeable, or swappable applicators having different deflection angles when accessing different anatomical regions, the systems and methods generally include an integrated applicator that is fixedly attached to a handle and capable of adjustable/selective deflection so that multiple target tissue sites may be accessed using the same applicator. In some instances, the systems are configured to deploy balloon catheters, where the balloons are used to dilate a sinus ostium or passageway and/or deliver drug to a target tissue when expanded. Examples of such balloon catheters are described in commonly owned U.S. patent application Ser. No. 15/004,807, entitled "DRUG-COATED BALLOON," which is herein incorporated by reference. It is understood that the terms "drug" and "therapeutic agent" are used interchangeably throughout.

The systems and methods may be useful when drug delivery to multiple target tissue sites is desired using a single device, and/or when dilation or separation of target tissues is desired with a single device given that exchanging a device for each target tissue may be time consuming and costly. For example, the design may be useful when a single drug-coated balloon is used to deliver drug to multiple paranasal sinuses. In order to access the various paranasal sinuses, system angles of 0 degrees to about 120 degrees typically need to be achieved. The systems and methods described herein are capable of maintaining a fixed handle orientation with respect to the patient while generating the appropriate angle required to rotationally align or orient an applicator tip to the intended sinus or target tissue/anatomy for treatment. Deflection of the applicator may be achieved using a single pullwire instead of the multiple pullwires typically included with commercially available steerable catheters. Use of a single pullwire may simplify manufacturing and generally decreases the applicator diameter, allowing for improved steering through inflamed or stenotic tissue passageways, as well improved ergonomics when handling with an endoscope. The catheter tip may need to be deflected about 70 degrees (with respect to the longitudinal axis of the catheter) when accessing the frontal sinus or about 110 degrees when accessing the maxillary sinus. Deflection may not be needed (deflection of zero degrees) when attempting to access the sphenoid sinus. In some instances, accessing specific sinuses may be more difficult than average due to uncommon anatomy or particularly challenging obstructions and blockages. In such cases, the catheter tip may be deflected to an angle not normally associated with the respective sinus (e.g., deflecting the catheter tip to 110 degrees in order to access the frontal sinus) where the selected angle is more conducive for accessing that sinus.

The systems for accessing a target tissue site associated with a paranasal sinus described herein generally include an applicator, where the applicator comprises a proximal end, a deflectable distal end, a distal tip, a device lumen, and a pullwire lumen. A handle is typically coupled to the applicator, the handle comprising an elongate slot having a travel length, and a finger slide coupled to a guidewire and movable along the travel length to advance the guidewire through the applicator. Additionally, a single pullwire may be attached to the applicator distal tip and extend proximally through the pullwire lumen. An adjustment knob may be coupled to the applicator. The adjustment knob may be configured such that its rotation bends the deflectable distal end of the applicator to a deflection angle that provides access to the target tissue site. The deflection angle may range from about 0 degrees to about 120 degrees with respect to the longitudinal axis of the applicator. Instead of an adjustment knob, other components, for example, a slide, trigger, dial, button, etc., may be used to generate the desired deflection angle. A system employing a single pullwire to achieve multiple deflection angles while maintaining a fixed handle orientation with respect to the patient simplifies the manufacturing process and the system overall, and may also decrease the applicator diameter, allowing for improved steering through inflamed or stenotic tissue passageways, as previously stated. The systems described herein may further be used for accessing other target tissue sites within the nose, as well as target tissue sites within the ear and throat.

In some variations, the adjustment knob includes a locking mechanism. The locking mechanism may hold the adjustment knob at a rotational position to maintain a set deflection angle. Alternatively, the locking mechanism may lock the pullwire to maintain the desired deflection angle.

Methods for accessing a target tissue site associated with a paranasal sinus are further described herein. The methods may generally include holding a system in a fixed orientation with respect to the patient, where the system includes an applicator comprising a proximal end, a deflectable distal end, a device lumen, and a pullwire lumen; a handle coupled to the applicator, where the handle having an elongate slot having a travel length and a finger slide coupled to a guidewire; a single pullwire attached to the applicator distal tip and extending proximally through the pullwire lumen; and an adjustment knob coupled to one of the applicator or the pullwire. For some methods, the applicator may be advanced to a position near the target tissue site and the adjustment knob rotated to retract the pullwire proximally and deflect the distal end of the applicator to a deflection angle. For other methods, the adjustment knob may be rotated to retract the pullwire proximally to deflect the distal end of the applicator to a deflection angle and then the applicator may be advanced to a position near the target tissue site. A guidewire may then be advanced through the applicator by advancing the finger slide along at least a portion of the travel length of the elongate slot. Various devices may be deployed over the guidewire to dilate and/or deliver drug to target tissue sites of the nose, for example, the paranasal sinuses, as well as target tissue sites of the ear and throat. In some instances, the devices are drug-coated balloons. In other instances, the devices may be stents or other implantable structures useful in maintaining patency of the target tissue site instead of dilating the site.

Methods for deploying the same balloon catheter multiple times to the same target tissue site or to different target tissue sites are also described herein. For example, an applicator of the system may be advanced to a target tissue site of a paranasal sinus (e.g., a paranasal sinus ostium or a paranasal sinus recess), and the distal end of the applicator adjusted to the desired deflection angle by rotating an adjustment knob of the system. A balloon catheter may then be advanced from the applicator to the target tissue site and the balloon expanded to contact the target tissue site. The balloon may be expanded to an expanded configuration to deliver a drug coating to the tissue and/or for tissue dilation. Thereafter, the balloon may be deflated to a collapsed configuration and withdrawn into the applicator. If the same balloon is to be used again, either in the same or in a different ostium, the deflection angle of the applicator distal end may be adjusted/changed by rotating the adjustment knob and then the balloon advanced from the applicator and re-expanded. When the balloon is to be re-expanded in the same ostium, the deflection angle may not need to be adjusted. The balloon may then be collapsed and withdrawn again back into the applicator. Readjustment of the deflection angle and deployment of the balloon catheter may be repeated any number of times.

When a drug coating is delivered, the applicator may include features that help minimize loss of the drug coating (and in turn loss of drug) during deployment (e.g., advancement from the applicator and/or withdrawal back into the applicator). These drug protective features may include the use of lubricious materials to form the applicator or provide a layer therein, or various applicator configurations that reduce scraping of the balloon against the applicator distal end.

BRIEF DESCRIPTION OF THE DRAWINGS

FIG. 2A shows a perspective view of the system; FIG. 2B is a cross-sectional view of the applicator shown in FIG. 2A; and FIG. 2C shows a perspective view of the system of FIG. 2A in use with a dilator.

FIG. 2D shows a perspective view of the system, and FIG. 2E shows a perspective view of the system of FIG. 2D in use with a dilator FIG. 3A is a perspective view of an exemplary system; FIG. 3B shows an exemplary first flange of the system of FIG. 3A with the adjustment knob and handle removed, and where the first flange is coupled to the housing of the handle; FIGS. 3C-3H show further details of the deflection mechanism used to bend the applicator of the system; and FIGS. 3I-3K illustrate the correlation between adjustment knob rotation and deflection of the applicator of the system.

FIGS. 10A-10E depict components of a lighted guidewire according to one variation.

DETAILED DESCRIPTION

Described herein are systems and methods for accessing the paranasal sinuses and other passages of the nose, ear, and throat, and for treating medical conditions associated with them. The systems generally include an applicator capable of adjustable/selective deflection so that multiple target tissue sites may be accessed using the same applicator, and a handle coupled to the applicator. The systems may be configured such that when the handle is held in a fixed orientation with respect to the patient, the appropriate deflection angle required to rotationally align or orient the applicator tip to the intended target tissue/anatomy for treatment is generated. Multiple deflection angles may be generated while the handle is held in the aforementioned fixed orientation, and may generally range between about 0 degrees to about 120 degrees from the longitudinal axis of the applicator. Deflection of the applicator tip may be achieved using a single pullwire, which simplifies the system and also decreases the applicator diameter, allowing for improved steering through inflamed or stenotic tissue passageways.

The systems and methods may be useful for delivering various devices to target tissue sites, e.g., a nasal passages or paranasal sinuses, depending on the medical condition to be treated. The devices may be expandable or non-expandable. The devices may be configured to dilate tissues or deliver a drug. In some variations, the devices are drug-coated balloons that may dilate and/or deliver a drug to one or more paranasal sinuses or one or more paranasal sinus ostia.

The devices may be tailored to treat various medical conditions including, but not limited to, post-surgical inflammation, rhinosinusitis, chronic sinusitis with or without nasal polyps, and rhinitis, including allergic rhinitis. In the aforementioned variations, the target tissue site may be a paranasal sinus, a sinus ostium, a paranasal sinus recess, an inferior turbinate, a middle turbinate, a superior turbinate, a nasal cavity, the osteomeatal complex, the nasopharynx, adenoid tissue, or a combination thereof. In these variations, the deflection angle (hereafter also referred to as "applicator deflection angle") may range from zero degrees to about 120 degrees from the longitudinal axis of the applicator. For example, the deflection angle may be zero degrees, about 10 degrees, about 20 degrees, about 30 degrees, about 40 degrees, about 50 degrees, about 60 degrees, about 70 degrees, about 80 degrees, about 90 degrees, about 100 degrees, about 110 degrees, or about 120 degrees from the longitudinal axis of the applicator. Further, the deflection angle may be any increment or gradient of angle within the range of from zero degrees to 120 degrees. In some variations, the deflection angle may be greater than 120 degrees.

Figure 1:
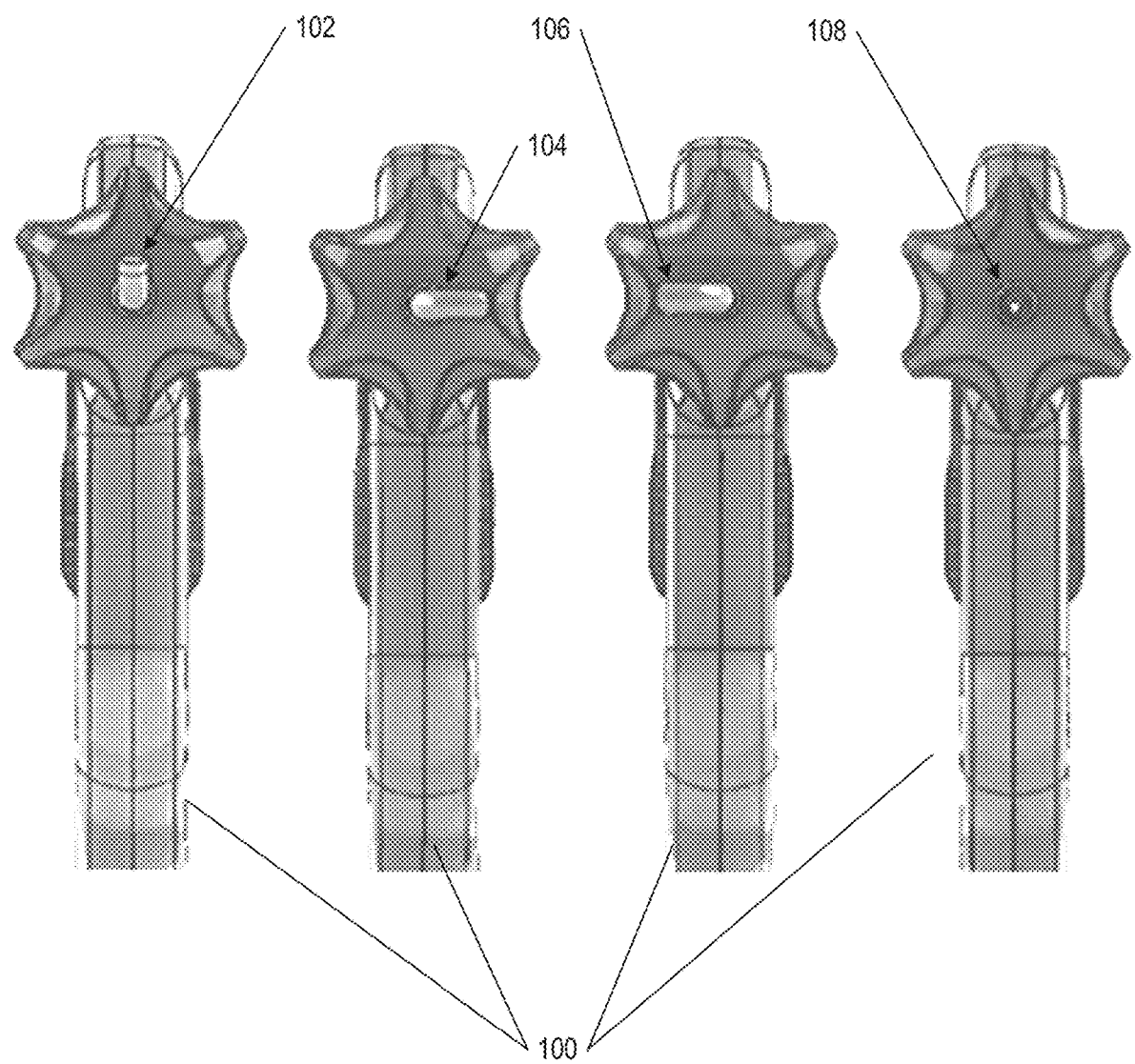
FIG. 1 depicts exemplary deflection angles of the applicator distal tip used to access the paranasal sinuses.

FIG. 1 shows exemplary deflection angles generated by the systems and methods described herein in order to access different paranasal sinuses. Given the handle orientation shown (handle (100)), an applicator tip having a 70 degree deflection with respect to the longitudinal axis of the applicator is shown pointing up (at the 12 o'clock position (102)), which can allow for access to both left and right frontal sinuses. Access to the right maxillary sinus can be provided by an applicator tip having a 110 degree deflection with respect to the longitudinal axis thereof, pointed to the right (at the 3 o'clock position (104)). Access to the left maxillary sinus can be provided by an applicator tip having a 110 degree deflection with respect to the longitudinal axis thereof, pointed to the left (at the 9 o'clock position (106)). Lastly, access to both sphenoid sinuses can be provided where the applicator tip would remain straight, with zero degrees of deflection (108).

When the device includes a drug or a drug within a coating thereof to treat a medical condition associated with the nose or a paranasal sinus, the drug may comprise an anti-inflammatory agent, an anti-infective agent, an antihistamine, a decongestant, a mucolytic agent, or combinations or mixtures thereof. In some variations, the anti-inflammatory agent is a corticosteroid. An exemplary corticosteroid is mometasone furoate, or a pharmaceutically acceptable salt, solvate, hydrate, ester, free base, enantiomer, racemate, polymorph, amorphous, or crystal form thereof. In some variations, the corticosteroid is fluticasone, or a pharmaceutically acceptable salt, solvate, hydrate, ester, free base, enantiomer, racemate, polymorph, amorphous, or crystal form thereof.

In other variations, the condition to be treated may be an otic condition selected from the group consisting of post-surgical inflammation, otitis media, Meniere's disease, Eustachian tube dysfunction, and tinnitus. In such variations, the target tissue site may be the Eustachian tube, external ear canal, or inner ear. The deflection angle useful to employ with these target tissue sites may range from zero degrees to about 120 degrees, or from about 45 degrees to about 90 degrees from the longitudinal axis of the applicator. Treatment of the Eustachian tube may also be beneficial in treating hearing loss, otalgia, and vertigo. When the device includes a drug or a drug within a coating thereof to treat an otic condition, it may be useful for the drug to include an anti-inflammatory agent, an anti-infective agent, or combinations or mixtures thereof.

In yet further variations, the condition to be treated may be a throat condition selected from the group consisting of post-surgical pain, esophageal cancer, airway stenosis, e.g., tracheal stenosis, laryngeal stenosis, or subglottic stenosis, chronic laryngitis, tonsillitis, and epiglottitis. In such variations, the target tissue site may be adenoid tissue or tonsillar tissue. When treating a throat condition, it may be useful to employ a deflection angle ranging from zero degrees to about 120 degrees, or from about 45 degrees to about 90 degrees from the longitudinal axis of the applicator. When the device includes a drug or a drug within a coating thereof to treat a throat condition, it may be useful for the drug to include a painkiller, an anti-infective agent, a chemotherapeutic agent, or combinations or mixtures thereof.

When a drug or drug coating is to be delivered from a device, the systems may also include features that minimize drug loss during deployment and/or repeated deployment of the device. These drug protective features may include the use of lubricious materials or employ modified applicator distal ends that minimize scraping of the device as it exits the applicator and/or is retracted back into the applicator.

Systems

The systems described herein generally include an applicator having a steerable or deflectable distal end, a handle coupled to a proximal end of the applicator, and an adjustment knob that rotates with respect to the handle to align or orient the applicator distal tip to a target tissue site. In general, while the handle is maintained in a fixed position, rotation of the adjustment knob pulls a pullwire, which in turn deflects the distal end of the applicator depending on the amount of adjustment knob rotation. This design may be useful when drug delivery to multiple target tissue sites is desired using a single device or when the same device is used to delivery drug to the same target tissue site multiple times. For example, the design may be useful when a single drug-coated balloon is used to deliver a drug to multiple paranasal sinuses. Instead of an adjustment knob, a slide, trigger, dial, button, etc., may be used to generate a desired deflection angle, as previously stated.

Figure 2A:
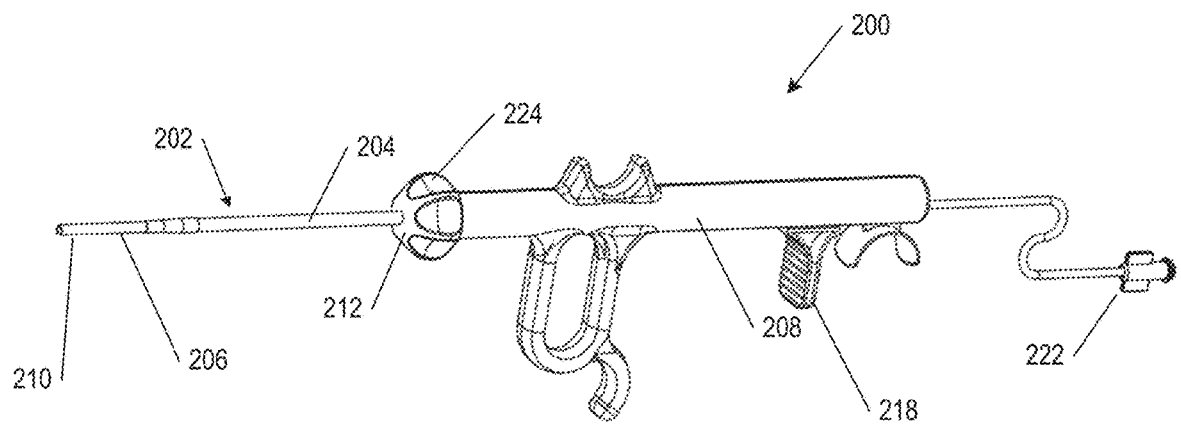
FIGS. 2A-2C depict an exemplary system for accessing anatomical structures of the ear, nose, and throat.

The systems are capable of use with a single hand. As shown in FIG. 2A, an exemplary system (200) may include an applicator (202), the applicator (202) having a proximal end (204), a deflectable distal end (206), and a distal tip (210). The distal tip may be soft and/or atraumatic, and formed from materials having a durometer suitable for that purpose. The applicator is generally a multi-lumen catheter having an outer diameter ranging from about 2 mm to about 10 mm. When the sinus anatomy is being accessed, the applicator may have an outer diameter ranging from about 2 mm to about 5 mm. In variations where an airway is being accessed, the outer diameter of the applicator may range from about 6 mm to about 8 mm. As illustrated in the cross-sectional view of the applicator in FIG. 2B, the applicator (202) may include a device lumen (214), and a pullwire lumen (220). Portions of the applicator may be made to be sufficiently rigid to prevent kinking during deflection. Rigidity may be provided by reinforcing appropriate areas of the applicator with braiding or by varying the thickness of the applicator wall, where an increased wall thickness imparts greater rigidity and a decreased wall thickness imparts less rigidity to the applicator. Alternatively, the applicator may be made from materials of different durometer to vary the rigidity and flexibility of portions of the applicator. Referring back to FIG. 2B, applicator (202) may be reinforced with braiding (222) to prevent kinking of the applicator during steering or deflection. The device lumen (214) may have any suitable diameter for passage of a device, and range for example, between about 2.0 mm to about 3.0 mm, or between about 2.3 mm to about 2.6 mm. In one variation, the device lumen may be about 2.3 mm. In another variation, the device lumen may be about 2.4 mm. In yet another variation, the device lumen may be about 2.5 mm. In a further variation, the device lumen may be about 2.6 mm. Additionally, the length of the applicator may range from about 9 cm to about 16 cm.

A handle may be coupled to the applicator and have an elongate slot having a travel length, and a finger slide coupled to a guidewire and movable along the travel length to advance the guidewire through the applicator. A single pullwire may be attached to the applicator distal tip and extend proximally through the pullwire lumen. An adjustment knob may be coupled to one of the applicator or the single pullwire, where rotation of the adjustment knob bends the deflectable distal end of the applicator to a deflection angle that provides access to the target tissue site.

The applicator is generally configured so that deflection of its distal end is adjustable to different deflection angles in order to access various target tissue sites using a single applicator, as further described below. In one variation, a single applicator is configured to adjustably deflect to different deflection angles to allow a single balloon catheter to access multiple paranasal sinuses. In some variations, the balloon catheter is used to dilate a paranasal sinus ostium. In other variations, the balloon catheter is used to deliver a drug, e.g., via a drug coating, to a paranasal sinus ostium. An exemplary drug or combination of drugs may include mometasone furoate. In yet further variations, the balloon catheter is used to both dilate a paranasal sinus ostium and deliver a drug thereto. When a drug is being delivered, the applicator may include one or more features that minimize drug loss during balloon deployment multiple times to the same paranasal sinus ostium or different paranasal sinus ostia. A device lumen and a pullwire lumen typically extend from the proximal end to the distal tip of the applicator. The distal end may be formed such that it has sufficient flexibility to deflect upon actuation by a pullwire, which runs through the pullwire lumen to the distal tip. The pullwire may be attached to the distal tip at an anchoring point with any suitable adhesive or by soldering, or by welding, and in some instances may be affixed to the distal tip with the assistance of a metal o-ring. Exemplary materials from which the applicator may be made include without limitation, (acrylonitrile butadiene styrene (AB S), nylon polymers, polyether ether ketone (PEEK), Pebax® elastomers, polyimide, polyvinyl chloride, polyethylene, and combinations thereof. The applicator length may have a length ranging from about 9 cm to about 16 cm, but may be shorter or longer depending on the target anatomy and tissue site to be accessed. The applicators described herein generally only include a single pullwire, but in some instances may include multiple pullwires. Given that only a single pullwire is typically employed to effect deflection, the diameter of the applicator may be minimized, which improves ease of use by the physician, especially when used in conjunction with an endoscope. Manufacturing of the applicator may also be simplified when only a single pullwire is employed.

In aspects, one end of the pullwire can be coiled around the exterior circumference of the distal end of the applicator (or secured to such a coil), which thereby lends a spring force or resilient force to the distal tip, such that in the absence of applied tension, the distal tip reverts to a straight (zero degree) configuration. In such and further implementations, the applicator is not configured to have a malleable tip which could be bent by the hand of an operator or by other means, because the spring force imparted to the distal tip would tend to straighten the distal tip and not hold a variably formed shape like a malleable structure.

Figure 2B:
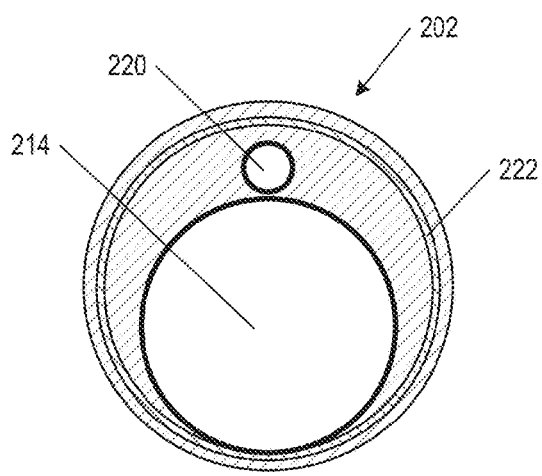
Figure 2C:
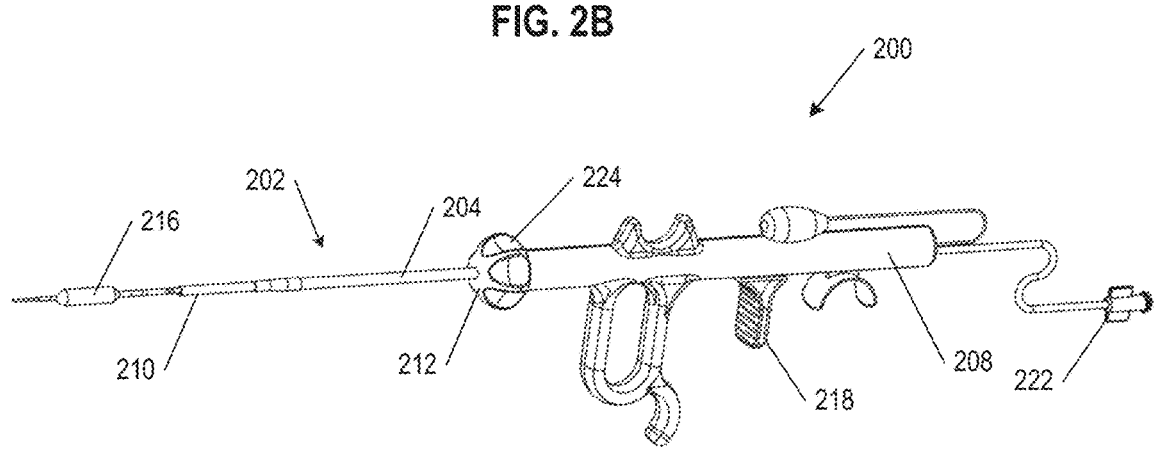

A device (e.g., an expandable balloon (216) in FIG. 2C) may be advanced through the device lumen to a target tissue site. Although an expandable balloon is shown in the figure, it is understood that other devices (e.g., stents) may be deployed through the applicator. The devices may or may not be expandable, and may or may not include a drug for delivery to the target tissue site. The drug may be present on any portion of the device. It may be dispersed entirely within the material of the device or in portions thereof. The drug may also be included in a coating provided on the entire device or a portion thereof. In some instances, the devices are used to maintain patency of the target tissue site. In other instances, the devices are used to dilate the target tissue site. In yet further instances, the devices are used to both dilate and deliver drug to the target tissue site.

The outer diameter of the device lumen may range from about 3.0 mm to about 3.5 mm. For example, the outer diameter may be about 3.0 mm, about 3.1 mm, about 3.2 mm, about 3.3 mm, about 3.4 mm, or about 3.5 mm. The device lumen may be made from a lubricious material, or its interior coated with a lubricious material. Use of a lubricious material may be beneficial in minimizing drug loss from a device being deployed from the applicator. Exemplary lubricious materials include, but are not limited to, fluorinated propylene ethylene (FEP), poly(methyl methacrylate) (PMMA), polyurethane, polytetrafluoroethylene (PTFE), silicone elastomers, and combinations thereof. The pullwire lumen may have an inside diameter ranging from about 0.25 mm to about 0.5 mm.

Various devices may be deployed through the applicator to a target tissue site. In some instances, the device may include a drug, for example a drug within a coating thereof. In one variation, the drug-coated device is a drug-coated balloon. Here it may be useful for the applicator to include features that help minimize drug loss during device deployment. For example, modifying the applicator distal tip to prevent scraping of drug off the device may be useful. The distal tip may be structured to be flared, conical, and/or its edges rounded to help minimize drug loss. Alternatively, the device lumen can be made from, or coated with, a lubricious material, as stated above.

A handle is generally fixedly attached to the proximal end of the applicator, as previously stated. In some variations, attachment of the handle to the applicator proximal end is accomplished via one or more flanges. For example, one flange may be used, or a flange assembly including two or more flanges may be employed. Complimentary structures, e.g., complimentary threads on the flanges and housing of the handle may be used to effect mating of the handle to the applicator. The handle may include a pistol-like finger grip and an actuator such as a finger slide coupled to a guidewire. An elongate slot having a travel length ranging from about 5 cm to about 20 cm may be provided on a portion of the handle, along which the finger slide may advance to advance the guidewire through the applicator toward the target tissue site. In some variations, the travel length is about 5 cm, about 6 cm, or about 7 cm. The handle may be made from materials including, but not limited to, (acrylonitrile butadiene styrene (ABS), polycarbonate (PC), polybutylene terephthalate (PBT), nylon polymers, polyether ether ketone (PEEK), Pebax® elastomers, polyimide, polyvinyl chloride, polyethylene polyurethane, and combinations thereof. In some variations, glass is mixed with the polymer material to increase the strength of the handle. The glass may form about 5%, about 10%, about 15%, or about 20% of the handle material, by weight.

Figure 11:
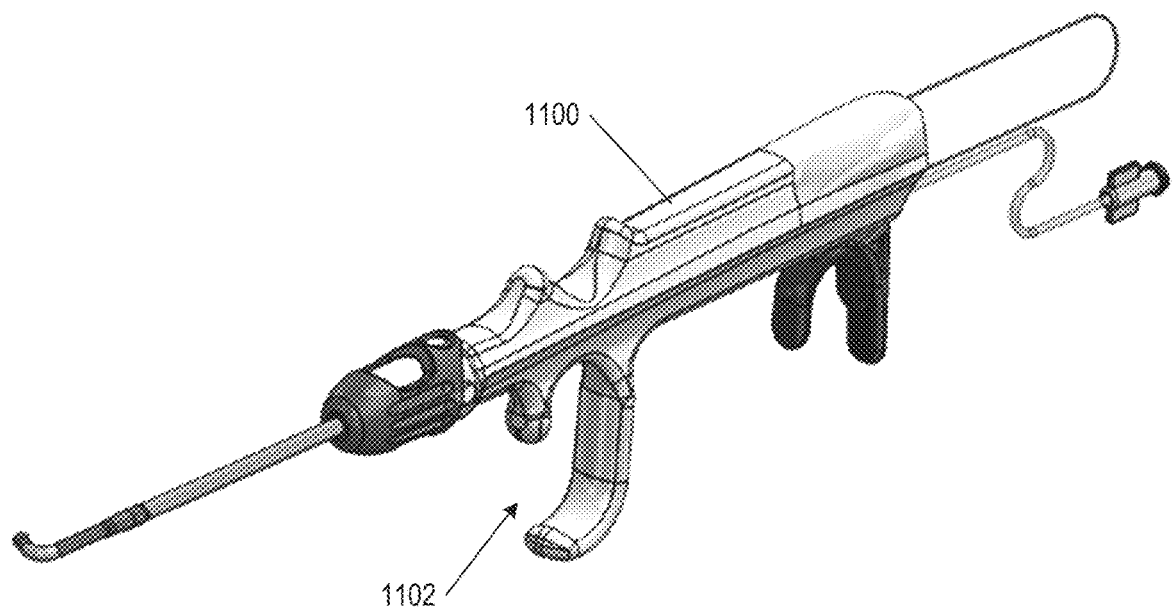
FIG. 11 depicts a handle of the system according to one variation.
Figure 12:
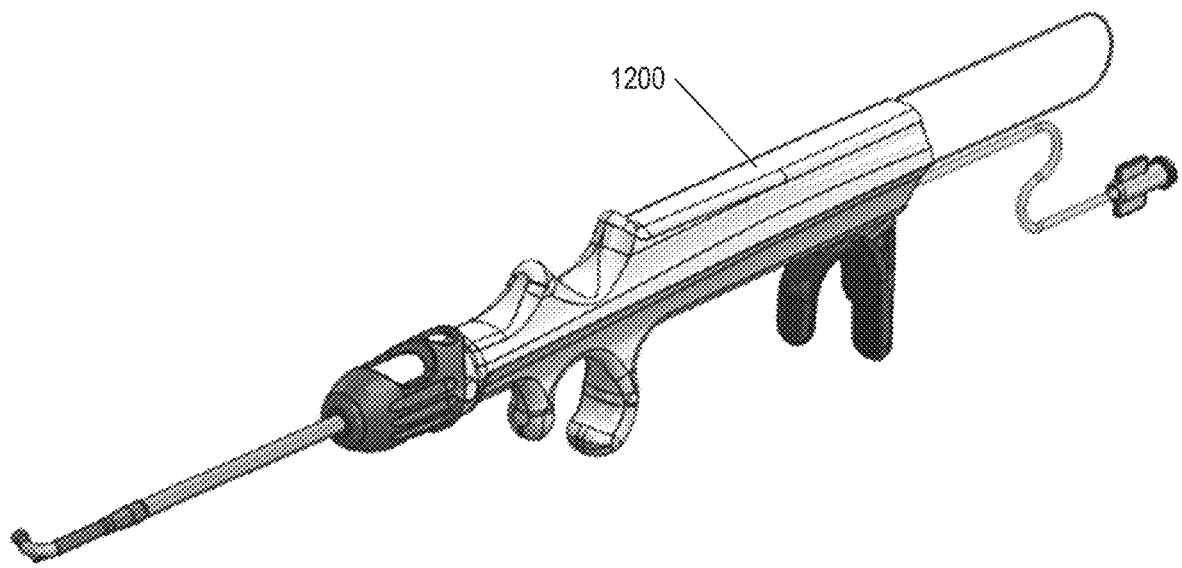
FIG. 12 depicts a handle of the system according to another variation.

The handles will generally be configured to have a low overall profile while providing the desired stability and ergonomics for navigating the anatomy of target tissue sites. The profile of the handle may be minimized by employing a single pullwire, and other system features such as lower profile balloon catheters, as further described herein. In some variations, for example when the physician has larger hands, the handle (1100) may be configured to include an open loop (1102) which allows more stable gripping and maneuvering of the system, as shown in FIG. 11. In other variations, the overall profile of the handle may be minimized by making handle (1200) shorter, as shown in FIG. 12. The height of such a short handle may range from about 3.5 cm to about 5.5 cm in comparison to a typical handle, which ranges from about 7.0 cm to about 8.5 cm.

The guidewire used with the systems described herein may be any conventional guidewire. If desired, an illuminating guidewire (alternatively referred to as a "lightwire"), as further described herein may be employed. The illuminating guidewire may be connected to a light source and include an illuminating portion at a distal end thereof. Illumination of the illuminating guidewire may be used to visually confirm the positioning of a distal end of the applicator and/or device advanced therethrough. In use, a distal end portion of the illuminating guidewire may be advanced to a target tissue site within a patient, and upon observing the transillumination on an external surface of the patient, the physician can correlate and confirm the location of the observed transillumination with an internal location of the patient.

In some implementations, two or more illuminating guidewires may be bundled or braided together such that the two or more illuminating guidewires in combination have particular strength and resilience characteristics as compared to a single illuminating guidewire (e.g., greater or lesser stiffness, greater or lesser ability to hold shape when bent, etc.). In further implementations, the two or more illuminating guidewires can be bundled or braided together with a relatively flexible metal core component (e.g. a NiTi wire) such that the overall guidewire has particular strength and resilience characteristics as compared to a single illuminating guidewire.

The exemplary system (200) shown in FIGS. 2A-2E can include a fluid port (222) configured to couple to a fluid source that can be used to inflate the expandable balloon (216) with a fluid, and to also to provide an egress to draw out fluid from and deflate the expandable balloon (216).

Instead of multiple pullwires, the systems described herein generally employ a single pullwire to deflect the distal end of the applicator to different deflection angles. The pullwire may be made from any suitable metal, for example, stainless steel, Nitinol® metal alloy, etc. Alternatively, the pullwire may be made from a polymeric material such as polyimides, polytetrafluoroethylene (PTFE), and polyurethanes. In one variation, only a single pullwire is employed to minimize the outer diameter of the applicator to thus improve steering through inflamed and/or stenotic passageways, as previously mentioned. The single pullwire may be attached at one end to the applicator distal tip and extend proximally through the pullwire lumen to couple with an adjustment knob. The pullwire may be a straight wire or a coiled wire that runs from the distal tip to a proximal part of the applicator, for example, the adjustment knob. Attachment may be accomplished in any suitable fashion, for example, via use of any suitable adhesive, soldering, ultrasonic welding, insert molding, etc.). In some variations, rotation of the adjustment knob will effect translational movement of the pullwire proximally, which in turn deflects the distal end of the applicator.

Figure 5A:
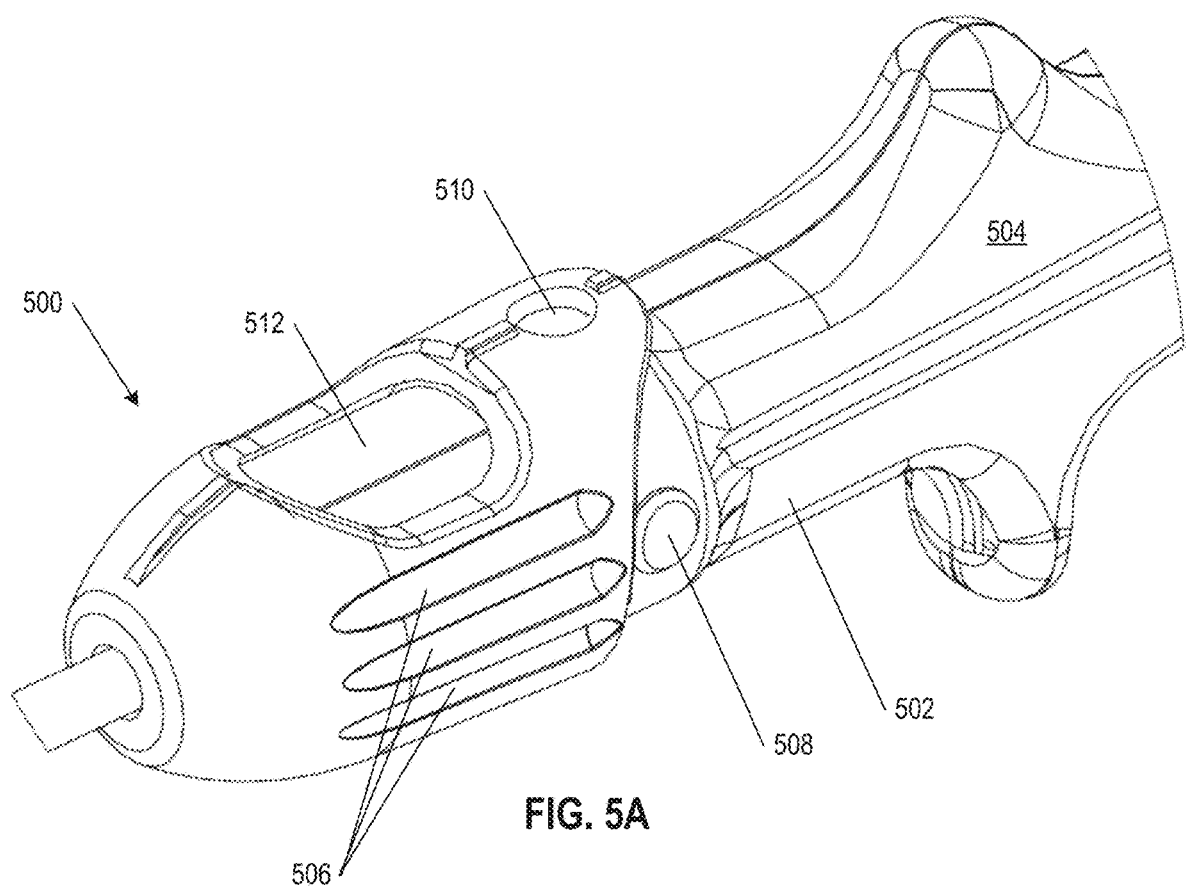
FIG. 5A depicts another variation of an adjustment knob of the system.

The adjustment knob may be coupled to the applicator in any suitable manner that allows rotation thereabout, e.g., by an interlocking fit or press fit thereon. Furthermore, the adjustment knob may have any suitable shape and geometry that allows ease of grip for rotational movement. For example, as shown in FIGS. 2A and 2C, the adjustment knob (212) may be configured to have a generally circular shape, and include a number of depressions or detents (224) that promote gripping of the knob so that it can be rotated. Alternatively, as shown in FIG. 5A, the adjustment knob (500) may have a lower profile than that of knob (212) in FIGS. 2A and 2C, and be concentrically disposed about the distal portion (502) of the handle (504). Here the detents (506) are shallower and run longitudinally with respect to the knob (500). Any suitable number of detents may be used, and they may be arranged on the adjustment knob in any suitable fashion. Tabs (508) may also be provided on the handle distal portion (502) that fit into corresponding openings (510) in the knob (500). During rotation of the knob (500), the tabs (508) and openings (510) may be used to hold the rotational position of the knob at a specific degree, e.g., 30 degrees, 45 degrees, 90 degrees, 120 degrees, 180 degrees, 225 degrees, 270 degrees, 315 degrees, or 360 degrees, from a starting position. The adjustment knob may rotate either clockwise or counterclockwise. Further, the tabs will typically have a height useful to temporarily lock the knob (500) at a particular rotational position, but which also allows rotation of the knob to the next tab with application of additional rotational force. Any suitable number of tabs and openings may be used, but the number will generally depend on the number of positions to which the knob is to be rotated. The knob (500) may also include a window (512) that can indicate which paranasal sinus/ostia or tissue is being targeted at each rotational position, the deflection angle orientation of the distal tip for each rotational position, or a further indication or characterization of the applicator with the knob at each rotational position.

The adjustment knob may be configured to be freely rotated about the axis of the applicator so that the physician may rotate it to any desired amount, e.g., as much or as little as desired. Alternatively, the adjustment knob may be configured to include preset amounts or degrees of rotation that correspond to predetermined deflection angles of the applicator distal end. In one variation, the adjustment knob may lock into place when the preset amount of rotation is reached. In another variation, the physician may rotate the knob as much or as little as desired up until the preset amount. Adjustment knob rotation may be manual or automated.

Figure 2D:
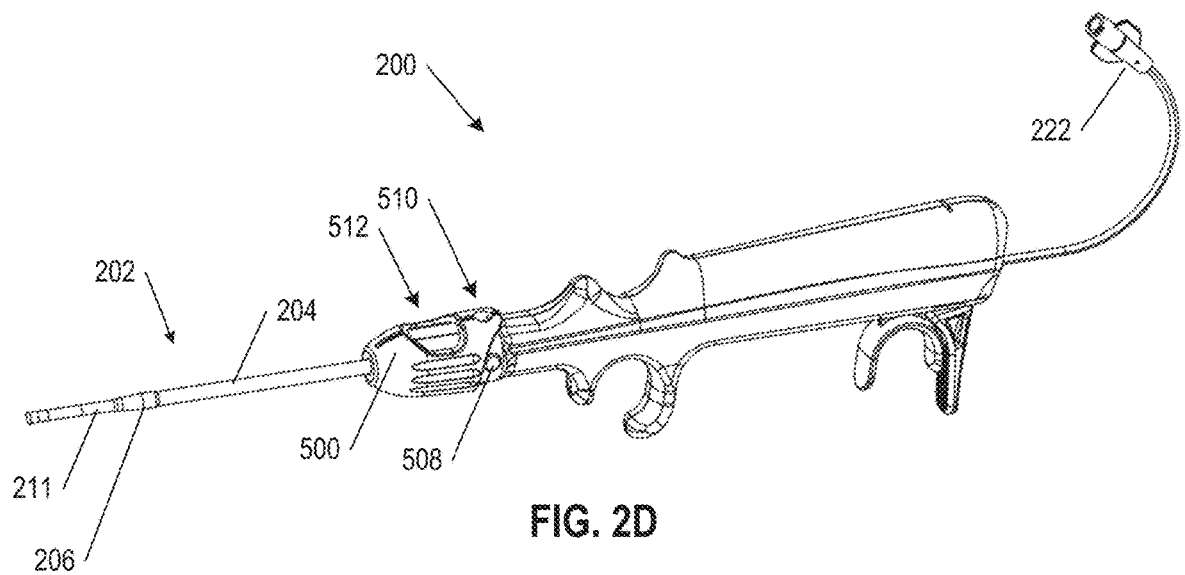
FIGS. 2D and 2E depict an alternative exemplary system for accessing anatomical structures of the ear, nose, and throat.
Figure 2E:
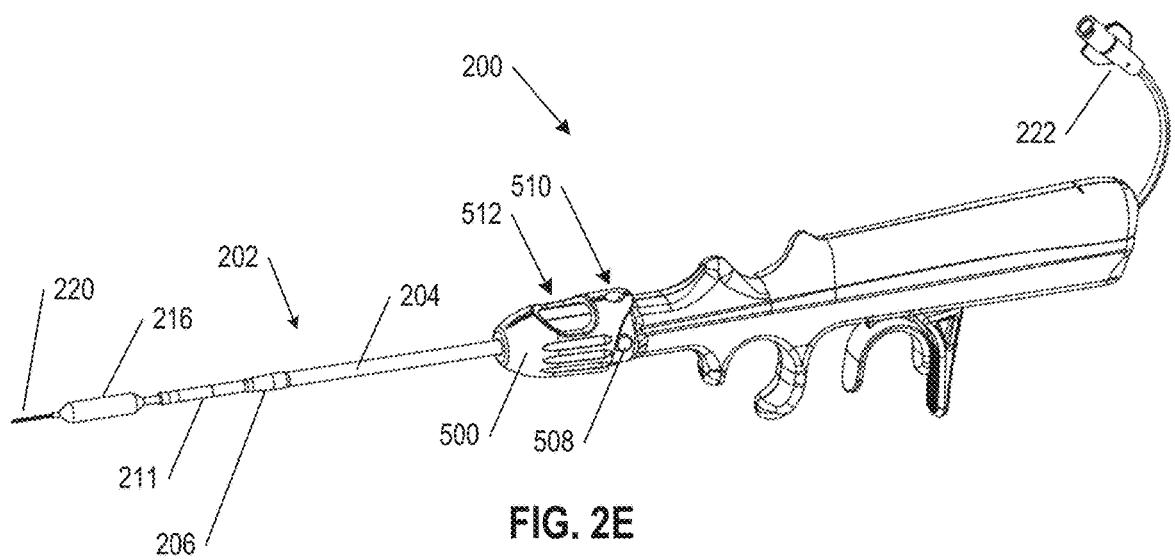

FIGS. 2D and 2E illustrate a version of the applicator using the adjustment knob (500) as shown in FIG. 5A and having a handle similar to that seen in FIG. 12. This exemplary variation is similar to the version shown in FIGS. 2A and 2C, having an applicator (202) with a proximal end (204), a deflectable distal end (206), and a flared distal tip (210). An expandable balloon (216) can pass through the lumen of the applicator 202 out past the end of the flared distal tip (211) in an uninflated state (a low-profile configuration) and inflated once positioned at a target tissue location. A guidewire (220) can be used to advance the expandable balloon (216) through the applicator (202) at any functional configuration of the deflectable distal end (206) and flared distal tip (211). In some aspects (as shown in FIG. 2E), the guidewire (220) can extend a length past the distal end of the expandable balloon (216). In other aspects, the guidewire can effectively co-terminate at the distal end of the expandable balloon (216). In either implementation, the guidewire (220) can be configured to have a flexibility and/or durometer that is atraumatic.

The inflated width or diameter of an expandable balloon as described herein can be selected or configured based on the anatomical structure or orifice being dilated. The choice of balloon can be important, as various airways within a body can range in average width from about five millimeters to about sixteen millimeters, recognizing that some individual anatomies may be outliers smaller or larger than the range of average widths. In some implementations, the expandable balloon can be expanded to a diameter of about 6.0 mm (±0.3 mm). In other implementations, the expandable member can be configured to expand to have a diameter of about from 5.0 mm to about 7.0 mm when inflated. In other implementations, the expandable member can be configured to expand to have a diameter of about from 4.0 mm to about 20.0 mm when inflated.

Figure 5B:
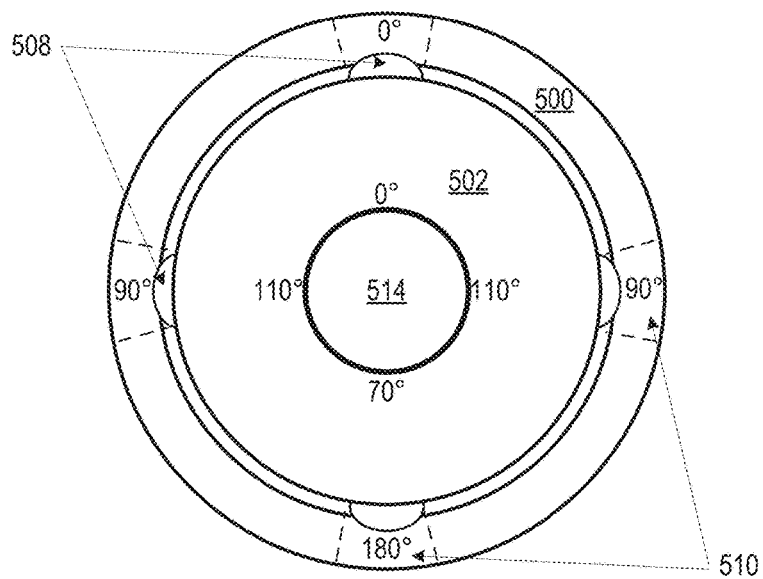
FIG. 5B depicts a schematic representation of the adjustment knob system as disclosed in FIG. 5A, further illustrating the relationship between the rotation of the adjustment knob and corresponding changes to the orientation of a connected distal tip.

FIG. 5B is a schematic representation of the adjustment knob (500), viewing a lateral cross-section, that further illustrates an exemplary correlation between the position of the adjustment knob (500) and the deflection angle orientation of the related distal tip (514). Similar to the set of images shown in FIG. 1, with an opening (510) of the adjustment knob (500) set around a tab (508) on the top (dorsal) surface of the handle at a zero degree (0°) position, the distal tip (514) is also oriented at to be a zero degree (0°) position (in other words, straight). With an opening (510) of the adjustment knob (500) set around a tab (508) on the bottom (ventral) surface of the handle at a one hundred eighty degree (180°) position, the distal tip (514) is oriented at to be a seventy degree (70°) position, bent away from the longitudinal axis of the applicator. With an opening (510) of the adjustment knob (500) set around a tab (508) on the left-side surface of the handle at a ninety degree (90°) position, the distal tip (514) is oriented at to be a one hundred ten degree (110°) position, bent to the left away from the longitudinal axis of the applicator. With an opening (510) of the adjustment knob (500) set around a tab (508) on the right-side surface of the handle at a ninety degree (90°) position, the distal tip (514) is oriented at to be a one hundred ten degree (1100) position, bent to the right away from the longitudinal axis of the applicator.

As set forth in further detail below, a pullwire proximally coupled to the adjustment knob and distally coupled to the distal dip allows for the rotation of the adjustment knob to affect the deflection and change in orientation of the distal tip. The specific degree of deflection effectuated through the pull wire due to rotation of the adjustment knob can be configured by altering the tension on the pullwire, the length the pullwire is moved along the longitudinal axis of the applicator, the number of coils the pullwire forms or is connected to around the distal tip, other characteristics of the pullwire, or a combination thereof. Accordingly, in other embodiments, rotation of the adjustment knob to each of the tab positions can be configured to deflect the distal tip to other angles than illustrated above. Further, the number of tabs around the exterior of the handle distal portion may be greater than (e.g. 5, 6, 7, or 8 tabs) or less than (e.g., 2 or 3 tabs) the four shown in the exemplary embodiment, providing for a different number of predetermined set-points and distal tip deflection angle configurations for the applicator.

As an example of an alternative application for the present access and expansion device, a deflection angle of forty-five degrees (45°) or one hundred thirty-five degrees (135°), relative to the longitudinal axis of an applicator, can be advantageous for accessing Eustachian tubes.

In general, the pullwire is attached to a first flange. The mechanism of turning rotational movement of the adjustment knob into axial movement of the pullwire (i.e., the deflection mechanism) will differ depending on the manner in which the first flange is coupled to other components of the system. In one variation, the deflection mechanism includes a first flange coupled to the housing of the handle. In another variation, the deflection mechanism includes a first flange coupled to the adjustment knob. In a further variation, the deflection mechanism includes a first flange coupled to a second flange, which works is conjunction with a ratchet assembly to deflect the applicator distal end.

The first and second flanges may be configured as bobbin-like or screw-like structures and include threads, channels, windings, guides, etc., that help to rotationally guide the adjustment knob with respect to the handle, and in some instances, also axially move the pullwire back and forth. The pitch or spacing between the threads, channels, windings, or guides may be adjusted to vary the amount of axial movement of the pullwire. In some variations, the first or second flange may include teeth at one end, alone or in combination with the threads, windings, or guides at the other end. The teeth may useful in variations where a ratchet assembly is employed to retract the pullwire in a step-wise fashion. The first and second flanges may be made from any suitable material, for example, acrylonitrile butadiene styrene (ABS) polymer, polycarbonate, and the like.

Figure 3A:
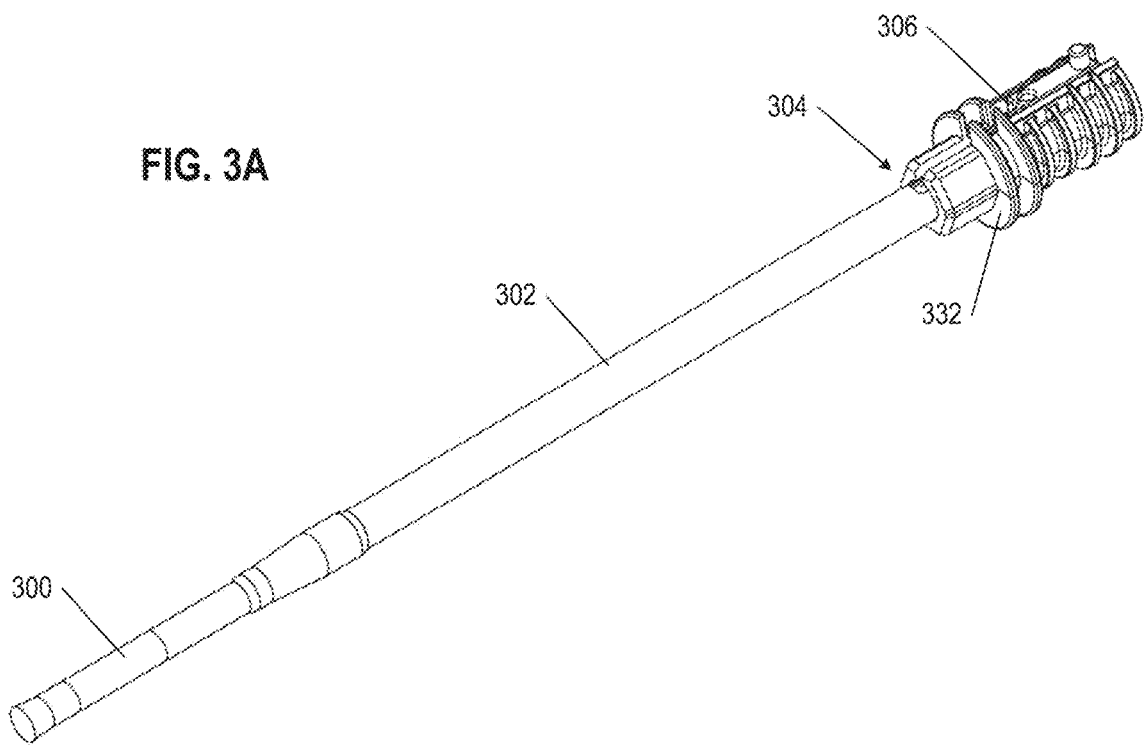
FIGS. 3A-3K illustrate the deflection mechanism of the system according to one variation.
Figure 3B:
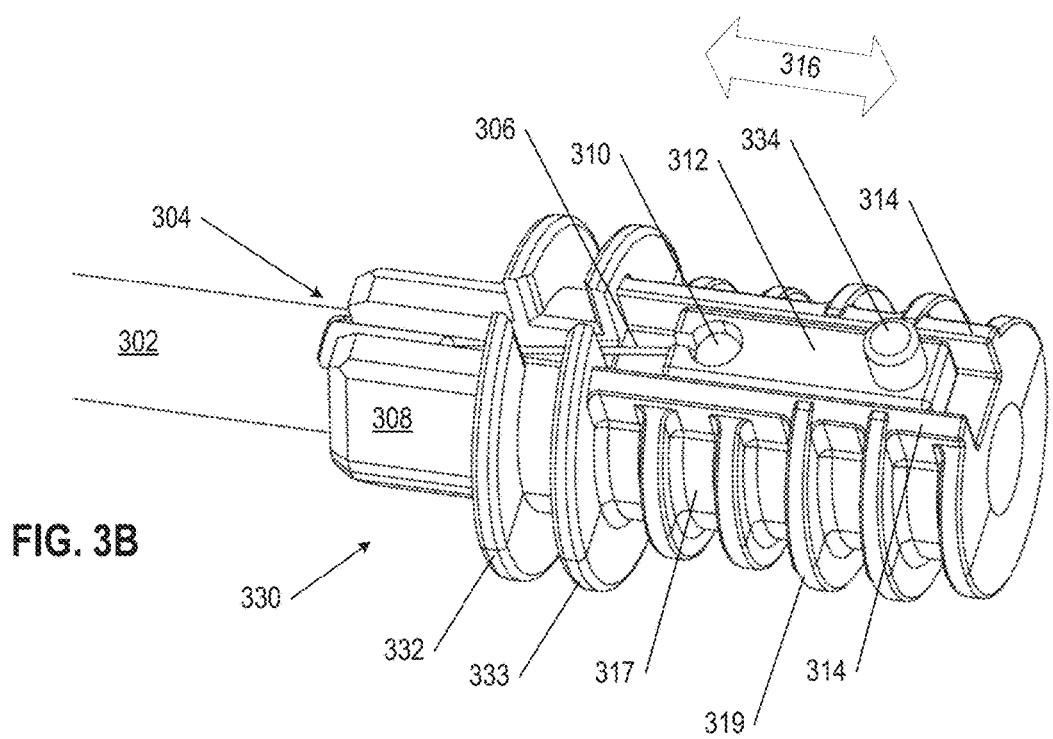
Figure 3C:
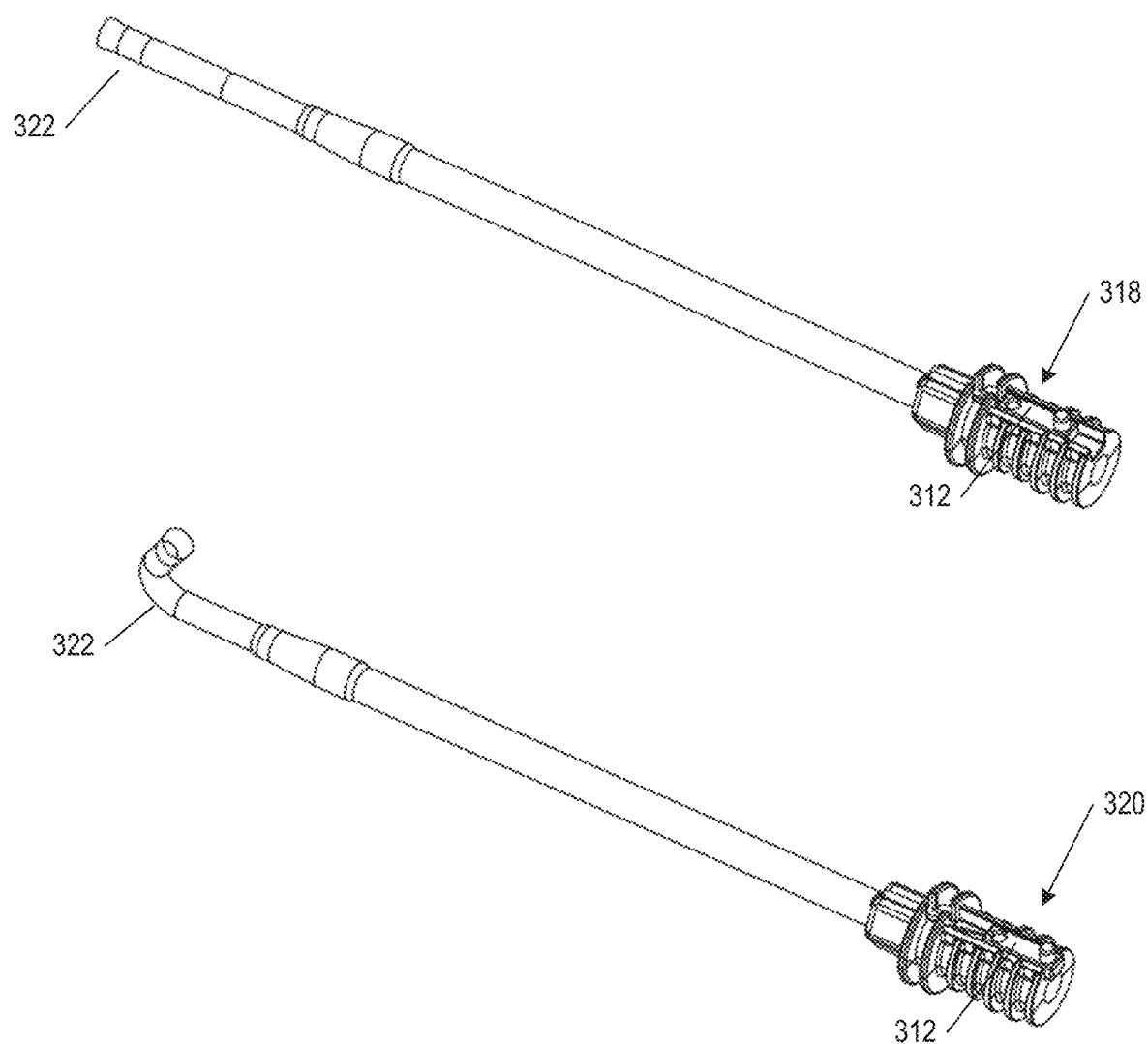
Figure 3D:
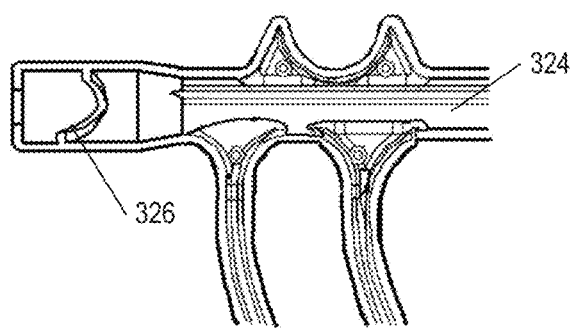
Figures 3E, 3F, 3G:
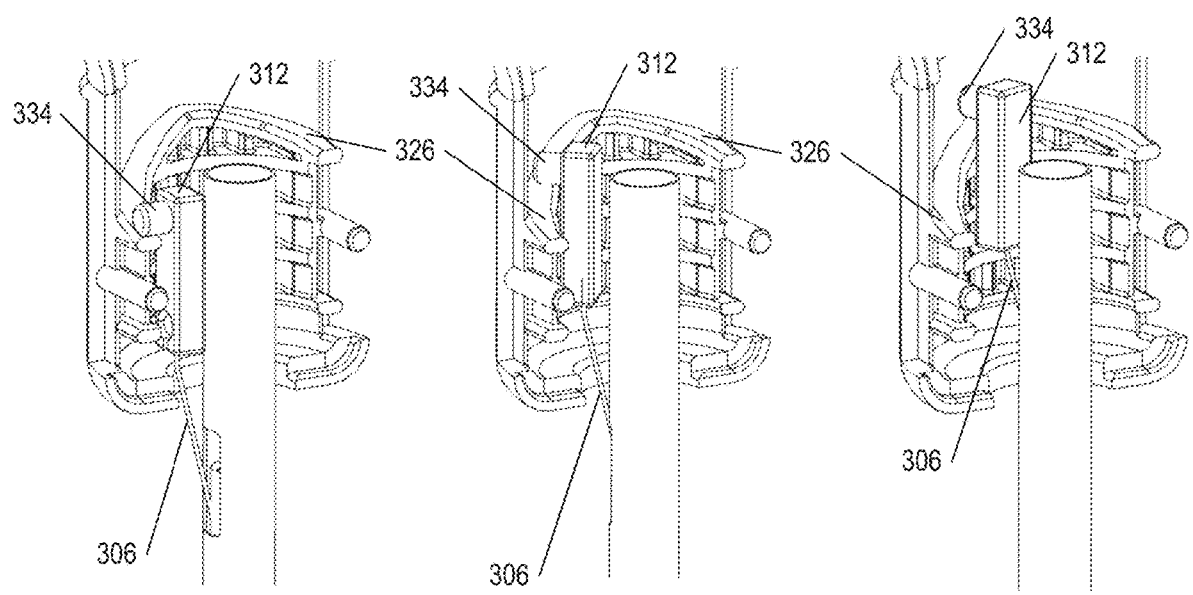
Figure 3H:
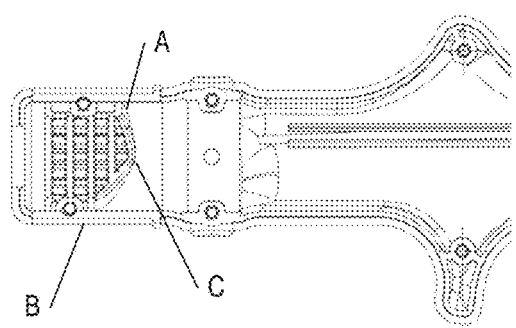
Figure 3I:
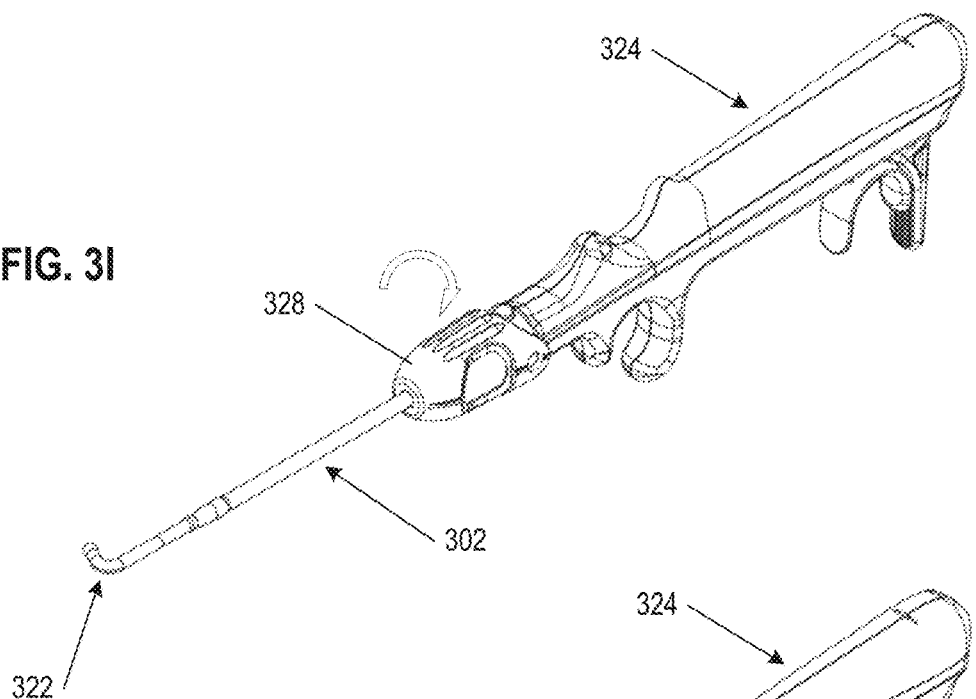
Figure 3J:
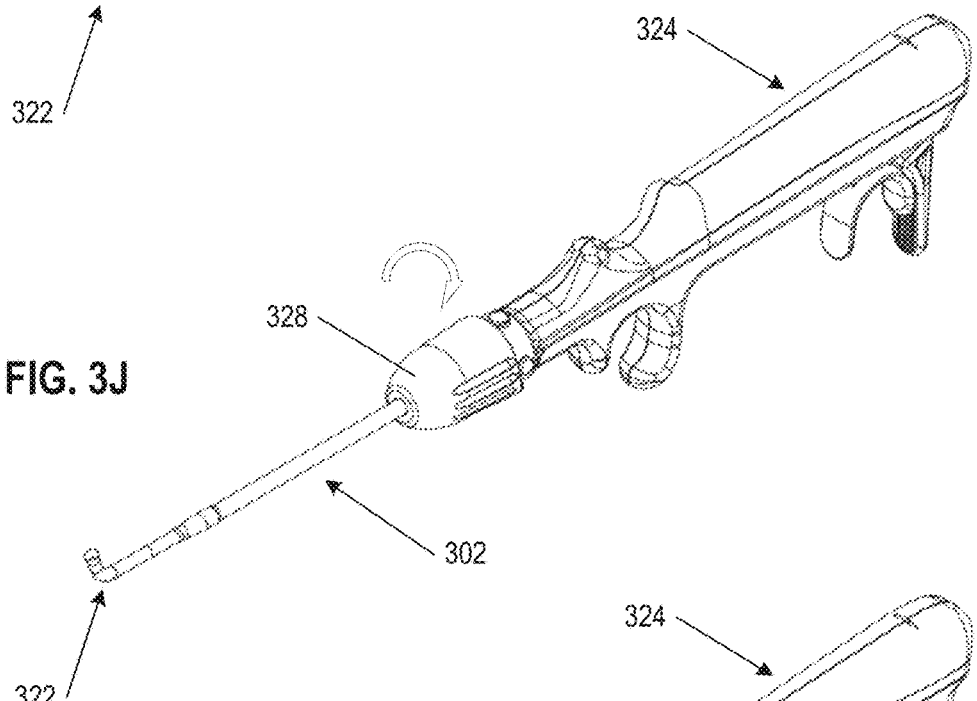
Figure 3K:
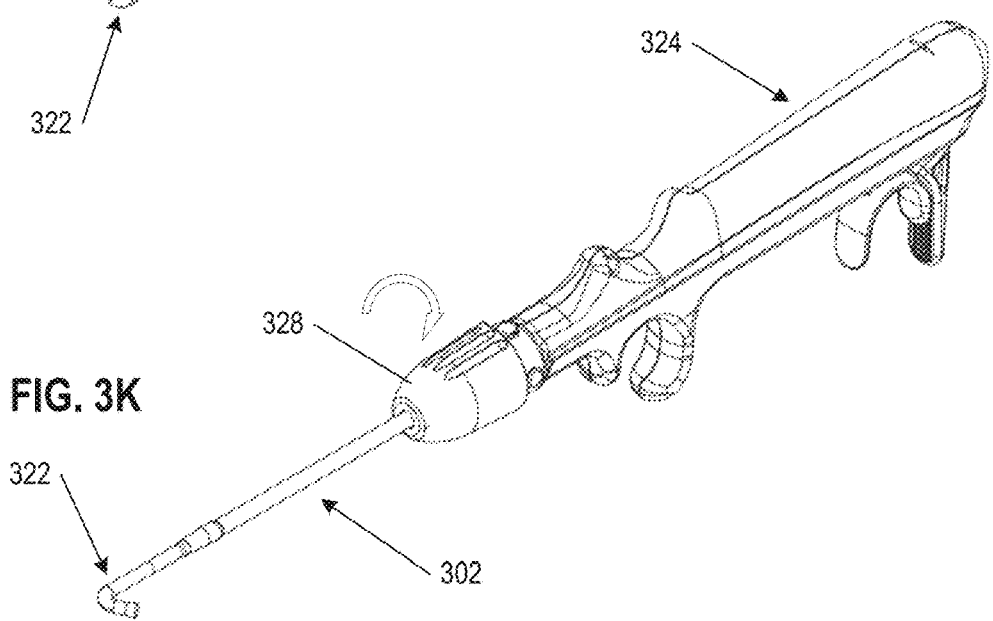
Figure 3L:
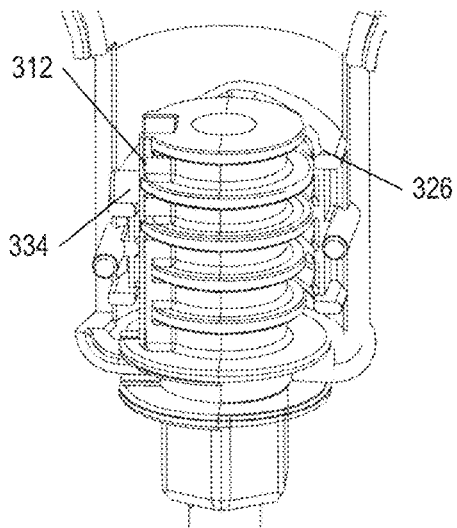
FIGS. 3L-3P show details of an alternative implementation of the deflection mechanism used to bend the applicator of the system.
Figure 3M:
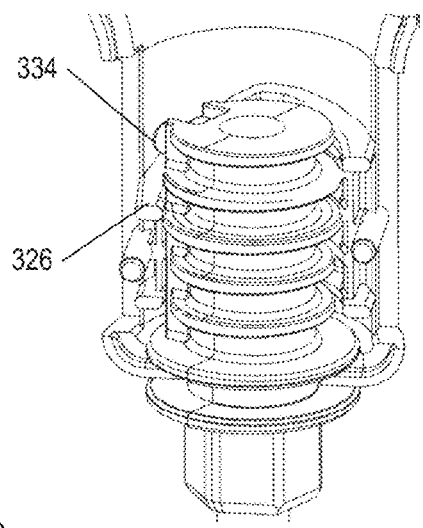
Figure 3N:
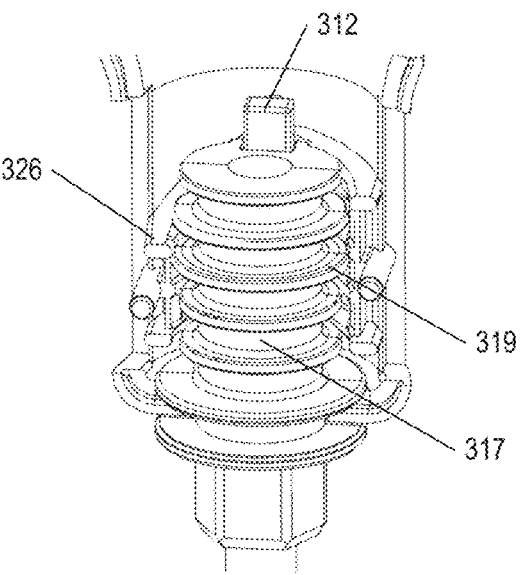
Figure 3O:
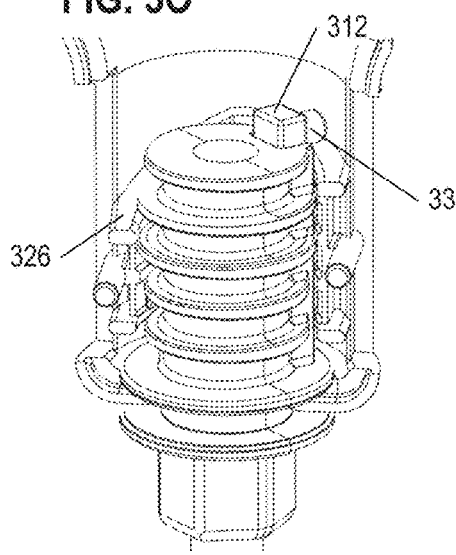
Figure 3P:
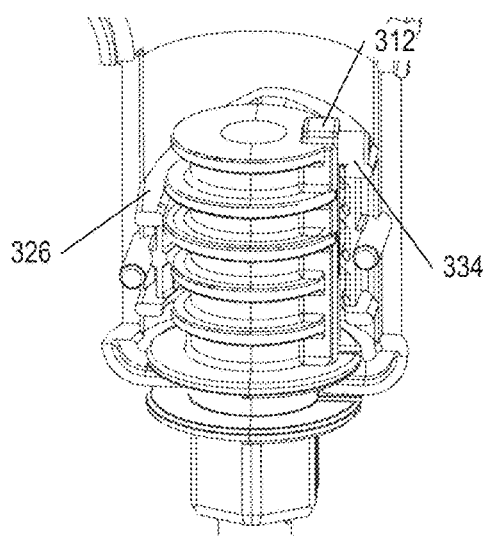

For example, as shown in FIGS. 3A and 3B, the applicator has a deflectable portion (300) and a rigid portion (302). An opening (304) in the proximal end of the rigid portion (302) is provided for pullwire (306) to exit. In some variations, as shown in FIG. 3B, a distal end (330) of the flange (332) includes a shoulder (308), where the flange (332) is configured to mate with a corresponding structure in the handle housing, and where the shoulder (308) is configured to mate with a region of the adjustment knob. Here the deflection mechanism may be configured as shown in FIGS. 3A-3H, and function as shown in FIGS. 3I-3K. In this variation, the deflection mechanism includes a pullwire (306) coupled to the first flange via a cam mechanism. The pullwire (306) may exit an opening (304) in the proximal end of the applicator rigid portion (302) and be secured to the cam mechanism by a ball and socket type joint, where the proximal end of the pullwire is attached to the ball, and the ball disposed within a complimentary fitting in the cam mechanism. In other aspects, the pullwire (306) can be directly attached to the cam mechanism (312). A first flange (332) connected to the applicator is also connected to the adjustment knob (328) (see FIGS. 3I to 3K). The pullwire (306) extends up a ramp of the deflection mechanism to be secured by a spherical component (310). Spherical component (310) sits within a fitting of a cam follower (312) and holds the pullwire (306) down such that movement of the cam follower (312), resting within a follower guide (317), leads to corresponding movement of the pullwire (306). Rails (314) that are coupled to the second flange (333) only allow the cam follower (312) to translate in an axial direction, in the direction of the arrows (316). In some aspects, additional threading (319) can extend around portions of the deflection mechanism, which can provide for greater structural strength and/or surfaces that can interact with surrounding structures of the adjustment knob or handle. For example, as illustrated in FIGS. 3B and 3C, proximal movement of the cam follower (312) from a resting position (318) to a more proximal position (320) pulls the pullwire to thereby deflect the distal end (322) of the deflectable portion (300) of the applicator. Depending on the target tissue site, the applicator distal end may be deflected to a deflection angle of about 10 degrees, about 20 degrees, about 30 degrees, about 40 degrees, about 50 degrees, about 60 degrees, about 70 degrees, about 80 degrees, about 90 degrees, about 100 degrees, about 110 degrees, or about 120 degrees. In some variations, the deflection angle may be greater than 120 degrees.

Referring to FIGS. 3D to 3G, a ramp or cam surface (326) may be located within the handle (324), and structured to move the cam follower (312) and pullwire (306) secured thereto to different axial positions along axis of the handle and applicator. In alternative embodiments, the cam surface (326) can be a groove in an internal surface of the handle (324) or the adjustment knob. Cam follower (312) is coupled to the ramp or cam surface (326) via a peg (334), which in turn is coupled to the adjustable knob. Thus, clockwise or counterclockwise rotation of the applicator achieved by rotation of the adjustment knob may allow the peg (334) and associated cam follower (312) to travel along the ramp or cam surface (326) to different axial positions, e.g., axial positions A, B, and C, as shown in FIG. 3H, which pulls the pullwire different distances, thereby deflecting the distal end of the applicator by different amounts or angles. For example, as shown sequentially in FIGS. 3E to 3G, as the cam follower (312) travels along ramp or cam surface (326) it is pulled proximally to thereby pull the pullwire (306) and deflect the distal end of the applicator.

In an alternative example, as shown sequentially in FIGS. 3L to 3P, the cam follower (316) also follows the ramp or cam surface (326), due to directional force on the peg (334) caused by rotation of the adjustment knob, thereby moving proximally and pulling a pullwire to deflect the distal end of the applicator. In this example, threading (319) is present around the follower guide (317), providing for additional structural strength and additional surface for interaction with structures or articulation present on the interior surfaces of a device. In both examples described above, further rotation of the adjustment knob (either clockwise or counterclockwise) can lead to further travel of the peg (334) along the cam surface (326), leading to linear translation of the cam follower (316) along the length of the defection mechanism.

The angle selection knob may be configured to be rotated in 90 degree increments (moving the cam follower positioned underneath the knob), although other increments may be employed, and may be rotated either clockwise or counterclockwise. In such an implementation, the applicator (300) starts with zero degrees (0°) of deflection (such as in FIG. 2D), which may be used to treat the sphenoid sinuses. As the adjustment knob (328) is rotated 90 degrees clockwise (viewing the applicator (302) and handle (324) straight-on from the distal end, with an arrow indicating the direction of rotation, as seen in FIG. 3I) while maintaining the same handle orientation, the applicator distal end (322) is deflected to approximately 120 degrees so that the left maxillary sinus may be treated. Rotating the adjustment knob (328) an additional 90 degrees (as seen in FIG. 3J) while maintaining the same handle orientation generally deflects the applicator distal end (322) to approximately 70 degrees so that both left and right frontal sinuses may be treated. As the adjustment knob is rotated yet another 90 degrees (as seen in FIG. 3K) while maintaining the same handle orientation, the applicator distal end (322) is deflected to approximately 120 degrees so that the right maxillary sinus may be treated. However, depending on the target tissue site, the applicator distal end may be deflected to a deflection angle of about 10 degrees, about 20 degrees, about 30 degrees, about 40 degrees, about 50 degrees, about 60 degrees, about 70 degrees, about 80 degrees, about 90 degrees, about 100 degrees, about 110 degrees, or about 120 degrees. In some variations, the deflection angle may be greater than 120 degrees.

In some variations, the deflection mechanism includes a first flange that is directly coupled to the adjustment knob instead of the handle. For example, a shoulder provided on the first flange may mate with a corresponding groove along the interior surface of the adjustment knob so that rotation of the adjustment knob results in proximal movement of the pullwire and subsequent deflection of the distal portion of the applicator.

Figure 6A:
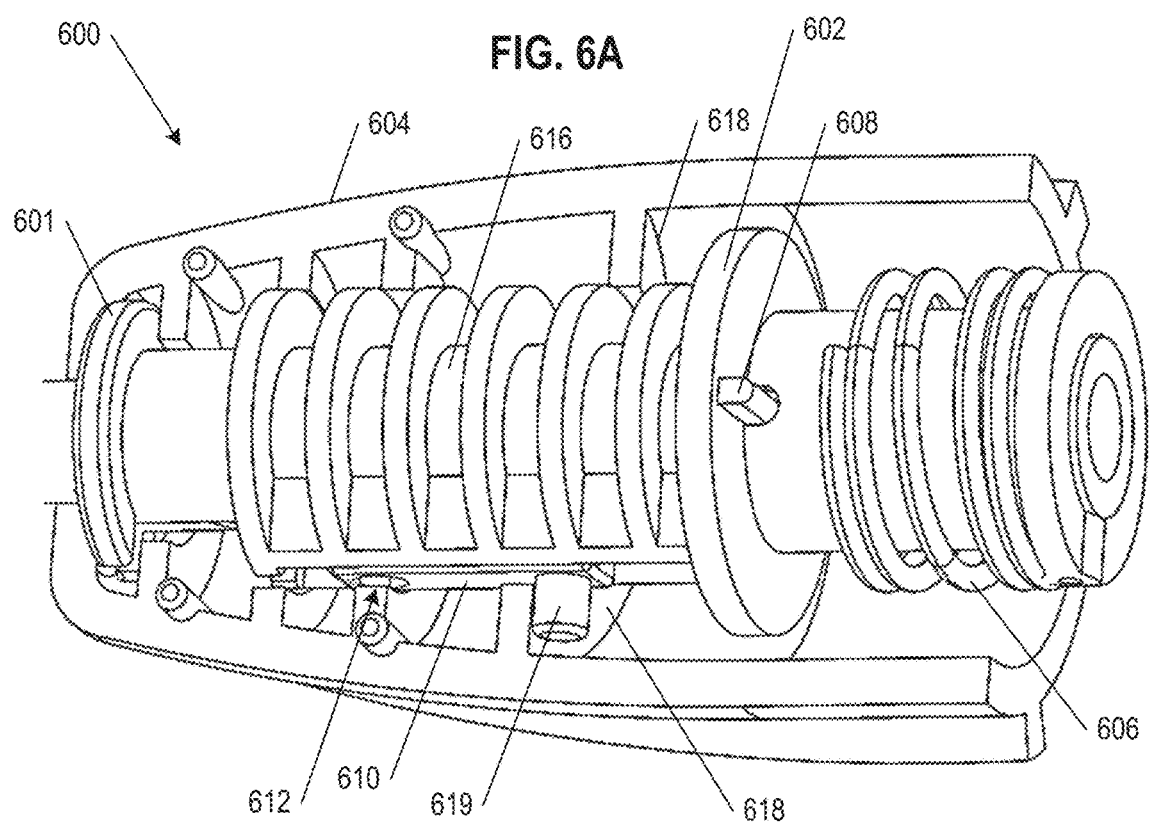
FIGS. 6A-6E show another variation of the deflection mechanism, where the first flange is coupled to the adjustment knob.
Figure 6B:
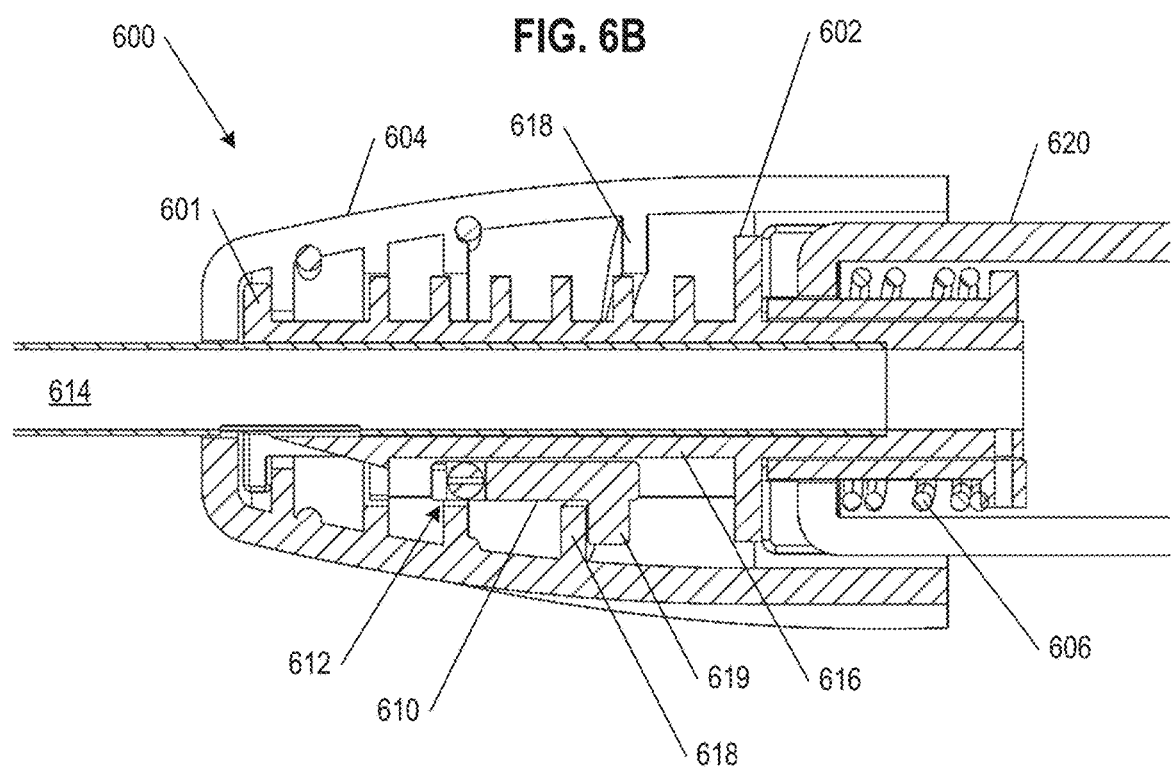

Referring to FIGS. 6A, 6B (a cross-sectional view of FIG. 6A with handle removed), and 6E, deflection mechanism (600) has a first flange (602), an adjustment knob (604), a spring (606), and rotational lock (608). The pullwire (not shown) exits the proximal end of the applicator (614) to connect with a cam follower (610) via a ball and socket type securement (612), as described for FIGS. 3A and 3B. A shoulder (601) is configured to mate with a groove/notch in the knob to axially fix the knob (604) to the first flange (602), but allow rotation of the knob (604) with respect to the first flange (602). The knob (604) includes a ramp or cam surface (618) that mates with the peg (619) on the cam follower (610). As the knob (604) is rotated with respect to the first flange (602) (and also with respect to the handle (620)), the cam follower (610) is actuated axially (in a proximal direction) by the cam surface (618), which thereby deflects the distal end of the applicator (614). The cam follower (610) sits within a follower guide (616) that allows for the linear translation of the cam follower (610) as the knob (604) turns and moves the peg (619) along the cam surface (618). The pullwire, its proximal end being secured to the cam follower (610) by the securement (612), moves linearly along with the cam follower (610) and causes the distal end of the pullwire to pull on the distal tip of the applicator (614), thereby bending the distal tip to change the distal tip angle and orientation.

The pitch of the ramp or cam surface may determine how much rotation is required to deflect the tip to a predetermined degree of deflection. For example, the pitch of the ramp may be designed such that 360 degrees of knob rotation corresponds to a maximum of 120 degrees of tip deflection and any desired tip angle between zero degrees and 120 degrees may be achieved by rotating the knob between zero degrees and 360 degrees. Alternatively, the pitch may be designed such that 720 degrees of knob rotation corresponds to a maximum of 120 degrees of tip deflection and any desired tip angle between zero degrees and 120 degrees may be achieved by rotating the knob between zero degrees and 720 degrees. In this variation, rotation of the knob would be configured to only control tip deflection, unlike other variations described herein where rotation of the knob simultaneously controls tip deflection and rotational orientation of the tip. However, as previously stated, depending on the target tissue site, the applicator distal end may be deflected to a deflection angle of about 10 degrees, about 20 degrees, about 30 degrees, about 40 degrees, about 50 degrees, about 60 degrees, about 70 degrees, about 80 degrees, about 90 degrees, about 100 degrees, about 110 degrees, or about 120 degrees. In some variations, the deflection angle may be greater than 120 degrees.

Figure 6C:
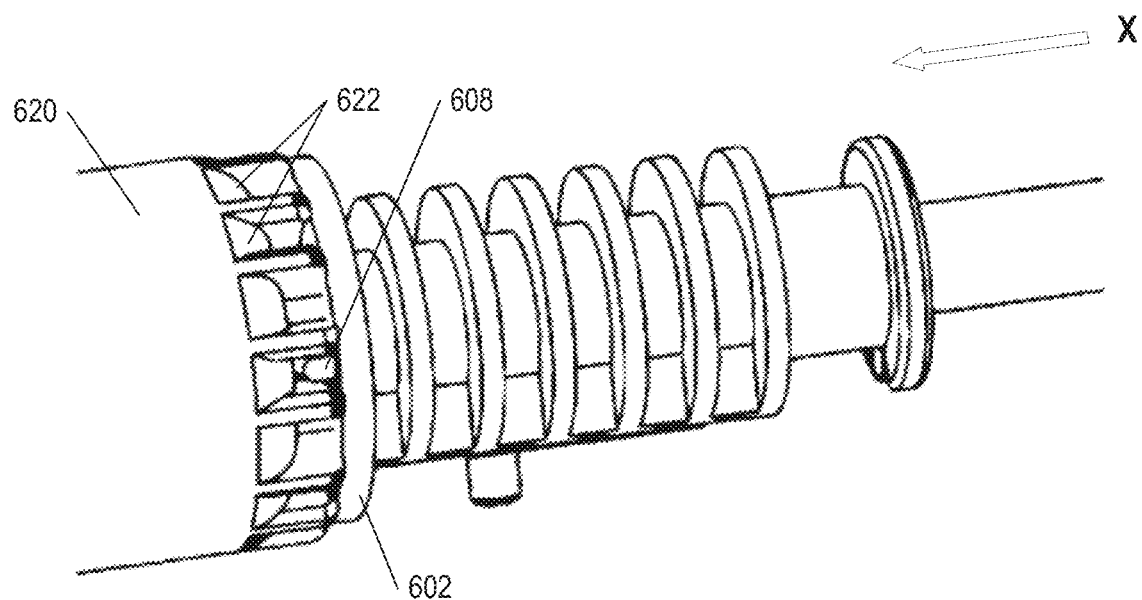
Figure 6D:
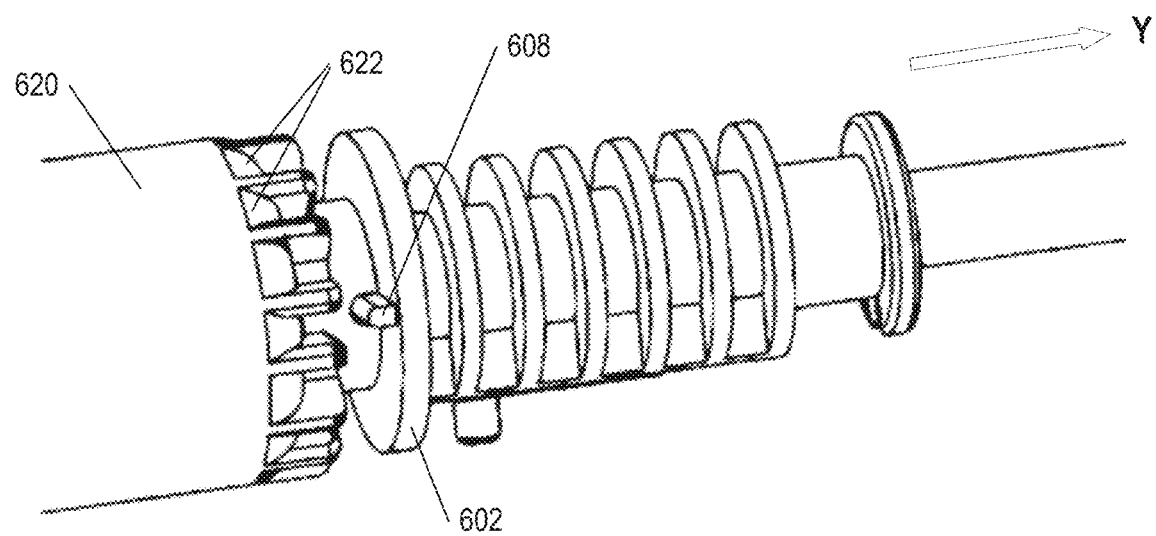
Figure 6E:
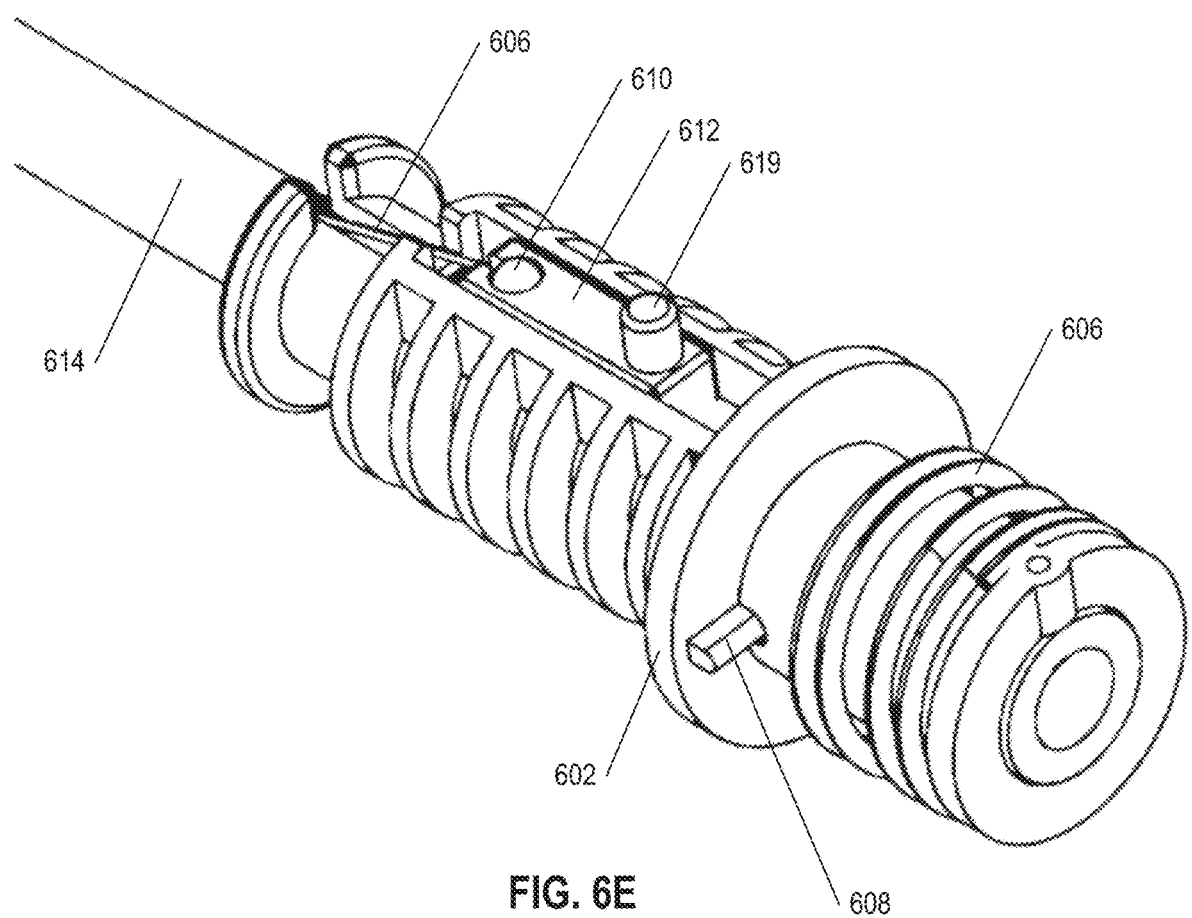

Referring to FIGS. 6C and 6D, the deflection mechanism (600) may also include a spring (606) that works in conjunction with a rotational lock such as pin (608) to bias the first flange (602) against the handle (620) and lock the rotational position of the first flange (602), which then locks the tip orientation with respect to the handle (620). The pin (608) aligns with corresponding structures in the handle, e.g., notches (622), so that when the adjustment knob (604) is pulled proximally in the direction of arrow (X), the first flange (602) is also pulled proximally such that pin (608) engages a notch (622) to thereby lock the rotational position of the adjustment knob (604) and axial position of the pullwire. To unlock or release the rotational position, the adjustment knob (604) may be pulled distally in the direction of arrow (Y) to disengage the pin (608) from the notch (622) of the handle (624) so that it can be rotated again to readjust the axial position of the pullwire and the deflection angle of the applicator.

Locking and unlocking of the first flange may be repeated depending on the number of times the system is used to access various target tissue sites. The rotational lock may lock rotation of the first flange with respect to the handle to provide a suitable orientation of the tip with respect to the handle. Similar to the aforementioned variations, the pullwire may be retracted to deflect the angle of the applicator distal end from 0 degrees to approximately 120 degrees. For example, the applicator distal end may be deflected to a deflection angle of about 10 degrees, about 20 degrees, about 30 degrees, about 40 degrees, about 50 degrees, about 60 degrees, about 70 degrees, about 80 degrees, about 90 degrees, about 100 degrees, about 110 degrees, or about 120 degrees. In some variations, the deflection angle may be greater than 120 degrees. The physician may stop rotating the adjustment knob once they are satisfied with the deflection angle. In other variations, once the desired deflection angle is achieved, the applicator may be pulled away from the handle to unlock the orientation of the distal end of the applicator with respect to the handle and rotated in 45 degree increments. At 45 degree increments, the applicator would click back into the handle to lock the orientation of the applicator with respect to the handle.

Further variations of the deflection mechanism include a first flange coupled to a second flange, which in turn is coupled to a ratchet assembly for retracting the pullwire. Here the first flange is fixedly attached to the applicator, and the second flange concentrically disposed about, and rotationally coupled to, the first flange so that it can translate proximally and distally along the axis of the first flange to effect applicator deflection, as further described below. The first flange may be fixedly attached to the applicator via adhesive bonding, or the first flange and applicator injection molded together as a single component. It is understood that these two components may be secured together in other ways. An adjustment knob secured to the first flange may be rotated to effect rotation of the first flange so that the applicator distal end will be oriented as desired once the pullwire is retracted. The ratchet assembly, which in part is connected to both the second flange and the housing of the handle, may be used to pull back the pullwire with the use of a trigger and lock it at a desired axial position. A release lever of the ratchet assembly may also be articulated to unlock or release the axial position of the pullwire.

Figure 7A:
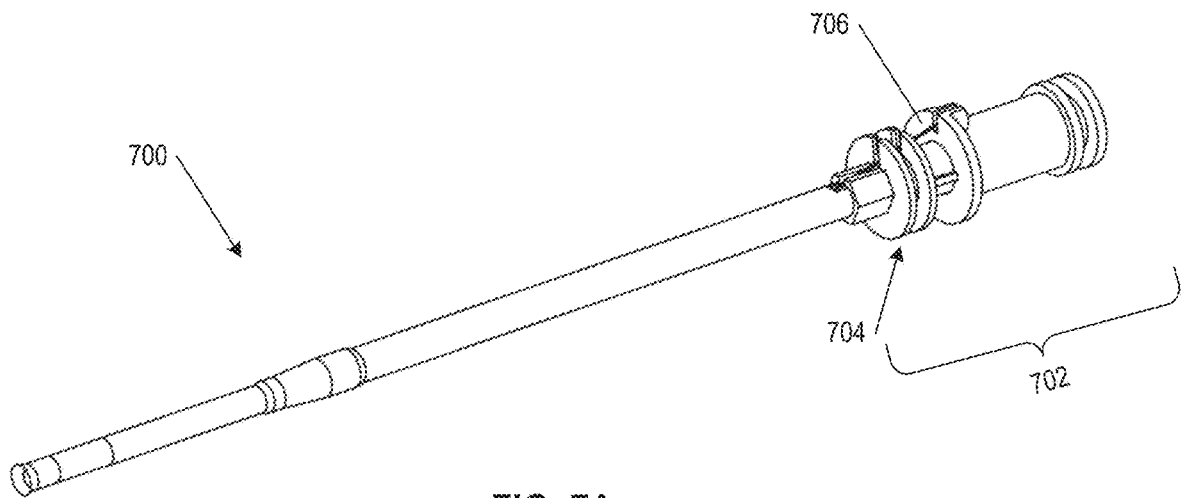
FIGS. 7A-7F depict a further variation of the deflection mechanism, where the first flange is coupled to a second flange and ratchet assembly.
Figure 7B:
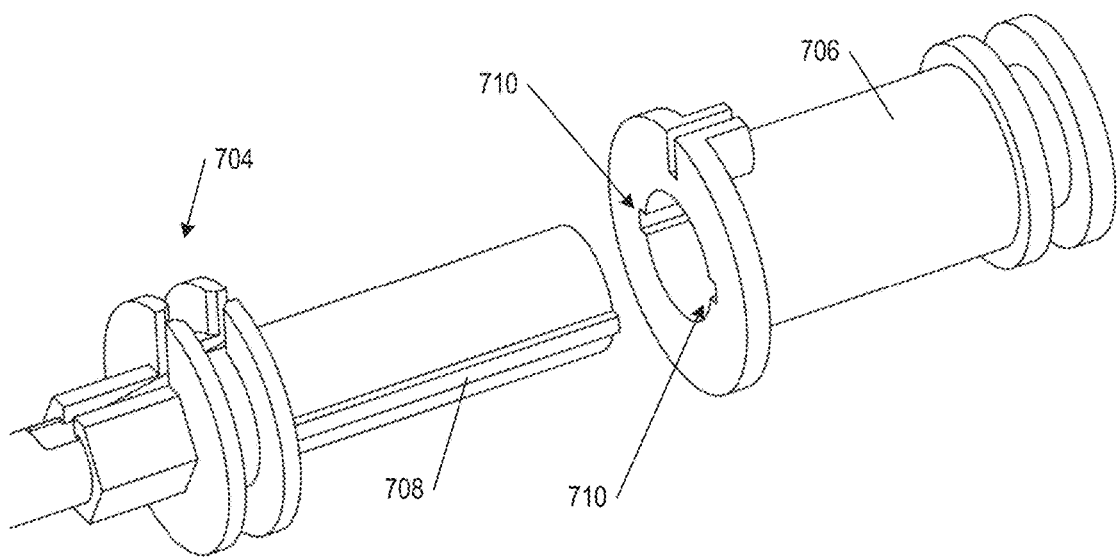
Figure 7C:
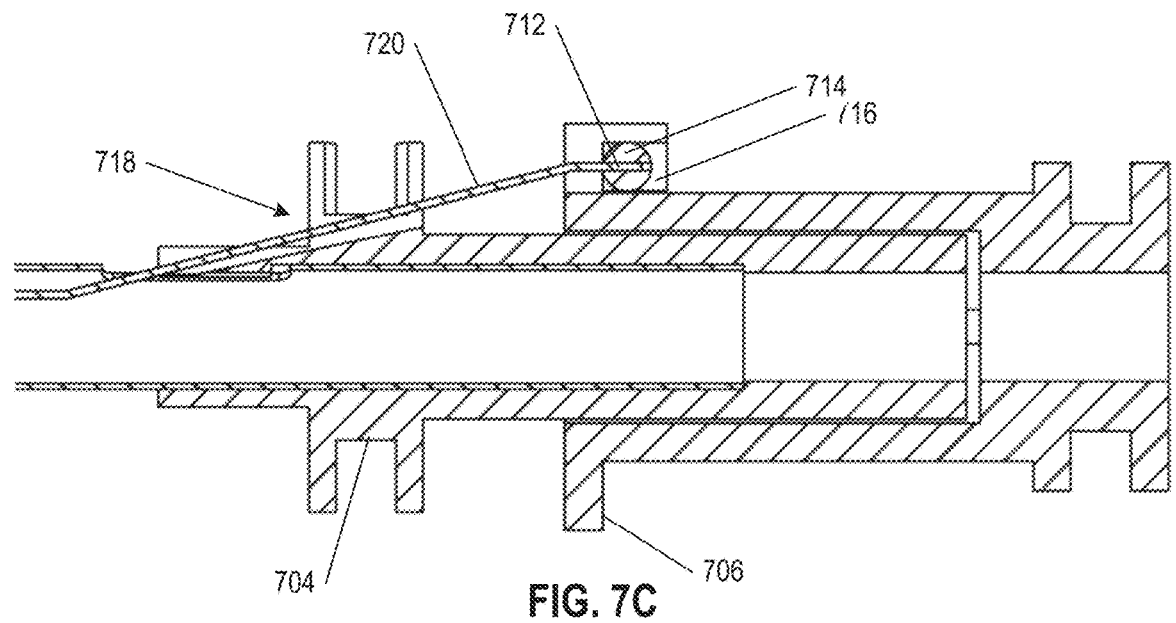
Figure 7D:
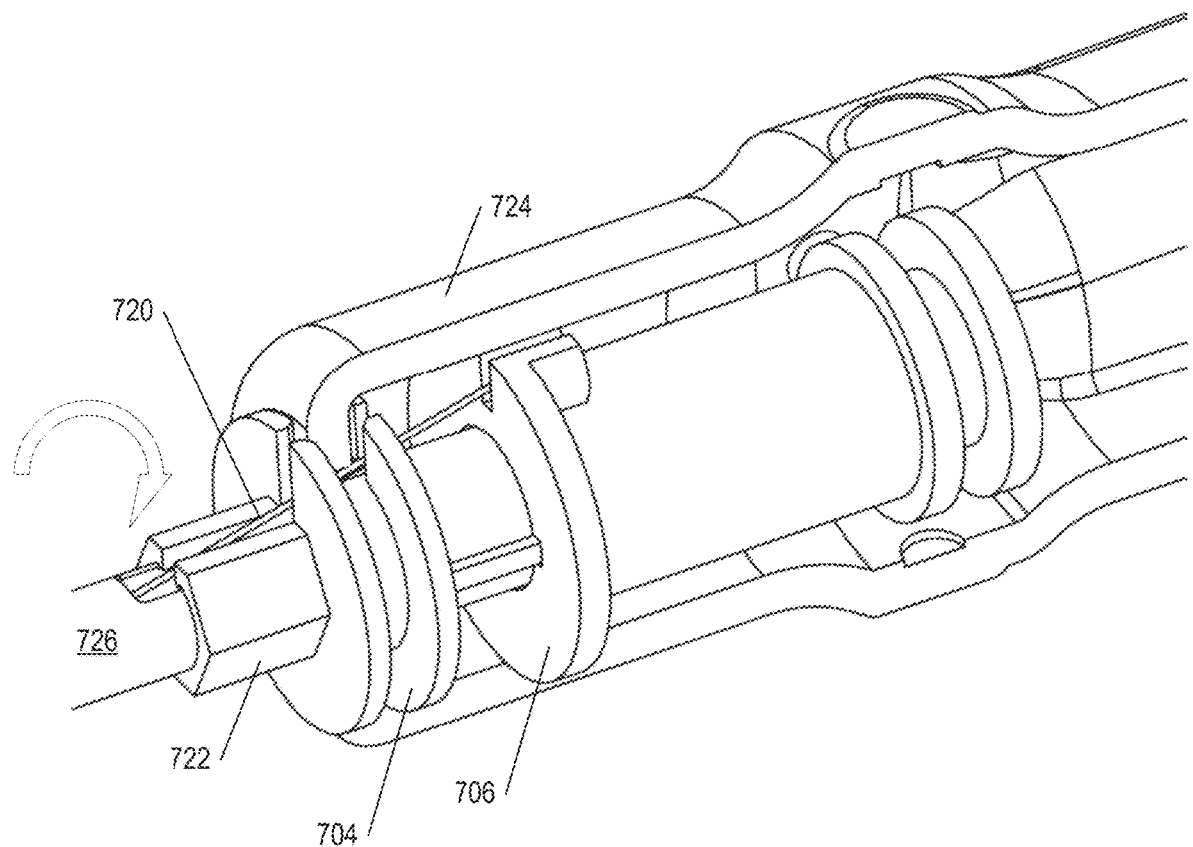

For example, referring to FIG. 7A, the deflection mechanism (702) of system (700) may include a first flange (704) and a second flange (706). Although the first flange (704) and the second flange (706) may be coupled together in any suitable manner, in some variations, as shown in FIG. 7B, ribs (708) on the first flange (704) are configured to fit into corresponding grooves (710) of the second flange (706). Any suitable number of ribs and grooves may be employed to couple the flanges. As seen in FIGS. 7C and 7D, use of the rib and groove arrangement keeps the first and second flanges rotationally fixed to one another so that rotation of an adjustment knob (not shown) rotates both the first and second flanges with respect to the handle (724), and appropriately orients the applicator distal end to the target tissue anatomy. Referring to FIG. 7D, an adjustment knob (not shown) may be press fit or otherwise fixedly secured to a fitting (722) of the first flange (704) at the proximal end (726) of the applicator. Although the fitting (722) is shown as being hexagonal in shape, it is understood that the fitting may have any suitable shape and geometry. Rotation of the adjustment knob (direction indicated by the arrow) rotates the first flange (704) and the second flange (706) with respect to the handle (724). The adjustment knob may be rotated to any suitable degree to appropriately orient the distal end of the applicator.

Similar to other variations, a pullwire attached at one end to the distal tip of the applicator may exit though an opening provided in the applicator proximal end. However, when a second flange is employed, the proximal end (712) of the pullwire (720) travels through slots (718) of the first flange (704) to attach to a ball (714), which sits within a pocket (716) disposed on the second flange (706), as shown in the cross-sectional view of FIG. 7C. With this configuration, proximal movement of the second flange (706) pulls back the pullwire (720), which in turn deflects the distal end of the applicator (not shown).

Figure 7E:
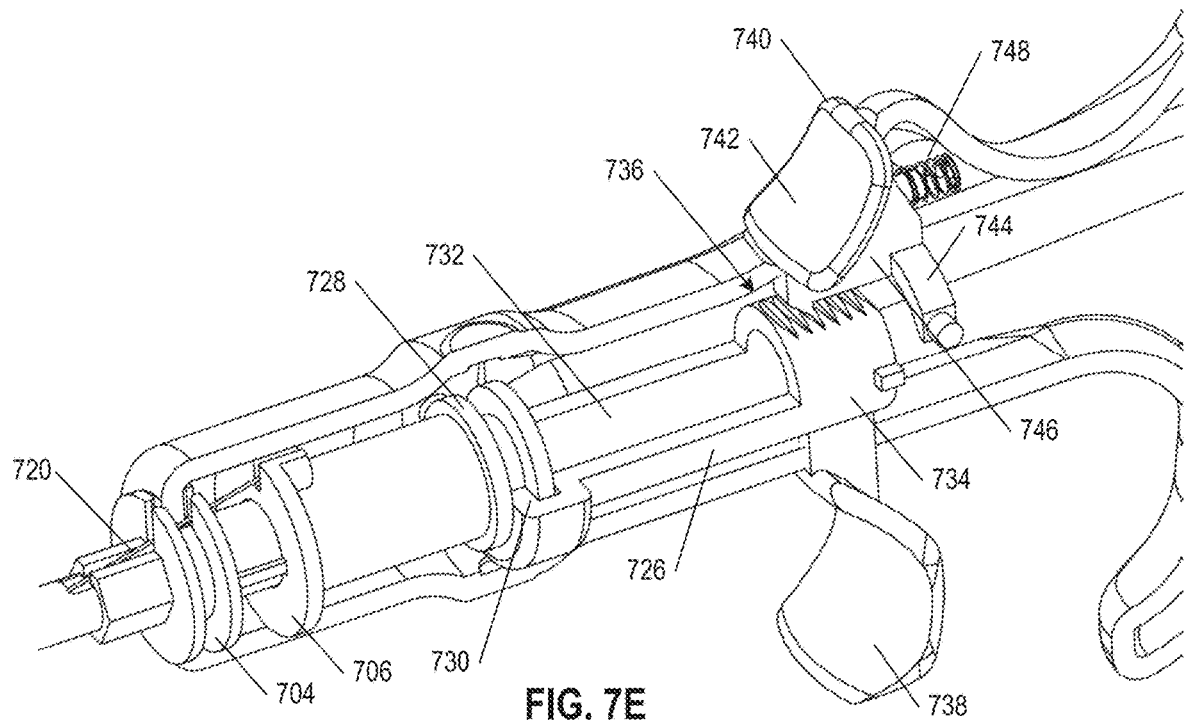
Figure 7F:
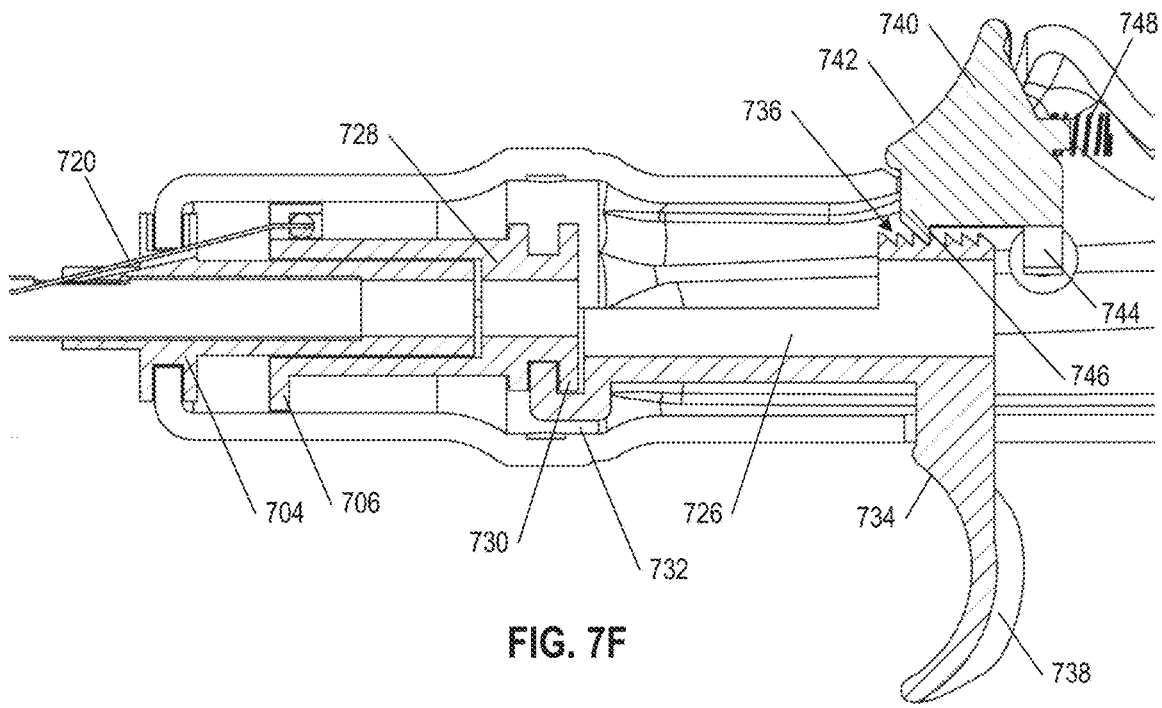

The second flange may be coupled to a ratchet assembly that provides axial movement of the second flange and positional locking thereof. For example, as illustrated in FIGS. 7E and 7F, second flange (706) may be connected to a ratchet assembly (726). The proximal end of the second flange includes a bobbin-like structure (728) that fits into a corresponding groove (730) provided on the distal end (732) of the ratchet assembly (726). The proximal end (734) of the ratchet assembly (726) includes teeth (736) and a trigger (738), which runs along a longitudinal slot provided in the handle. Accordingly, once the orientation of the applicator distal end is set by rotating the adjustment knob, to retract the pullwire (720) and deflect the distal end of the applicator, trigger (738) is pulled proximally, using for example, an index finger, to retract the ratchet assembly (726) and second flange (706). The trigger may be used to retract the pullwire and generate a deflection angle at the applicator distal end from a starting point of 0 degrees, to approximately 120 degrees. For example, the applicator distal end may be deflected to a deflection angle of about 10 degrees, about 20 degrees, about 30 degrees, about 40 degrees, about 50 degrees, about 60 degrees, about 70 degrees, about 80 degrees, about 90 degrees, about 100 degrees, about 110 degrees, or about 120 degrees. In some variations, the deflection angle may be greater than 120 degrees.

When a ratchet assembly is employed, the axial position of the pullwire, and thus the deflection angle of the applicator, may be locked and unlocked. Referring back to FIGS. 7E and 7F, a release lever (740) may be provided with the handle that includes a pad (742), a pivot (744), and a pawl (746). In use, the trigger (738) may be pulled back to disengage the pawl (746) from the teeth (736) of the ratchet assembly (726). As the trigger (738) is pulled proximally, the pad (742) rotates to engage with the next tooth of the ratchet assembly (736). The pad (742) of the release lever (740) may be depressed to release the second flange (706) and bring the deflection angle back to zero. A lever spring (748) may be disposed behind the release lever (740) to create a biasing force that aids with disengagement. Engagement and disengagement of the pawl from the teeth of the ratchet assembly may occur any number of times to achieve and lock/unlock the appropriate deflection angle.

It can be appreciated that the adjustable knob structure and assembly as described herein can be implemented on a wide range of delivery systems for altering the angle or orientation of a coupled distal tip. In particular, delivery systems configured to implant self-expandable devices (e.g., stents) into a nasal, otic, or throat cavity can be configured to include an adjustment knob that changes the angle or orientation of the distal end of the delivery device, allowing for deployment of a self-expanding device at specific angles (relative to the delivery device) so as to more effectively deploy at or within target anatomies. In such implementations, the distal tip portion of the assembly may be further coupled with a section of the device or sheath that can be withdrawn or pulled in a proximal direction (i.e. pulled back toward the handle or proximal end of the delivery system) at any functional angle or orientation of the distal tip.

Referring back to FIG. 2B, applicator (202) may be reinforced with braiding (222) to prevent kinking of the applicator during steering or deflection. The applicator may have any suitable inside diameter for passage of a device. For example, the inner diameter may range from about 2.0 mm to about 3.0 mm. In some instances, the inner diameter may be about 2.0 mm, about 2.1 mm, about 2.2 mm, about 2.3 mm, about 2.4 mm, about 2.5 mm, about 2.6 mm, about 2.7 mm, about 2.8 mm, about 2.9 mm, or about 3.0 mm. Additionally, the length of the applicator may range from about 9 cm to about 16 cm. The applicator may be formed from materials including, but not limited to, stainless steel, polyether ether ketone (PEEK), a Pebax® elastomer, Nylon polymers, polyethylene, etc.

Figure 8A:
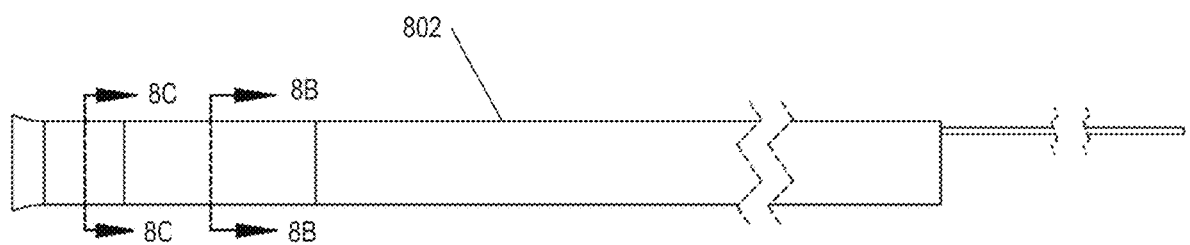
FIGS. 8A-8C depict an exemplary applicator including features for minimizing drug loss upon device deployment.
Figures 8B, 8C:
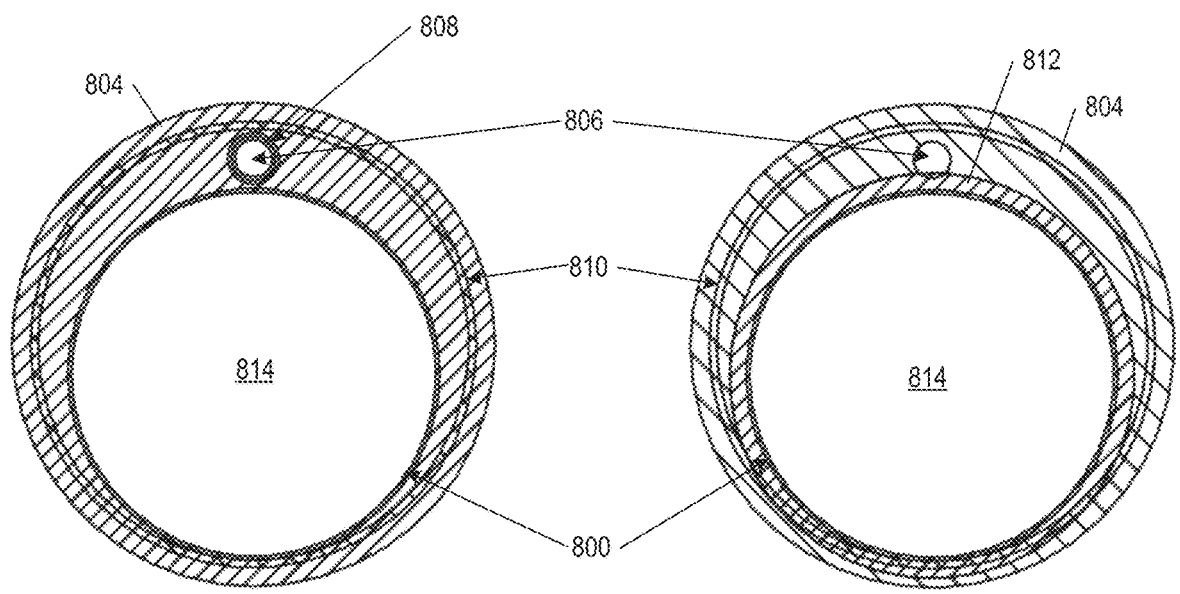

When a drug coating is provided, any suitable drug may be used. For example, the drug coating may include a corticosteroid. In some variations, the drug included in the coating may include a corticosteroid such as mometasone furoate or pharmaceutically acceptable salts, solvates, hydrates, esters, free bases, enantiomers, racemates, polymorphs, amorphous, or crystal forms thereof. In other variations, the corticosteroid is fluticasone, or a pharmaceutically acceptable salt, solvate, hydrate, ester, free base, enantiomer, racemate, polymorph, amorphous, or crystal form thereof. Furthermore, when a drug coating is provided, the device lumen (214) may be made from a lubricious material such as ethylene chlorotrifluoroethylene (ECTFE), ethylene tetrafluoroethylene (ETFE), fluorinated ethylene propylene (FEP), PEBAX elastomer, polytetrafluoroethylene (PTFE), silicone polymers such as Everglide® silicone polymer, or combinations thereof, to protect the drug coating on the expandable device. Alternatively, the lubricious polymers may be layered or coated onto the device lumen. An exemplary lubricious coating (800) of a device lumen (814) is shown in FIGS. 8B and 8C, which are cross-sectional views of the applicator (802) taken along lines 8B-8B (FIG. 8B) and 8C-8C (FIG. 8C). FIGS. 8B and 8C also show cross-sectional views of various system components and their positional relationship to one another within the wall (804) of the applicator (802). The components running through the applicator include a single pullwire (806), a pullwire lumen (808), reinforcing braid (810) that helps prevent kinking of the applicator when deflected, and a metal o-ring (812) to which the pullwire (806) is secured, e.g., by soldering, welding, etc. In some aspects, the reinforced braid (810) can be a reinforced coil.

The devices are generally advanced over a guidewire. A finger slide coupled to the housing of the handle may also be coupled to a guidewire so that movement of the finger slide along an elongate slot in the handle advances or retracts the guidewire with respect to the handle. The finger slide typically has a travel length ranging from about 5 cm to about 16 cm. The use of a finger slide may result in improved ergonomics, and allow for greater advancement of the guidewire. An exemplary finger slide (218) is shown in FIGS. 2A and 2C.

Figure 9A:
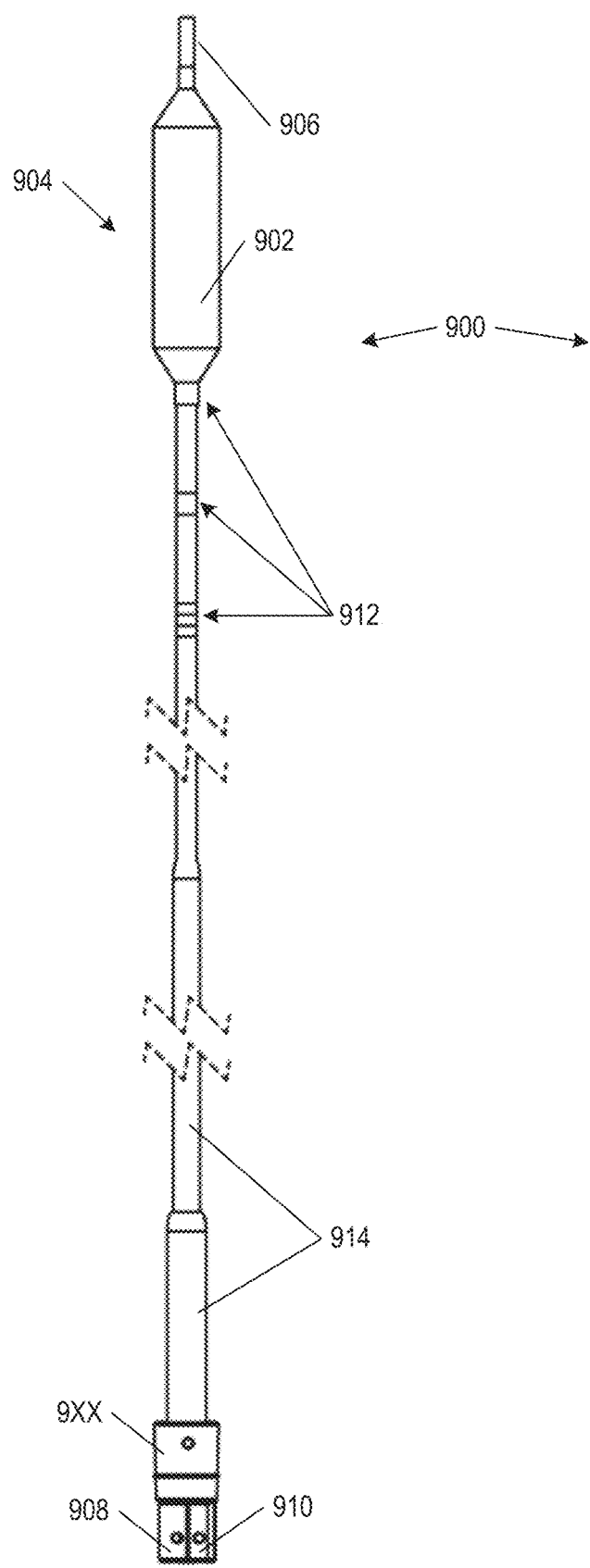
FIGS. 9A and 9B show an exemplary balloon catheter for use with the disclosed systems.
Figure 9B:
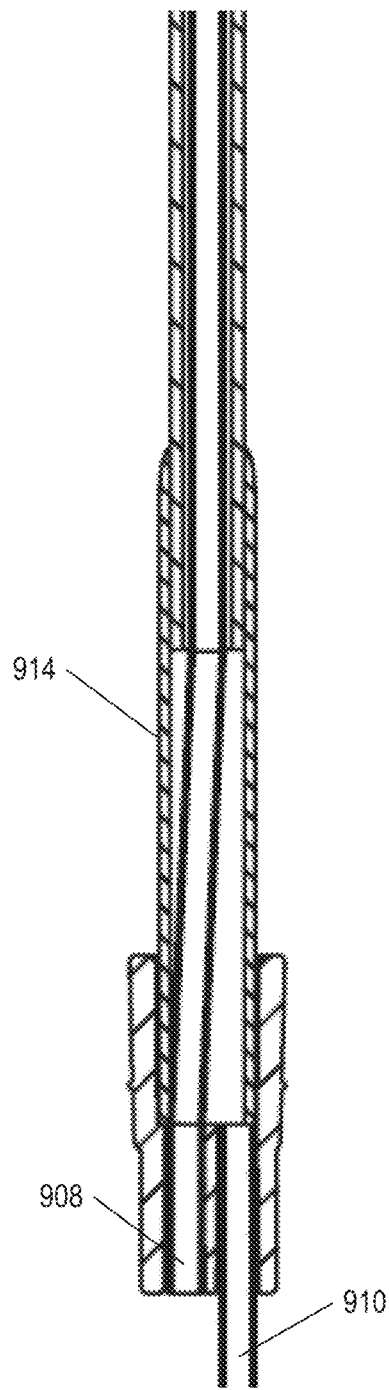

When the device to be advanced is an expandable balloon, the balloon catheter may also be configured with a reduced profile to reduce the entire profile of the applicator and handle. For example, as illustrated in FIGS. 9A and 9B, balloon catheter (900) includes an expandable balloon (902) measuring 6 mm by 20 mm at its distal end (904) and having a soft distal tip (906). The guidewire lumen (908) and balloon inflation lumen (910) are juxtaposed to minimize the outside diameter of the balloon catheter (900). The outside diameter of the balloon catheter may range from about 5 mm to about 7 mm, for example, the outside diameter may be about 5 mm, about 6 mm, or about 7 mm. In other variations, for example when treating throat conditions, the outside diameter of the balloon catheter may range from about 5 mm to about 16 mm, for example, about 5 mm, about 6 mm, about 7 mm, about 8 mm, about 9 mm, about 10 mm, about 11 mm, about 12 mm, about 13 mm, about 14 mm, about 15 mm, or about 16 mm. In further variations, the balloon catheter outside diameter may be larger than 16 mm. Applicator markers (912) may also be provided along the length of the balloon catheter (900) to help visualize the position of the distal catheter end with respect to the target tissue site (e.g., visualizing the device with a separate endoscope). The applicator markers (912) may be radiopaque or have a material or contrasting color that allows for direct visualization. A stiffening tube (914) may further be provided to impart greater pushing force to the catheter (900).

In some aspects, the soft distal tip (906) can extend a distance beyond the distal end of the expandable balloon (902), where the length of the distal tip (906) can be relatively shorter than the length of the expandable balloon (902). In other aspects, the balloon catheter (900) can have a length that effectively ends at the distal end of the expandable balloon (902), where the structure of a guidewire or guidewire lumen co-terminates with the expandable balloon (902), and there is not a structurally distinct distal tip extending past the expandable balloon (902). In all such aspects, the distal end of the balloon catheter (900) can be atraumatic, having a flexibility and/or durometer that is relatively compliant such that pressure applied by the distal end of the balloon catheter (900) on tissue or a sinus structure does not generally cause damage to that tissue or structure.

Figure 13:
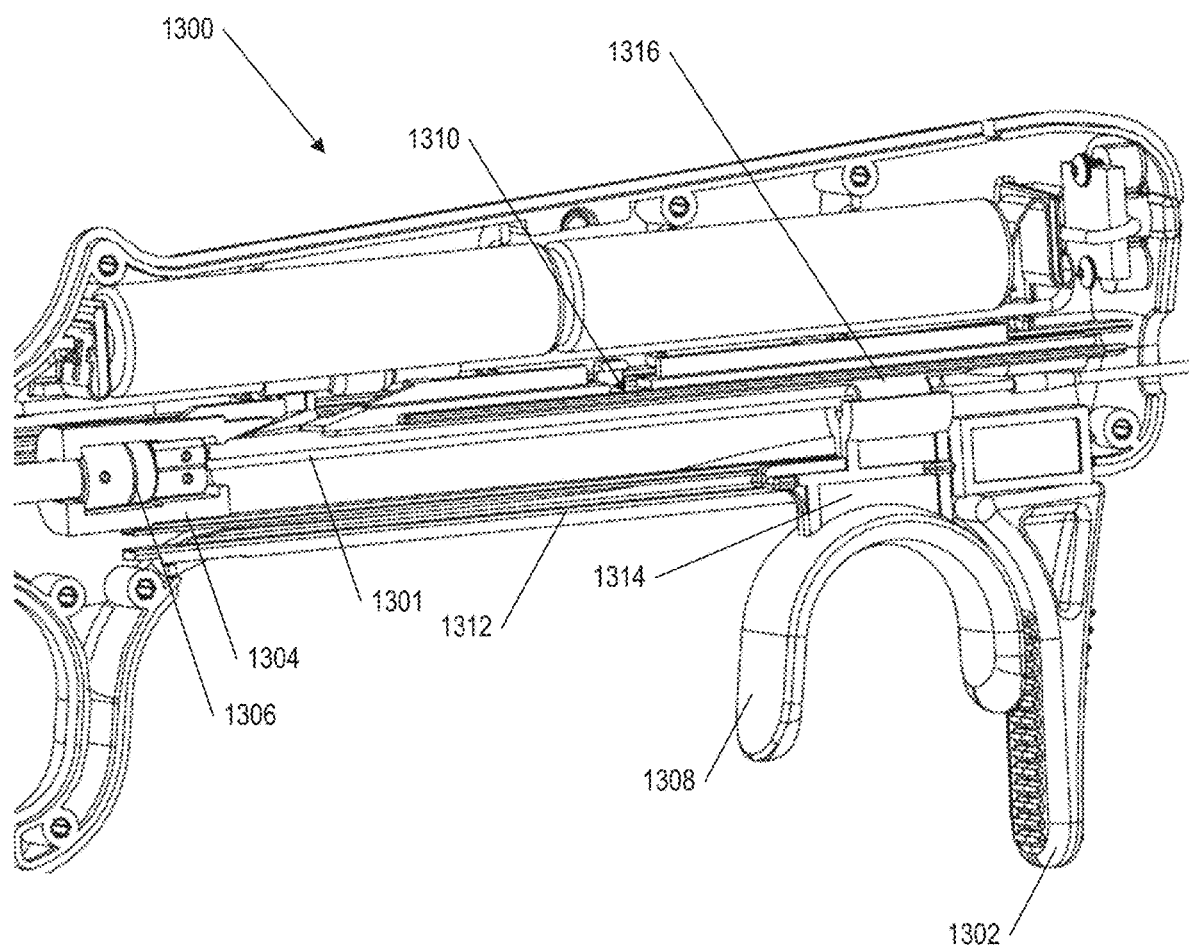
FIG. 13 depicts yet a further exemplary handle and the various components contained therein.

Referring to FIG. 13, the relationship of the balloon catheter and guidewire to each other and the mechanism of their movement is shown. Referring to the figure, a portion of a handle (1300) is illustrated including a balloon catheter hub (1306) contained within a balloon slider (1304). Tabs (1310) on the balloon slider (1304) interface with slots provided in the handle such that sliding (e.g., advancement) of a balloon actuator (1302) fixed to the balloon slider thereby slides or moves the balloon catheter hub (1306) and the rest of the balloon catheter. Prior to balloon catheter advancement, a guidewire (1301) is typically advanced by sliding advancement of a guidewire actuator (1308), and the balloon catheter then advanced over it. In the variation shown in FIG. 13, guidewire (1301) includes a bushing (1316) that interfaces with a guidewire slider (1314) on the guidewire actuator (1308). When the guidewire actuator (1308) is pushed forward (e.g., advanced) relative to the balloon actuator (1302), this movement in turn allows the guidewire slider (1314) to move along a rail (1312) of the handle (1300) and thus also move or advance the guidewire (1301).

With respect to visualization, the guidewire may or may not be capable of illumination. When illumination is to be provided, the guidewire may include an optical fiber that illuminates the position of the distal tip of the applicator and/or distal tip of the guidewire with respect to the target tissue site or area to be treated (e.g., a sinus). In some instances, light may be transmitted to the distal tip of the applicator and/or distal tip of the guidewire by a light tube or pipe instead of an optical fiber. The illumination may be visible from outside the patient.

In some variations, the illuminating guidewire ("lightwire") includes the structure depicted in FIGS. 10A and 10B. Referring to the figures, lightwire (1000) includes an optical fiber (1002) that extends through a lumen of a hypotube (1004). Although the optical fiber (1002) is shown as being secured to the hypotube by an adhesive, it is understood that their attachment is not so limited, and that they may be secured to one another in different ways. A strain relief (1008) may also be provided over the area of attachment to help protect it from forces applied during advancement and retraction, e.g., pushing, pulling, rotation, etc. A bushing (1007) can be provided to mate with a guidewire actuator. In addition, a metal coil (1006) may be concentrically disposed about the distal end (1010) of the lightwire (1000) to impart sufficient rigidity as well as flexibility to that portion of the lightwire (1000) useful for advancement thereof. An adhesive may be used at the distal tip (1012) of the lightwire (1000) to hold the coil (1006) in place. Instead of an adhesive, a soft polymer or other atraumatic feature may be disposed on the distal tip (1012).

The systems may include a built-in light source for the lightwire. In one variation, as shown in FIGS. 10C and 10D, the built-in light source (1014) is powered by batteries (1016). A contact, e.g., positive terminal wire (1018) may be provided for making electrical contact between the batteries and a metal core printed circuit board (1020) ("MCPCB") that provides a mounting surface for an LED (1022) lighting the optical fiber (1002). A negative terminal (1028) may be provided between the LED driver board (1020) and batteries (1016). The LED (1022) and optical fiber (1002) may be coupled to the driver board by a holder (1024) and wires (1026). A resistor (1030) connected to the circuit via wiring (1031), that controls or regulates the voltage being supplied to LED, where the resistor (1030) can have a resistance of from about one to about ten ohms (1-10Ω), and in specific implementations the resistor can have a resistance of about 2Ω or about 3Ω. In general, the LED employed will generate light in the visible spectrum, e.g., light having a wavelength between about 390 nm and about 700 nm. The systems described herein are generally configured to have a low profile, and the use of batteries or a battery pack in the device design may be useful in creating this low profile.

FIG. 10E is a cross-sectional view of the lightwire (1000) taken along the line 10E as shown in FIG. 10A. FIG. 10E further illustrates a variation where the optical fiber (1002) of the lightwire (1000) is constructed from four individual illuminating guidewires (1032), alternatively referred to as optical fibers, alongside a flexible metal core (1034), which can be, for example, a NiTi wire. These elements are bundled together in an encasement structure (1036). In some implementations, the encasement structure (1036) can be a coil structure (e.g., made of stainless steel) while in other implementations the encasement structure (1036) can be a jacket made of a polymer material. In aspects, four individual illuminating guidewires (1032) and the flexible metal core (1034) can be braided around each other to provide for an overall target strength, tension, or spring force to the lightwire (1000).

Instead of employing multiple pullwires, the systems described here can deflect the distal end of the applicator in multiple different angles while maintaining a fixed handle orientation with respect to the patient using a single pullwire. The pullwire lumen may be made from polyimide or other suitable materials. The location of the pullwire lumen (220) may be as shown in FIG. 2B. The pullwire at one end may be attached to a distal tip of the applicator via, e.g., adhesive, heat welding, or a coupling ring (e.g., metal ring (812) shown in FIG. 8C), and at the other end be directly attached to first or second flange, as described herein. Accordingly, as the adjustment knob of the system is rotated, the pullwire is pulled, and the distal end of the applicator bends to various angles. Depending on the target tissue site, the applicator distal end may be deflected to a deflection angle of about 10 degrees, about 20 degrees, about 30 degrees, about 40 degrees, about 50 degrees, about 60 degrees, about 70 degrees, about 80 degrees, about 90 degrees, about 100 degrees, about 110 degrees, or about 120 degrees. In some variations, the deflection angle may be greater than 120 degrees.

When the device is a single drug-coated balloon intended to treat multiple and/or different paranasal sinuses, it may be useful for the system to include features that help protect the coating and minimize drug loss during deployment and after withdrawal of the balloon from each paranasal sinus. Here the balloon is housed in the applicator until delivered to the next paranasal sinus. Thus, features that prevent scraping of the balloon coating against the interior or inner wall of the applicator lumen during deployment or withdrawal, or scraping of the balloon coating against the distal tip of the applicator during deployment or withdrawal may be desirable. In some variations, the distal tip of the applicator may be flared and/or angled to minimize drug loss while still maintaining a delivery profile small enough to access sinus ostia.

Figure 4A:
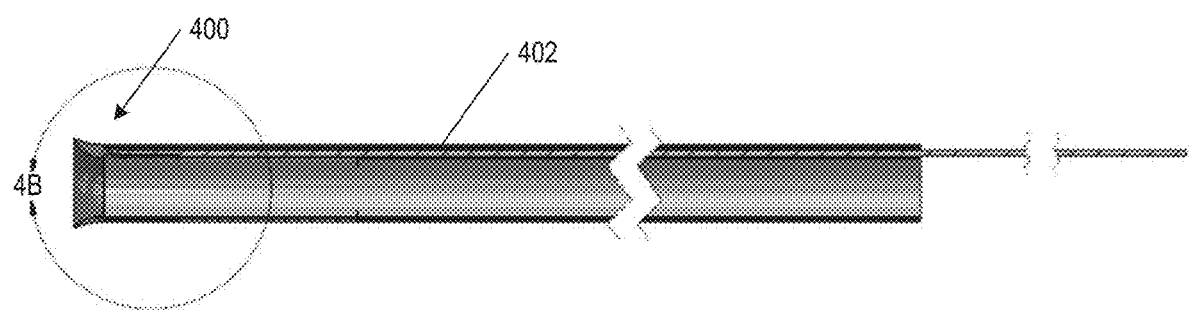
FIGS. 4A-4C depict an exemplary applicator for minimizing drug loss during balloon catheter withdrawal having a flared distal tip.
Figure 4B:
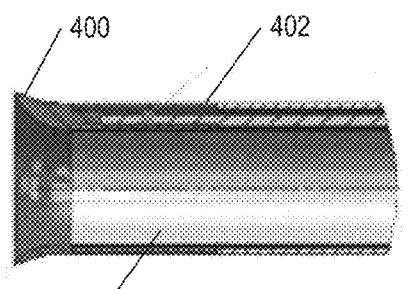
Figure 4C:
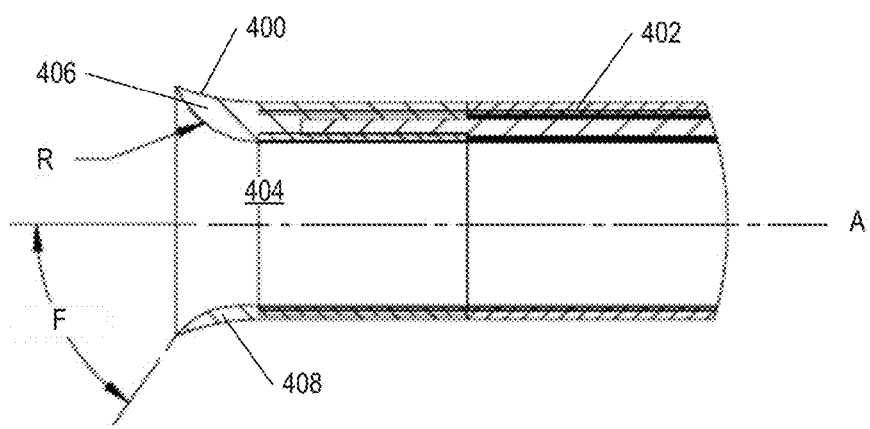

When a flared distal tip is employed, at least a first edge of the device lumen has a radius of curvature that may be useful in minimizing drug loss during device deployment. Furthermore, a second edge of the device lumen may include a flare angle tailored to minimize drug loss during device deployment. Referring to FIGS. 4A-4C, an exemplary applicator (402) having a flared distal tip (400) is shown in FIGS. 4A-4C. FIG. 4B is a detail view of the flared distal tip (400) indicated by the section 4B in FIG. 4A. In the schematic cross-sectional view provided in FIG. 4C, at least one edge (406) of the device lumen (404) has a radius of curvature (R) and a second edge (408) has a flare angle (F) with respect to the longitudinal axis (A) of the applicator (402). The radius of curvature may range from about 1.0 mm (about 0.040 inches) to about 2.54 mm (about 0.1 inches). For example, the radius curvature (R) may be about 1.0 mm, about 1.5 mm, about 2.0 mm, or about 2.5 mm. The flare angle (F) may range from about 45 degrees to about 60 degrees with respect to the longitudinal axis of the applicator. For example, the flare angle (F) may be about 45 degrees, about 50 degrees, about 55 degrees, or about 60 degrees.

In another variation, the edges of the applicator tip may be slightly rounded to prevent the drug coating from scraping off the balloon. In yet further variations, the tip of the applicator, e.g., flared distal tip (400), or the applicator lumen may be made from a lubricious material that does not react with the drug coating. Exemplary lubricious materials include without limitation, Pebax® elastomers blended with Everglide® ultra-high molecular weight silicone polymer ("Everglide blended"), ethylene tetrafluoroethylene (ETFE), fluorinated ethylene propylene (FEP), ethylene chlorotrifluoroethylene (ECTFE), perfluoropolyether synthetic oil, polytetrafluoroethylene (PTFE), perfluoroalkoxy alkane (PFA), polyvinylidene fluoride (PVDF), polyether ether ketone (PEEK), and combinations thereof. As illustrated in Example 1, use of an Everglide blended applicator resulted in approximately 1000 μg less drug loss with a single balloon inflation and deflation cycle as compared to a commercially available applicator. Instead of being made from a lubricious material, the tip of the applicator or the applicator lumen may be coated with a lubricious material such as polyethylene glycol, polyvinylpyrrolidone based cross-linked polymers, or ether based hydrophilic urethanes, parylene vapor deposition coatings, or combinations thereof.

Controlled inflation and deflation of the balloon when deployed within the head cavity of a patient is of value to ensure both that the balloon inflates to a target pressure for delivery of the therapy and to quickly deflate and reduce the balloon profile for ease of removal following delivery of therapy. Shown in FIGS. 14A-14F is a specialized structure and assembly, colloquially referred to as an "indeflator", that provides for such controlled inflation and deflation of a balloon through a coupled fluid line. In this structure, a plunger moving through a syringe barrel is coupled to a locking structure that allows the indeflator to drive fluid to an expandable member to reach a target pressure and then to lock the plunger in place along the length of the syringe. By stopping the movement of the plunger, the coupled expandable member will not be overinflated with fluid above a target pressure.

Figure 14A:
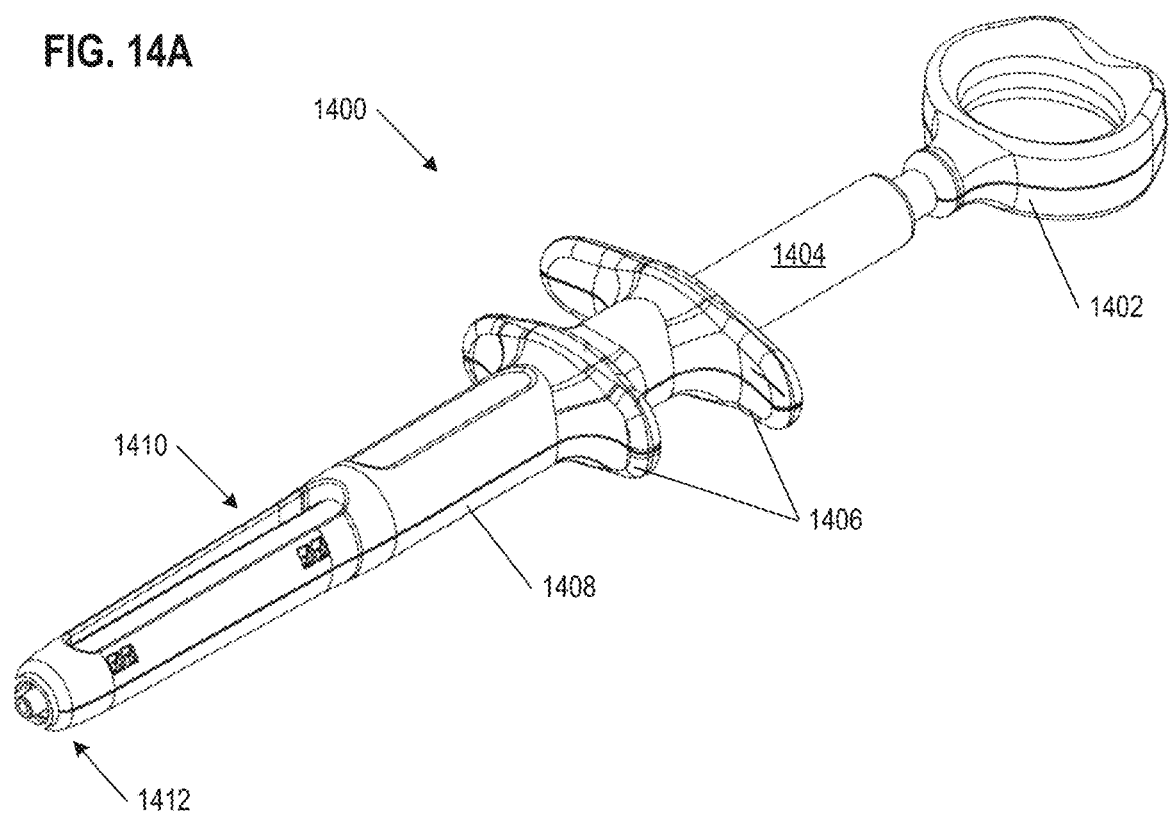
FIGS. 14A-14F depict an exemplary inflation and deflation assembly that can be used with systems for accessing anatomical structures of the present disclosure.
Figure 14B:
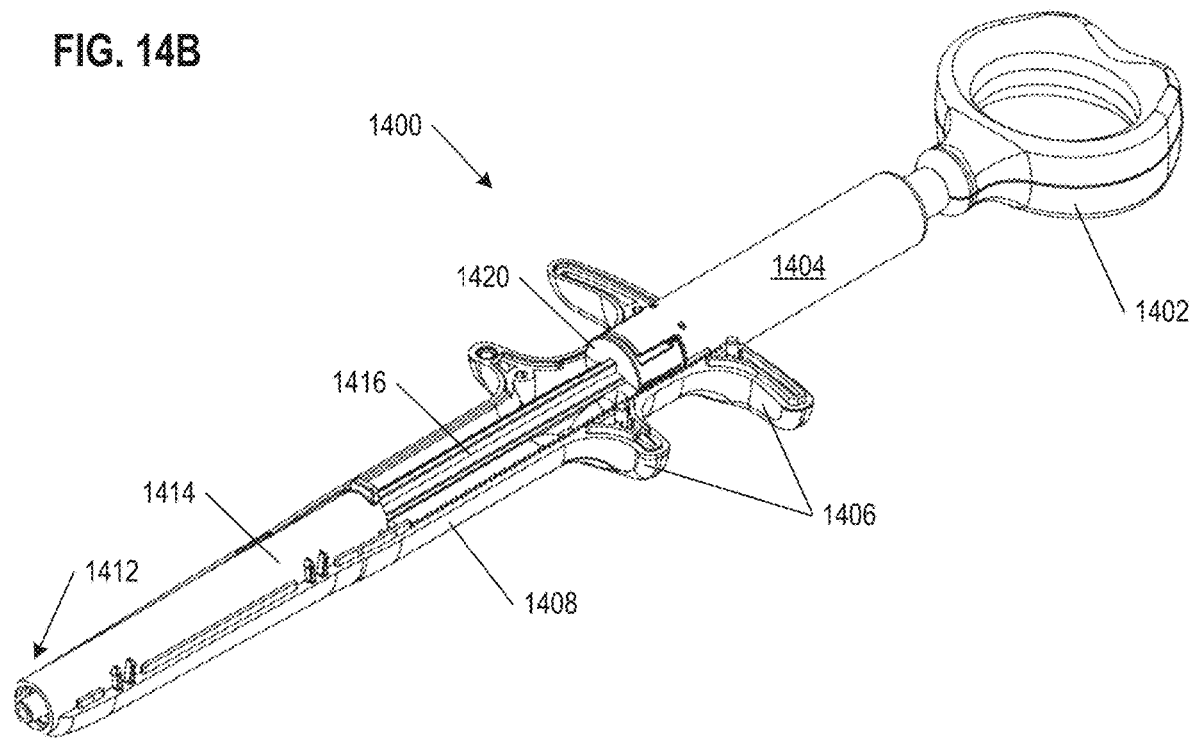

FIG. 14A illustrates a perspective view of the indeflator (1400), and FIG. 14B presents the same view with a portion of the housing removed in order to show internal components of the indeflator (1400). A driving ring (1402) is located at the back or proximal end of the indeflator (1400), providing a location where force can be applied through a plunger (1416) into a syringe barrel (1414). A piston cylinder (1404) mechanically connected to the plunger (1416) can be moved by the driving ring (1402) into or out of the shell housing (1408). Resting anchors (1406) provide a location for an operator to hold the indeflator while applying force via the driving ring (1402). The shell housing (1408) surrounds the syringe barrel (1414), as well as portions of the plunger (1416) when the plunger (1416) is at least in part depressed into the syringe barrel (1414). The shell housing (1408) can include a window (1410) to allow for visualization of fluid in the syringe barrel (1414) before during or after depression or withdrawal of the plunger (1416). A connection port (1412) allows for connection of the indeflator (1400) to fluid conduit tubing or the like in order to couple with a paired device, for example, an applicator device having a dilation member. It should be understood that an indeflator (1400) as shown herein can couple with a variety of devices that are (at least in part) operated by hydraulic pressure and be used to deliver and withdraw fluid from such devices.

The interior of the indeflator (1400) further illustrates the arrangement of the syringe barrel (1414), the plunger (1416), and a locking assembly (1420), where the locking assembly (1420) is configured to move and lock within a relatively narrow region within the shell housing (1408) while the piston cylinder (1404) and plunger (1416) move longitudinally through the shell housing (1408).

Figure 14C:
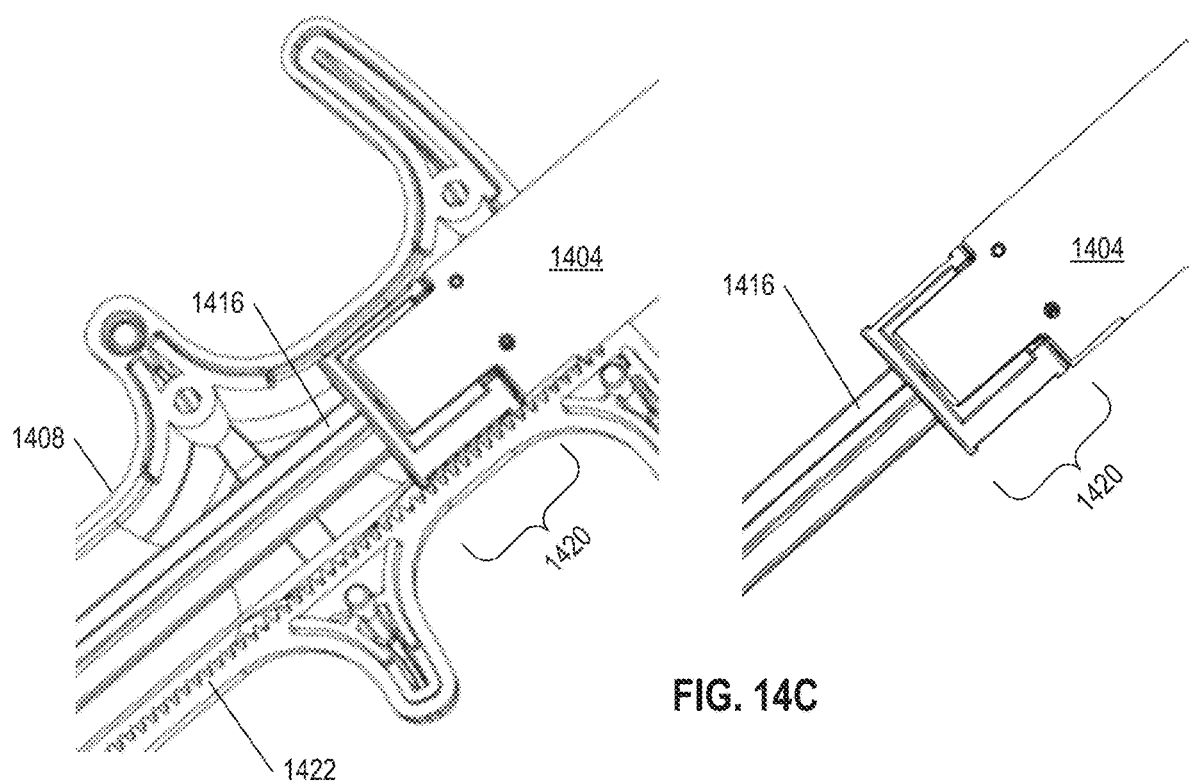
Figure 14D:
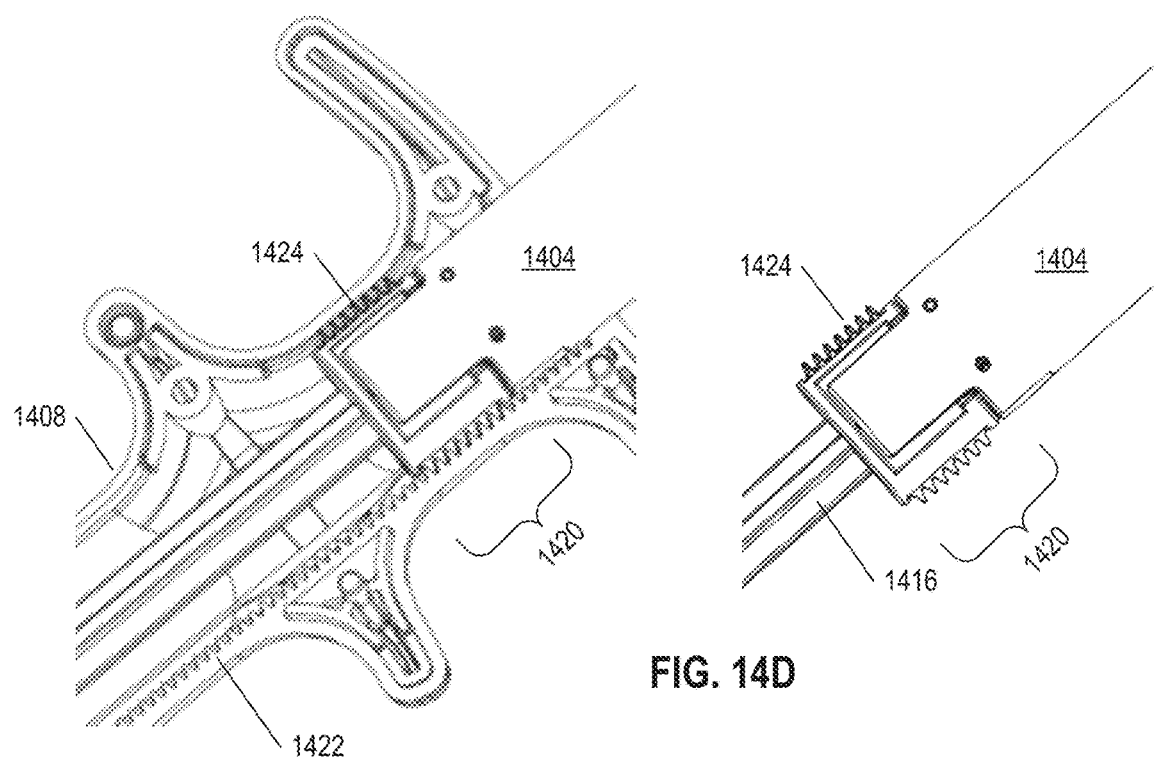

FIG. 14C is a pair of illustrations depicting a detail view of the locking assembly (1420) in a first, unlocked configuration. FIG. 14D is a pair of illustrations depicting a detail view of the locking assembly (1420) in a second, locked configuration. The left-hand illustration of FIG. 14C shows the piston cylinder (1404), locking assembly (1420), and plunger (1416) as arranged within the shell housing (1408). The right-hand illustration of FIG. 14C shows the piston cylinder (1404), locking assembly (1420), and plunger (1416) in isolation. Wall teeth (1422) (alternatively referred to as "rails") are located along an interior wall of the shell housing (1408), where the wall teeth (1422) are present at least in the operational region of the locking mechanism (1420). In some aspects, as illustrated, the wall teeth (1422) elements can have a curved structure. In the first, unlocked configuration, teeth on pawls (not shown) of the locking mechanism (1420) are fully withdrawn and within the housing of the locking mechanism (1420), thus allowing for longitudinal movement of the piston cylinder (1404) and plunger (1416) along the length of the shell housing (1408) in the distal direction.

The left-hand illustration of FIG. 14D shows the piston cylinder (1404), locking assembly (1420), and plunger (1416) as arranged within the shell housing (1408). The right-hand illustration of FIG. 14D shows the piston cylinder (1404), locking assembly (1420), and plunger (1416) in isolation. In the second, locked configuration, the pawl teeth (1424) on pawls of the locking mechanism (1420) are pushed out laterally and are sufficiently extended past the housing of the locking mechanism (1420), such that the pawl teeth (1424) interface with the wall teeth (1422) and thereby lock and stop further distal movement of the piston cylinder (1404) and plunger (1416). The interface between the pawl teeth (1424) and the wall teeth (1422) can be a mechanical coupling of complementary elements of the pawl teeth (1424) and the wall teeth (1422) (e.g., the elements of pawl teeth fit into the spaces between the wall teeth, and vice versa), thereby holding the locking mechanism (1420) in place within the shell housing (1408). In other aspects, the interface between the pawl teeth (1424) and the wall teeth (1422), or between the pawl teeth (1424) and other interior surface of the shell housing (1408), can be frictional, thereby holding the locking mechanism (1420) in place within the shell housing (1408). As seen in FIG. 14D, a combination of mechanical coupling (on the lower side of the illustration) and frictional interfacing (on the upper side of the illustration) can be used to implement locking of the locking mechanism (1420).

Figure 14E:
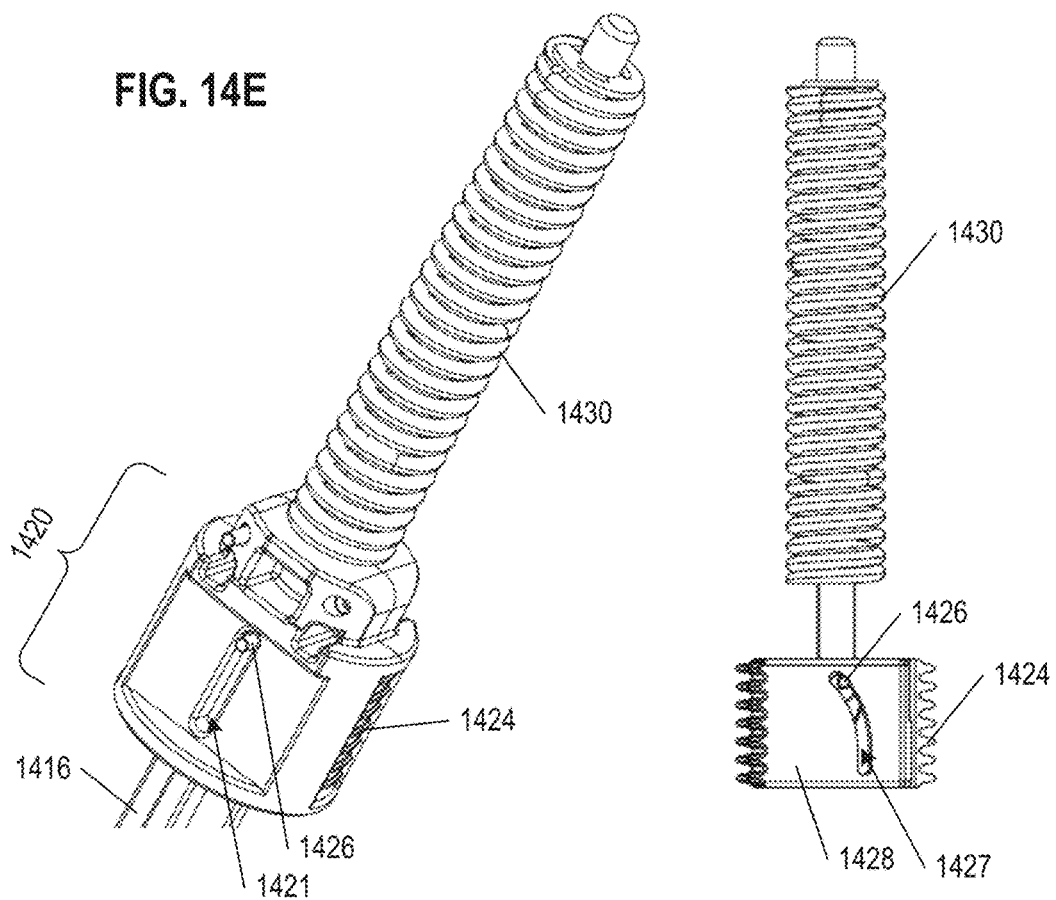
Figure 14F:
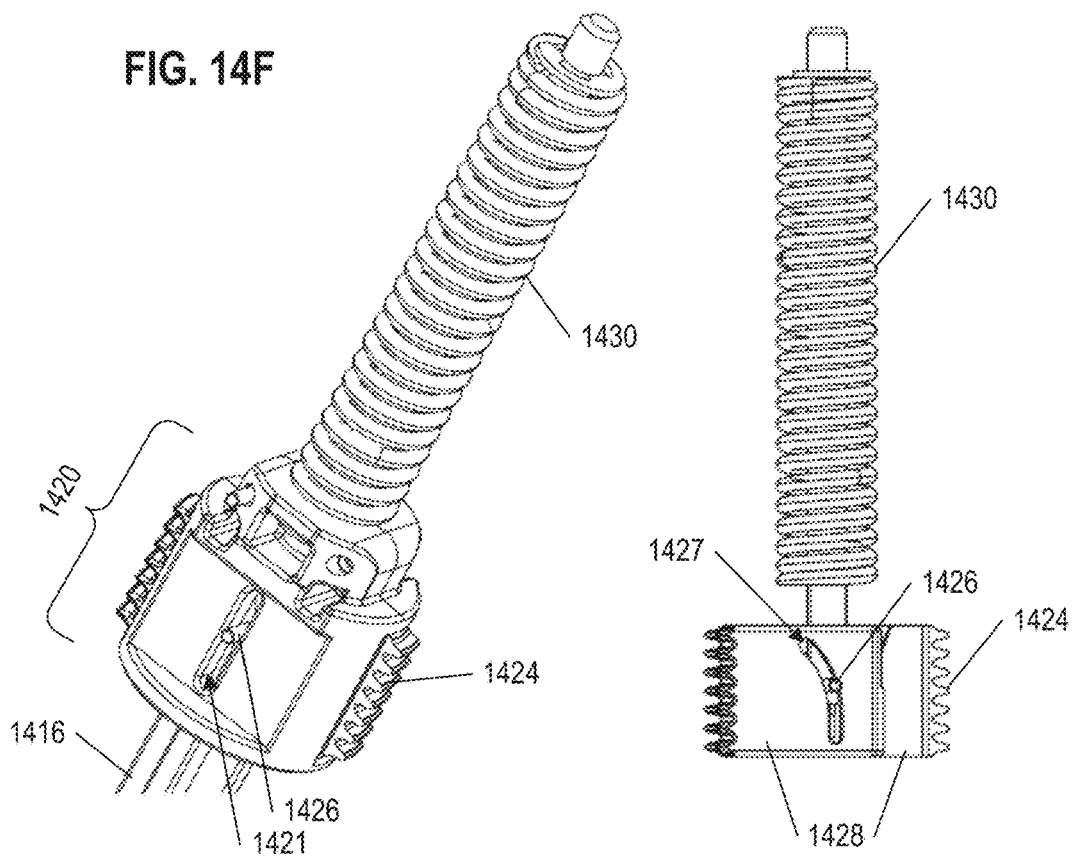

FIG. 14E is a pair of illustrations depicting detail of the locking assembly (1420) in a first, unlocked configuration. FIG. 14F is a pair of illustrations depicting details of the locking assembly (1420) in a second, locked configuration. The left-hand illustrations of FIGS. 14E and 14F show the locking mechanism (1420) housing, a pin (1426) that connects the pawls (1428) to the plunger, and a spring (1430) on the proximal end of the assembly. The right-hand illustration of FIG. 14E illustrates the positioning of the pin (1426) and the pawls (1428) in the first, unlocked configuration. The right-hand illustration of FIG. 14F illustrates the positioning of the pin (1426) and the pawls (1428) in the second, locked configuration.

As seen in FIG. 14E, the pin (1426) is in a proximal position within the locking mechanism (1420), positioned to pass through a pin window (1421) in the locking mechanism, and to pass through pawl tracks (1427) in both pawls (1428), and to mechanically fit into a recess (not shown) the plunger (1416). Accordingly, as the plunger (1416) is depressed in a distal direction, the pin (1426) also moves in a distal direction. In this configuration, with the pin (1426) in a proximal location, the pawls (1428) and the respective pawl teeth (1424) of the pawls are in a retracted or withdrawn arrangement, within the structure of the locking mechanism (1420) housing.

As seen in FIG. 14F, the pin (1426) has been moved in a distal direction (i.e. due to depression of the plunger) such that the pin (1426) is located midway down the pin window (1421) and both pawl tracks (1427). The pin (1426) is not urged or pushed in a distal direction until the spring (1430) is itself compressed with depression of the plunger (1416) far enough so that it engages with the locking mechanism (1420). Due to the shape (here a curve) of the pawl tracks (1427), the distal movement of the pin (1426) urges or pushes the pawls (1428) laterally outward, such that at least the pawl teeth (1424) of both pawls (1428) extend past the structure of the locking mechanism (1420) housing. It can be further appreciated that distal movement of the pin (1426), here caused by depression of the plunger (1416) in combination with the spring (1430) can also result in compression of the spring (1430), where the spring (1430) provides a resistive pressure against such depression.

Systems for inflation and deflation as described here can deliver fluid at a target pressure for an expandable member. In particular, the present indeflator can be configured to deliver fluid to expand an expandable member at a pressure of about twelve atmospheres (12 atm). In other configurations, the indeflator can be configured to deliver fluid to expand an expandable member at a force of from about two atmospheres to about 16 atmospheres (2 atm-16 atm), or increments or gradients of pressure in that range. The target pressure for expansion can be selected based on the anatomical structure or cavity where an expandable member will be used, such as nasal cavities, otic cavities, or the throat.

Figure 15A:
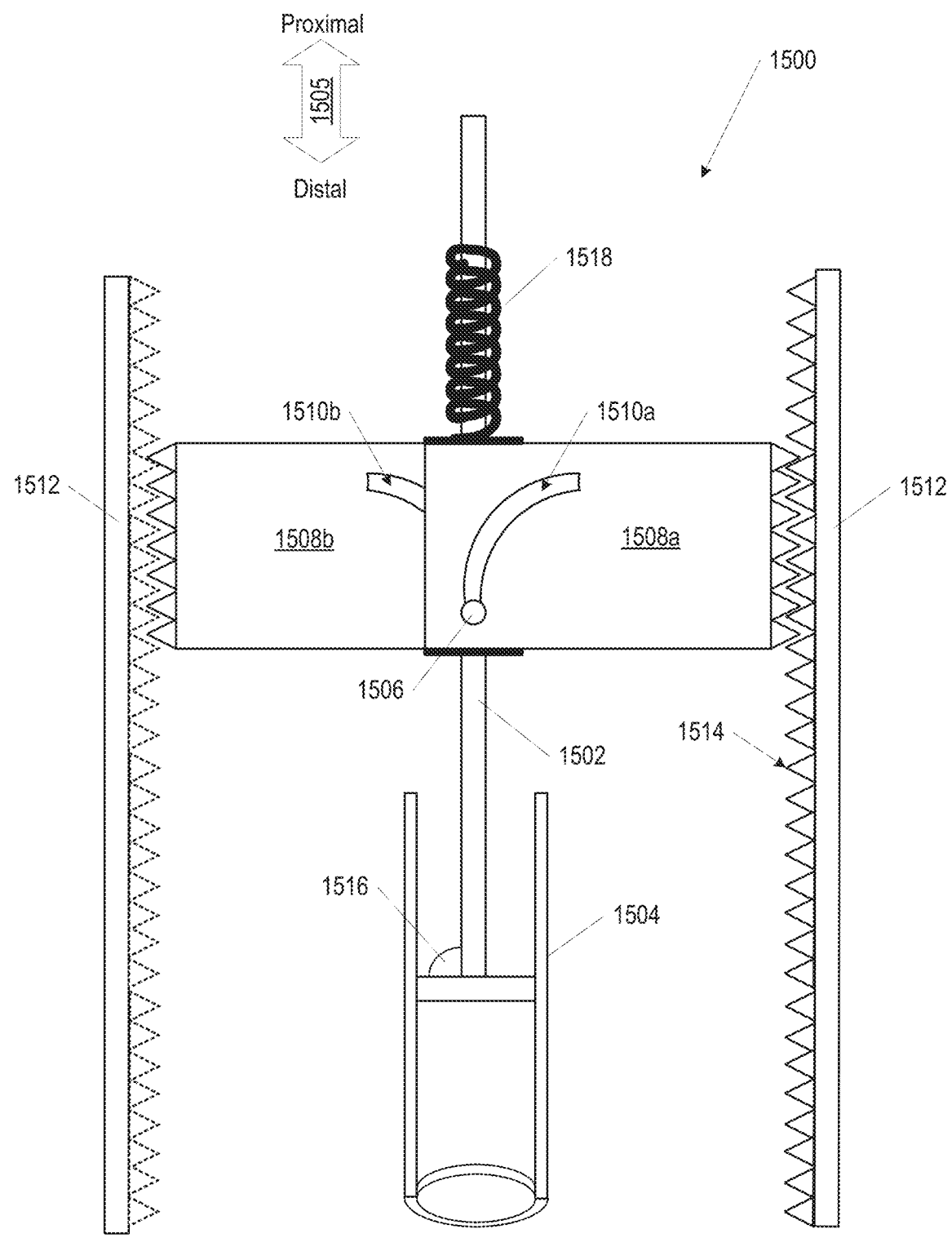
FIGS. 15A-15C are schematic representations of a plunger and locking mechanism of an exemplary inflation and deflation assembly of the present disclosure.

In some embodiments, the plunger used to inject fluid into a balloon to inflate or dilate the balloon can be configured to lock during depression of the plunger such that the volume of fluid injected does not exceed a set or predetermined pressure threshold within the balloon being inflated. FIG. 15A is a schematic illustration of an exemplary embodiment of a plunger locking structure (1500) in an exemplary embodiment of the disclosure. FIG. 15A shown the structure (1500) in a locked configuration. The plunger (1502) can be moved reversibly within the barrel of the syringe (1504), in a distal direction (in other words, forward or downward) to as to push fluid out and proximally (in other words, backward or upward) to draw fluid in, as indicated by arrow (1505). A pin (1506) is coupled to the plunger (e.g. set within a hole or indentation in the plunger), also passing through curved paths (1510a, 1510b) in pawls (1508a, 1508b), such that as the pin (1506) moves distally or proximally, the pawls (1508a, 1508b) move correspondingly due to the movement of the pin (1506) along the curved paths (1510a, 1510b). As explained in further detail below, as the plunger (1502) moves distally down the syringe barrel (1504), the pawls (1508a, 1508b) are pushed laterally outward away from a longitudinal axis (or centerline) defined by the plunger (1502). Teeth on outer edges of the pawls (1508a, 1508b) engage rails (1514) on the interior surface of the shell walls (1512) of the plunger locking structure (1500). The rails (1514) can be on one side of interior shell walls (a dashed line representation on one interior wall illustrates this option), both sides of interior shell walls (1512), or substantively around the circumference of the interior shell walls (1512) along regions where the pawls (1508a, 1508b) are arranged to physically interface with the shell walls (1512). In some aspects, the structure of the rails (1514) can be teeth complementary to the teeth on the pawls (1508a, 1508b).

When the plunger (1502) is depressed, the spring (1430) is compressed along with the plunger stroke. When the spring (143) is compressed down to a predetermined pressure, the teeth on the pawls (1508a, 1508b) will physically interface with the matching rails (1514) on the interior shell walls (1512), thereby locking the overall structure and preventing further movement of the plunger (1502) in the distal direction. Further force that is applied to the plunger (1502) is directed into the shell walls (1512) of the structure (1500) instead of driving the plunger (1502) further down the syringe barrel (1504). A spring (1518) on the plunger (1502) provides for further resistance to depression, and the spring force of that spring (1518) can be chosen specific for a target inflation pressure to be delivered by the overall structure (1500).

The plunger locking structure (1500) includes two forms of haptic feedback for operation. First, using a structure akin to a ball-point pen (not shown) depression of the plunger (1502) past a predetermined distance leads to a haptic click which indicates to the user to stop depressing the plunger. Second, a curved projection (1516), alternatively referred to as a "bump" along the shaft at the plunger (1502) located adjacent to the head of the plunger (1502) provides for an additional haptic feedback. The bump (1516) can interact with other structures within the interior of the shell walls (1512), such that the bump (1516) is sandwiched or pressed against the sides of the shell walls (1512) and provides a minor degree of resistance to movement in either or both of the distal and proximal direction. The bump (1516) can slide over the interior structure of the shell, thereby providing for a haptic feedback to indicate to a user that the plunger is at a fully drawn-back position. Further, the bump (1516) can be used as a soft-locking stopper to hold vacuum, in effect providing a resting ledge, preventing the plunger (1502) from descending into the syringe barrel (1504) without directed force from an operator.

The combined aspects of the plunger locking structure (1500) makes the indeflator volume-independent. With this structure, so long as there is a sufficient volume in the fluid chamber, i.e. the plunger (1502) is drawn back far enough within the syringe barrel (1504), the depression of the plunger (1502) will precisely provide a consistent pressure of fluid, the volume necessary to achieve the target pressure within a coupled inflation member. Specifically, as the plunger (1502) is depressed, fluid is pushed/injected into the inflation member (e.g., a balloon). The assembly is configured such that at the point where the connected inflation member reaches the target pressure due to the injection of fluid volume, the pawls (1508a, 1508b), moved by the pin (1506) riding within the curved paths (1510a, 1510b), will have been laterally extended and engage with the rails (1514) of the interior shell wall (1512). This locks the plunger locking structure (1500), and accordingly the plunger (1502) is stopped from being further depressed into the syringe barrel (1504).

The pressure of fluid injected by the indeflator can be determined and adjusted by several aspects of the overall assembly, including but not limited to: the distance moved by the plunger (1502), the strength, resistance, and compressive force of the spring (1518), the width or diameter of the shell (1512), the shape and path of the curved paths (1510a, 1510b) in their respective pawls (1508a, 1508b), the width of the pawls (1508a, 1508b), and the like. The characteristics and arrangement of these components can accordingly be selected and assembled to ensure a set volume is injected into a given balloon, thereby ensuring maximum inflation to a predetermined pressure.

Similarly with withdrawal of the plunger, the draw or vacuum exerted on the inflatable member is precise, pulling the same amount of fluid out of the inflatable member and without any substantive additional draw on the inflatable member. Advantageously, the closed system and structure of the plunger assembly provides for the ability to deflate a connected inflatable member quickly and efficiently, at a rate equivalent to the speed at which the balloon can be inflated.

Figure 15B:
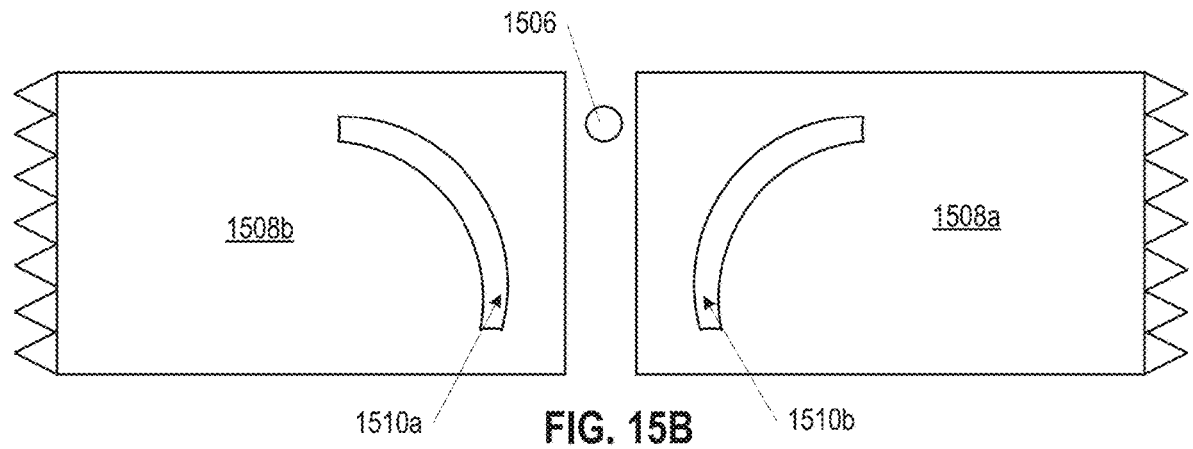
Figure 15C:
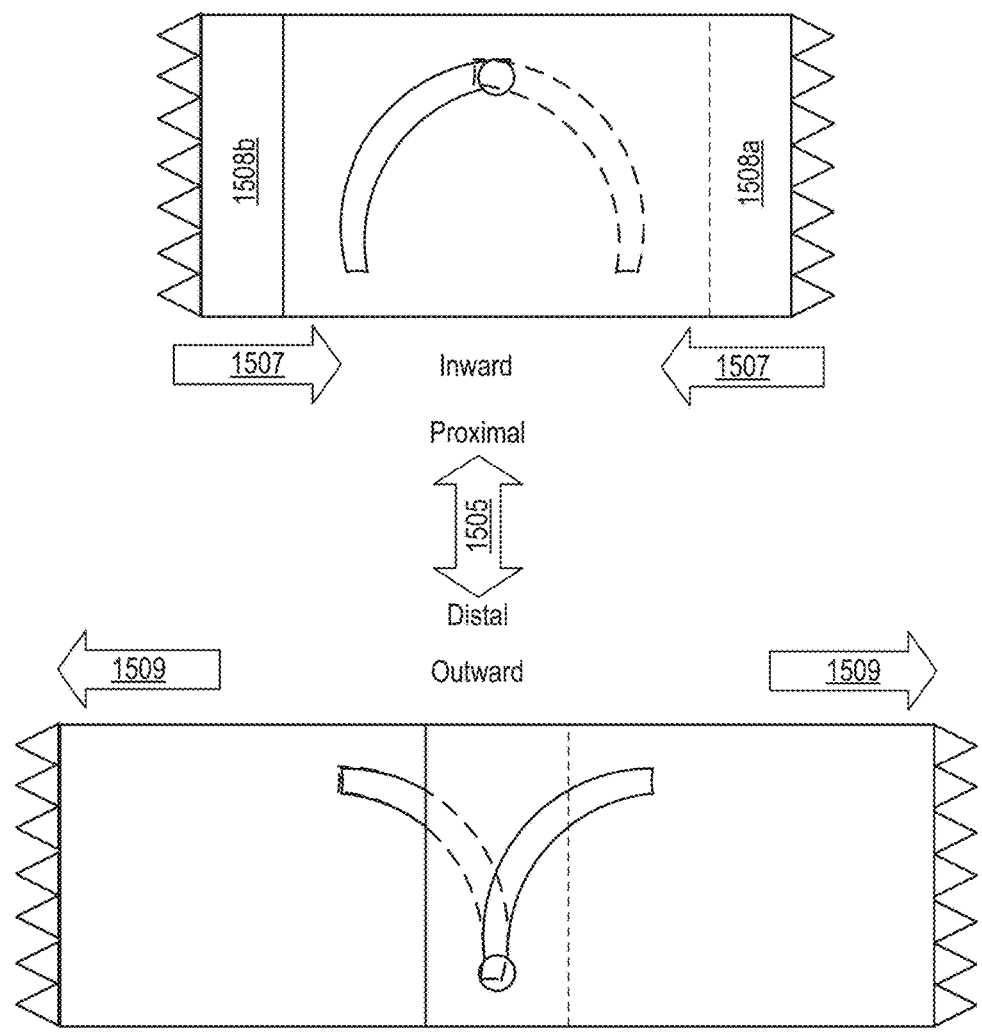

FIG. 15B is an exploded schematic illustration of the pin (1506) and pawls (1508a, 1508b) of the plunger locking structure in FIG. 15A, showing these components separately for additional clarity. FIG. 15C is a schematic illustration of the pin (1506) and pawl assembly of the plunger locking structure in FIG. 15A, capable of moving reciprocally between a first configuration and a second configuration. As seen in FIG. 15C, as the pin (1506) is pushed distally (coupled to a plunger), the pin (1506) is moved coupled within a hole in the plunger shaft in the same longitudinal direction. The first (upper) configuration shows the assembly with the pawls (1508a, 1508b) drawn inward toward each other, which within the device shell would be an unlocked configuration. As depicted, the right-hand pawl (1508a) is positioned above the left-hand pawl (1508b), with elements of the left-hand pawl (1508b) indicated with dashed-lines beneath the right-hand pawl (1508a). It should be appreciated that in other implementations, the left-hand pawl (1508b) can be oriented on top of the right-hand pawl (1508a).

The pin (1506) is positioned to pass through both curved tracks (1510a, 1510b) in each respective pawl (1508a, 1508b). As depicted, the curved tracks (1510a, 1510b) are mirrored in orientation, smooth curves, located biased toward the inner edge of their respective pawl (1508a, 1508b). It should be appreciated that in other implementations, to achieve alternative locking positions or ranges of motion, the holes forming tracks in the pawls can have shapes other than a generally smooth curve (e.g., an s-shaped curve, a stepped path, a sinusoidal curve, etc.), that the tracks can be located in other areas of the pawls, and that the tracks in each pawl do not necessarily have to mirror each other.

Continuing with FIG. 15C, as the pin (1506) is moved longitudinally in the distal direction, the pin (1506) necessarily moves down along both curved tracks (1510a, 1510b) such that the position of the pin (1506), relative to each pawl, changes from being near the middle of each pawl to the inner edge of each pawl. From another perspective, the pawls (1508a, 1508b) are moved laterally outward (indicated by the arrows 1509)) following the curved tracks (1510a, 1510b) as they are pushed by the pin (1506). As arranged, the right-hand pawl (1508a) is pushed rightward and left-hand pawl (1508b) is pushed leftward due to the movement of the pin (1506). The further down the in the distal direction the plunger (1502) moves, the further down the pin (1506) moves along the curved tracks (1510a, 1510b) toward each inner edge of the pawls (1508a, 1508b), which thereby pushes the pawls (1508a, 1508b) outward.

The second (lower) configuration shows the assembly with the pawls (1508a, 1508b) pushed laterally outward away from each other, which within the device shell would be a locked configuration. As noted above, in this configuration the pin (1506) is positioned in each respective curved track proximate to the inner edge of each pawl (1508a, 1508b). In this configuration, the movement of the pin (1506) and thus the movement of the connected plunger, has been stopped due to the laterally outward motion of the pawls (1508a, 1508b) and interface of the pawl teeth with the corresponding rails (1514) on the interior side walls (1512) of the locking structure. In some aspects, the structure can reach the second (locked) configuration with the pin (1506) at the most distal position the pin (1506) can travel along the curved tracks (1510a, 1510b), or at a position before the most distal section of the curved tracks (1510a, 1510b).

Conversely, for withdrawal of the plunger and resetting the structure to the first configuration, when the pin (1506) is moved in a proximal direction, upward along the curved tracks (1510a, 1510b), the pawls (1508a, 1508b) correspondingly move laterally inward (indicated by the arrows 1507)), again following the curved tracks (1510a, 1510b) as they are pushed by the pin (1506). In some aspects, the structure can reach the first (unlocked) configuration with the pin (1506) at the most proximal position the pin (1506) can travel along the curved tracks (1510a, 1510b), or at a position before the most proximal section of the curved tracks (1510a, 1510b).

The systems described herein may be packaged with one or more devices. A device may be preloaded into the applicator so that it is ready for use once the system is removed from the package. For example, a balloon catheter may be positioned within the applicator. Also, a guidewire may already be preloaded within the guidewire lumen of the applicator. In some variations, the system and multiple devices may be packaged together as a kit. For example, when the device is a drug-coated balloon, a plurality of drug-coated balloon catheters with varying amounts of drug within their coatings may be packaged as a kit.

Methods

Methods for accessing a target tissue site with the aforementioned systems are also described herein. Instead of using various applicators having different deflection angles when accessing different anatomical regions, the methods generally employ an applicator that is integrated (i.e., fixedly attached) to a handle of the system. The handle is capable of adjustable/selective deflection so that multiple target tissue sites may be accessed using the same applicator. For example, multiple paranasal sinuses may be accessed and treated without having to exchange the applicator when a different deflection angle is needed.

More specifically, the methods may include adjusting the deflection angle of the applicator using an adjustment knob of the system. In some variations, rotation of the adjustment knob results in axial movement of the pullwire. In turn, the axial movement of the pullwire deflects the distal end of the applicator to a desired deflection angle. Only a single pullwire is employed to generate the deflection angle. Alternatively, a deflection mechanism having a ratchet assembly may be used to retract the pullwire to thereby deflect the applicator distal end. The deflection angle may be locked and unlocked using the various types of locking mechanisms described herein.

The methods may be useful when drug delivery to multiple target tissue sites is desired using a single device, and/or when dilation or separation of target tissues is desired with a single device given that exchanging a device for each target tissue may be time consuming and costly. For example, the design may be useful when a single drug-coated balloon is used to deliver drug to multiple paranasal sinuses. In order to access the various paranasal sinuses, system angles of zero to about 120 degrees typically need to be achieved. The methods described herein are capable of maintaining a fixed handle orientation with respect to the patient while generating the appropriate angle required to rotationally align or orient an applicator tip to the intended sinus or target tissue/anatomy for treatment. Deflection of the applicator may be achieved using a single pullwire instead of the multiple pullwires typically included with commercially available steerable catheters.

Methods for deploying the same balloon catheter multiple times to the same target tissue site or to different target tissue sites are also described herein. For example, an applicator of the system may be advanced to a target tissue site of a paranasal sinus (e.g., a paranasal sinus ostium or a paranasal sinus recess), and the distal end of the applicator adjusted to the desired deflection angle by rotating an adjustment knob of the system. A balloon catheter may then be advanced from the applicator to the target tissue site and the balloon expanded to contact the target tissue site. The balloon may be expanded to an expanded configuration to deliver a drug coating to the tissue and/or for tissue dilation. Thereafter, the balloon may be deflated to a collapsed configuration and withdrawn into the applicator. If the same balloon is to be used again, either in the same or in a different ostium, the deflection angle of the applicator distal end may be adjusted/changed by rotating the adjustment knob and then the balloon advanced from the applicator and re-expanded. When the balloon is to be re-expanded in the same ostium, the deflection angle may not need to be adjusted. The balloon may then be collapsed and withdrawn again into the applicator. Readjustment of the deflection angle and deployment of the balloon catheter may be repeated any number of times.

The methods generally include maintaining the handle of the system in a fixed position while rotating an angle adjustment knob. Rotation of the adjustment knob pulls a single pullwire, which in turn deflects the distal end of an applicator depending on the amount of adjustment knob rotation. This design may be useful when drug delivery to multiple target tissue sites is desired using a single dilator. For example, the design may be useful when a single drug-coated balloon is used to deliver a drug to multiple sinuses.

In some variations, the methods for accessing a target tissue site generally include holding a sinus dilation system in one hand, the sinus dilation system including an applicator having a proximal end, a deflectable distal end, a dilator lumen, and a pullwire lumen; a handle coupled to the applicator, the handle having an elongate slot having a travel length, and a finger slide coupled to a guidewire and movable along the travel length to advance the guidewire through the applicator; a single pullwire attached to the applicator distal tip and extending proximally through the pullwire lumen; and an adjustment knob coupled to one of the applicator or the pullwire, where rotation of the adjustment knob bends the deflectable distal end of the applicator to a deflection angle that provides access to the target tissue site; advancing the applicator to a position near the target tissue site; rotating the adjustment knob to retract the pullwire proximally and deflect the distal end of the applicator to the deflection angle; and advancing a guidewire through the applicator by advancing a finger slide along at least a portion of the travel length of the elongate slot.

The methods may be useful for delivering a device over a guidewire to a target tissue site, e.g., a nasal passage or a paranasal sinus, to treat medical conditions such as post-surgical inflammation, rhinosinusitis, chronic sinusitis with or without nasal polyps, and rhinitis, including allergic rhinitis. In such variations, the target tissue site may be a paranasal sinus, a sinus ostium, a paranasal sinus recess, an inferior turbinate, a middle turbinate, a superior turbinate, a nasal cavity, the osteomeatal complex, the nasopharynx, adenoid tissue, or a combination thereof. When the device includes a drug or a drug within a coating thereof to treat a medical condition associated with the nose or a paranasal sinus, the drug may include an anti-inflammatory agent, an anti-infective agent, an antihistamine, a decongestant, a mucolytic agent, or combinations or mixtures thereof. In some variations, the anti-inflammatory agent is a corticosteroid. An exemplary corticosteroid is mometasone furoate, or a pharmaceutically acceptable salt, solvate, hydrate, ester, free base, enantiomer, racemate, polymorph, amorphous, or crystal form thereof. In some variations, the corticosteroid is fluticasone, or a pharmaceutically acceptable salt, solvate, hydrate, ester, free base, enantiomer, racemate, polymorph, amorphous, or crystal form thereof.

Figure 16:
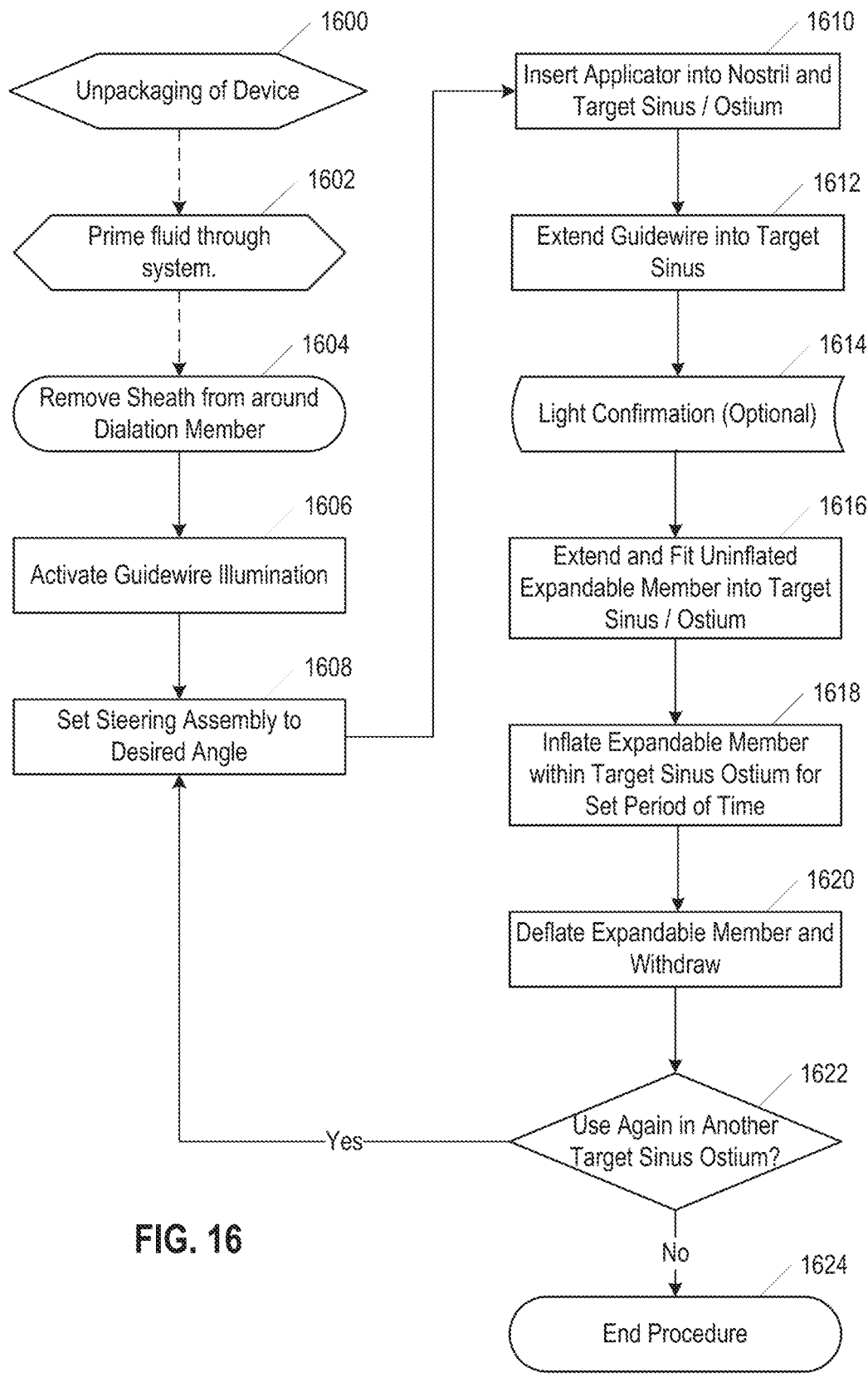
FIG. 16 depicts a flowchart illustrating an exemplary method for use of the system and delivery of treatment according to the present disclosure.

An exemplary method of delivering therapy with an expandable member as part of an applicator having a steering assembly is illustrated in the flowchart shown as FIG. 16. Initially, as a preparation step at block 1600, the device is unpackaged and assembled for operation. In further preparation, at block 1602, the fluid lines of the system are primed (e.g. with water, saline, or the like) in order to remove air bubbles from the lines. The procedure effectively begins at block 1604, where a protective sheath around a dilation member (present to protect drug coating on the dilation member from falling off or being physically displaced during storage and transport) is removed. At block 1606, in embodiments where the delivery device has an illuminating guidewire, the illuminating guidewire can be activated. For example, a lightwire can be activated by pulling a tab that physically separates batteries from providing current to the illuminating guidewire and thereby allowing the electrical circuit to complete.

At block 1608, the steering assembly can be set to a desired angle, where the adjustment of the steering assembly causes a change to the angle and/or orientation of the distal end of the applicator. The adjustment of the steering assembly can be set to predetermined setpoints corresponding to specific angular bends of the distal end. In some instances, it may not be necessary to change the angle of the distal end with the steering assembly (e.g., maintaining a straight configuration for accessing a sphenoid sinus, using the same orientation and angle for accessing both frontal sinuses subsequently, etc.). At block 1610, the applicator is guided into the nostril and proximate or adjacent to a target sinus or sinus ostium. At block 1612, the guidewire is extended out of the applicator and into the target sinus or sinus ostium. Optionally, at block 1614, the light emitted from the illuminating guidewire can be visualized through the tissue of a subject to confirm the presence of the end of the guidewire in the desired sinus. Generally, this is a broad and gross confirmation achieved simply by illumination of a substantially large region of the target sinus.

At block 1616, the expandable member, in an uninflated (low-profile) configuration, is extended into the target sinus or sinus ostium. At block 1620, the expandable member is inflated within the target sinus or sinus ostium so as to be in contact with the sinus/ostium tissue, and remains inflated for a set period of time. The expandable member, when covered with a drug coating, can transfer a percentage of the drug from the surface of the expandable member to the target sinus/ostium tissue. In some implementations, the expandable member is configured to expand to have a diameter of about 6.0 mm (±0.5 mm) when inflated. In other implementations, the expandable member can be configured to expand to have a diameter of about from 3.0 mm to about 9.0 mm when inflated. In some implementations, the expandable member can be inflated with a pressure of about 12 atmospheres. In other implementations, the expandable member can be inflated with a pressure of from about 2 atmospheres to about 12 atmospheres or increments and gradients of pressure within that range.

In some implementations, the expandable member can be inflated and held at the site of therapy for a period of time (a "hold duration") that is from 5 seconds to 120 seconds or increments of time within that range. The inflation may require a ramp-up period of a few seconds, as fluid enters the expandable member, before the expandable member is fully inflated and in functional contact with the target tissues. For uses where the expandable member is inflated multiple times, such as when being used at different sites, the hold duration may be longer for the subsequent inflations, for example to ensure a target dosage delivery of a drug located on the expandable member. In further applications, the release profile of a drug located on the expandable member may be relatively slow, and thus require a hold duration following expansion of from five to ten minutes, or longer.

At block 1620, the expandable member is deflated and withdrawn from the initial target sinus/ostium. At decision point 1622, if there is another target sinus or sinus ostium to be treated with the applicator and expandable member, the process can go back to block 1608 for the subsequent sinus or sinus ostium. With repeated inflations and delivery of therapy to two or more sinuses or sinus ostia, it is expected that the amount of drug delivered to each subsequent sinus/ostium will be progressively less, since each inflation and interfacing with tissue will deposit and remove more drug from the coating. Nevertheless, the expandable member can be prepared such that a therapeutically effective amount of drug can be delivered to up to six sinuses (e.g., both frontal sinuses, both maxillary sinuses, and both sphenoid sinuses). If there is no further sinus to deliver treatment to, the procedure can end at block 1624.

When accessing a target tissue site within the nose such as a paranasal sinus, the method may include deflecting the applicator distal end to a deflection angle ranging from zero degrees to about 120 degrees. For example, the applicator distal end may be deflected to a deflection angle of about 10 degrees, about 20 degrees, about 30 degrees, about 40 degrees, about 50 degrees, about 60 degrees, about 70 degrees, about 80 degrees, about 90 degrees, about 100 degrees, about 110 degrees, or about 120 degrees. In some variations, the deflection angle may be greater than 120 degrees. When a frontal sinus is to be accessed, it may be useful for the deflection angle to be about 70 degrees with respect to the longitudinal axis of the applicator. When a maxillary sinus is to be accessed, it may be beneficial for the deflection angle to be about 120 degrees with respect to the longitudinal axis of the applicator.

In other variations, the condition to be treated may be an otic condition selected from the group consisting of post-surgical inflammation, otitis media, Meniere's disease, Eustachian tube dysfunction, and tinnitus. In such variations, the target tissue site may be the Eustachian tube, external ear canal, or inner ear. The deflection angle useful to employ with these target tissue sites may range from zero degrees to about 120 degrees, or from about 45 degrees to about 90 degrees from the longitudinal axis of the applicator. Treatment of the Eustachian tube may also be beneficial in treating hearing loss, otalgia, and vertigo. When the device includes a drug or a drug within a coating thereof to treat an otic condition, it may be useful for the drug to include an anti-inflammatory agent, an anti-infective agent, or combinations or mixtures thereof.

In yet further variations, the condition to be treated may be a throat condition selected from the group consisting of post-surgical pain, esophageal cancer, airway stenosis, e.g., tracheal stenosis, laryngeal stenosis, or subglottic stenosis, chronic laryngitis, tonsillitis, and epiglottitis. In these variations, the target tissue site may be adenoid tissue or tonsillar tissue. When treating a throat condition, it may be useful to employ a deflection angle ranging from zero degrees to about 120 degrees, or from about 45 degrees to about 90 degrees from the longitudinal axis of the applicator. When the device includes a drug or a drug within a coating thereof to treat a throat condition, it may be useful for the drug to include a painkiller, an anti-infective agent, a chemotherapeutic agent, or combinations or mixtures thereof.

In use, the systems described here may be advanced over a guidewire to a target tissue site. In some variations, this advancement may occur under direct visualization. The direct visualization may be achieved by a device external to the system, such as an endoscope, or it may be achieved by one or more visualization devices attached to the system or disposed within one or more portions (e.g., a lumen of the applicator) of the system. Additionally or alternatively, the advancement may occur under indirect visualization, such as fluoroscopy, ultrasound, or computer image guidance.

In other variations, the systems may include an optical fiber that illuminates the position of the system with respect to the target tissue site or area to be treated (e.g., a sinus). The illumination may be visible from outside the patient. For example, the lightwire described in FIGS. 10A-10C may be used to visualize the distal end of the applicator and/or balloon catheter from outside the patient.

Once the system is properly positioned, a device, e.g., an expandable balloon, may then be deployed over the guidewire and expanded into an expanded configuration at the target tissue site, e.g., a paranasal sinus. The device may be expanded one or multiple times to transfer a drug coating, dilation of tissues, or both. In some variations, a single device may be repeatedly expanded to treat multiple and/or different paranasal sinuses. Specifically a single device may be used to treat two sinuses, three sinuses, four sinuses, five sinuses, six sinuses, seven sinuses, or eight sinuses. In one variation, a single device may be used to treat two frontal sinuses and two maxillary sinuses and/or two sphenoid sinuses.

When the devices are configured to deliver a drug to a target tissue site, the methods describe herein may further include minimizing drug loss during device deployment. Taking drug-coated sinus balloons as an example, commercially available sinus balloon dilation catheters typically lack an applicator through which the balloon is deployed. Instead, the balloon is positioned on a rigid delivery probe so that it is unprotected during advancement and withdrawal of the probe. Thus, if such balloon catheters were used to access multiple sinuses, heavy drug loss may ensue.

Thus, in some variations, deployment of the device, e.g., a balloon catheter, from an applicator having a distal tip modified to minimize drug loss. For example, the applicator distal tip may be modified to prevent scraping of drug off the device. The distal tip may be structured to be flared, conical, and/or its edges rounded to help minimize drug loss. Alternatively, the device lumen may be made from, or coated with, a lubricious material, which may help facilitate the smooth advancement and withdrawal of the device from the device lumen. Exemplary lubricous materials include without limitation, fluorinated propylene ethylene (FEP), poly (methyl methacrylate) (PMMA), polyurethane, polytetrafluoroethylene (PTFE), silicone elastomers, and combinations thereof.

EXAMPLE

The following provides one example of an applicator according to one variation, and should not be construed in any way as limiting.

Example 1: Effect of Applicator Materials on Drug Loss from a Drug-Coated Balloon A 0.089 cm (0.035 in) guidewire was delivered to the frontal sinus of a human cadaver head under endoscopic imaging. Either a commercially available 70 degree sinus applicator or a 70 degree applicator composed of Everglide blended polymers was then advanced over the guidewire to the appropriate position adjacent the frontal sinus. Next, a drug coated balloon was advanced over the guidewire and through the applicator for zero (0) (advancement and withdrawal from the applicator only, no balloon inflation), one (1), or two (2) inflation and deflation cycles. After each of these steps, the drug-coated balloon was analyzed by high performance liquid chromatography for remaining drug (mometasone furoate) content as either percent of label claim (LC) dose or remaining drug in micrograms.

The results demonstrated that approximately 30% of the drug was lost on delivery and withdrawal only (zero inflation and deflation cycles) using the commercially available applicator. The amount of drug lost with this applicator increased to approximately 50% with one (1) inflation and deflation cycle. In contrast, the amount of drug lost with the Everglide blended applicator was approximately 10% with one (1) inflation and deflation cycle, and it required at least two (2) inflation and deflation cycles to result in approximately 50% drug loss. Overall, use of the Everglide blended applicator resulted in approximately 1000 µg less drug loss with a single inflation and deflation cycle compared to a commercially available sinus applicator.

Although the foregoing invention has, for the purposes of clarity and understanding been described in some detail by way of illustration and example, it will be apparent that certain changes and modifications may be practiced, and are intended to fall within the scope of the appended claims.

The invention claimed is:

1. A system for accessing and dilating one or more target tissue sites associated with a paranasal sinus, comprising:
   a delivery device, comprising:
      an applicator, the applicator having a proximal end, a deflectable distal end, a distal tip, a device lumen, and a pullwire lumen;
      a handle, mechanically coupled to the applicator proximal end and having a first fluid connection port;
      an expandable member configured to move through the device lumen to a position at or adjacent to the deflectable distal end, and having an interior volume in fluid communication with the first fluid connection port;
      an adjustment knob rotatably coupled to, and concentrically disposed about, the applicator proximal end; and
      a pullwire having a proximal end and a distal end, extending through the pullwire lumen, where the pullwire distal end is attached to the applicator distal tip and the pullwire proximal end is coupled to the adjustment knob; and
   an inflation and deflation device, comprising:

a syringe barrel, having a second fluid connection port, the second fluid connection port configured to be in fluid communication with the first fluid connection port;

a plunger arranged to reversibly move a length within the syringe; and a locking mechanism configured to limit the length the plunger can depress within the syringe.

2. The system of claim 1, wherein the adjustment knob is configured to rotate to deflect the deflectable distal end of the applicator to a deflection angle that provides access to the target tissue site.

3. The system of claim 1, wherein the expandable member further comprises a drug coating, the drug coating including a therapeutic agent, wherein the therapeutic agent comprises mometasone furoate or pharmaceutically acceptable salts, solvates, hydrates, esters, free base, enantiomers, racemates, polymorphs, amorphous, or crystal forms thereof.

4. The system of claim 1, wherein the inflation and deflation device further comprises a housing, wherein the locking mechanism comprises a pair of pawls configured to extend outward and physically interface with the housing.

5. A system for accessing one or more target tissue sites associated with a paranasal sinus, comprising:

an applicator, the applicator having a proximal end, a deflectable distal end, a distal tip, a device lumen, and a pullwire lumen;

a handle mechanically coupled to the applicator proximal end;

an adjustment knob rotatably coupled to, and concentrically disposed about, the applicator proximal end; and a pullwire having a proximal end and a distal end, extending through the pullwire lumen, where the pullwire distal end is attached to the applicator distal tip and the pullwire proximal end is coupled to the adjustment knob.

6. The system of claim 5, wherein the adjustment knob is configured to rotate to deflect the deflectable distal end of the applicator to a deflection angle that provides access to the target tissue site.

7. The system of claim 5, wherein the handle includes a first fluid connection port and wherein the system further comprises an expandable member configured to move through the device lumen to a position at or adjacent to the deflectable distal end, and having an interior volume in fluid communication with the first fluid connection port.

8. The system of claim 5, further comprising a guidewire, wherein the handle further comprises a housing and an elongate slot disposed within the housing, the elongate slot having a travel length, and a finger slide coupled to the guidewire and movable along the travel length to advance the guidewire through the applicator.

9. The system of claim 8, wherein the guidewire further comprises two or more optical fibers arranged in a braided arrangement, and a flexible metal wire.

10. The system of claim 7, wherein the expandable member further comprises a drug coating, the drug coating including a therapeutic agent, wherein the therapeutic agent comprises mometasone furoate or pharmaceutically acceptable salts, solvates, hydrates, esters, free base, enantiomers, racemates, polymorphs, amorphous, or crystal forms thereof.

11. The system of claim 6, wherein the deflection angle ranges from about 0 degrees to about 120 degrees.

12. The system of claim 5, wherein the target tissue sites comprises a paranasal sinus ostium, a paranasal sinus cavity, a paranasal sinus passageway, or a combination thereof, and wherein the paranasal sinus is a maxillary sinus, a frontal sinus, a sphenoid sinus, or an ethmoid sinus.

13. The system of claim 5, wherein the applicator has an outside diameter ranging from about 2 mm to about 10 mm.

14. A method for accessing one or more target tissue sites associated with a paranasal sinus, comprising:

advancing a system to the target tissue site, wherein the system comprises:

an applicator comprising a proximal end, a distal end, a device lumen, a pullwire lumen, and an expandable device;

a handle fixedly attached to the applicator proximal end;

a single pullwire attached to the applicator distal tip and extending proximally through the pullwire lumen;

a guidewire; and an adjustment knob concentrically disposed about the applicator proximal end;

deflecting the distal end of the applicator to a deflection angle by retracting the single pullwire;

accessing the target tissue site with the applicator at the deflection angle;

advancing the expandable device within the device lumen and over the guidewire; and expanding the device to contact the target tissue site of the paranasal sinus.

15. The method of claim 14, wherein rotating the adjustment knob linearly translates the pullwire.

16. The method of claim 14, further comprising adjusting the deflection angle of the deflectable distal end of the applicator by rotating the adjustment knob.

17. The method of claim 14, further comprising locking the deflection angle of the applicator and subsequently unlocking the deflection angle of the applicator.

18. The method of claim 17, further comprising adjusting the deflection angle when a different target tissue site is accessed.

19. The method of claim 14, wherein the deflection angle ranges from about 0 degrees to about 120 degrees.

20. The method of claim 14, wherein the system further comprises an inflation and deflation device comprising:

a housing;

a syringe barrel, having a second fluid connection port, the second fluid connection port configured to be in fluid communication with the first fluid connection port;

a plunger arranged to reversibly move a length within the syringe; and a locking mechanism configured to limit the length the plunger can depress within the syringe.

21. The method of claim 20, wherein the locking mechanism comprises a pair of pawls configured to extend outward and physically interface with the housing.

22. The method of claim 14, wherein repeating the steps of advancing the device over the guidewire and expanding the device occurs at the same or different target tissue site of the paranasal sinus.

23. The method of claim 14, wherein contact of the expandable device to the target tissue site delivers a therapeutic agent to the target tissue site.

24. The method of claim 20, wherein the expandable device comprises an expandable balloon having a drug coating.

25. The method of claim 24, wherein the drug coating comprises mometasone furoate or pharmaceutically acceptable salts, solvates, hydrates, esters, free base, enantiomers, racemates, polymorphs, amorphous, or crystal forms thereof.

26. The method of claim 24, further comprising using a protection mechanism to minimize loss of the drug coating while accessing the target tissue site.

27. The method of claim 26, wherein the protection mechanism comprises deployment of the expandable balloon through an applicator having a flared distal end and/or deployment of the expandable balloon through a device lumen formed of or coated with a lubricious polymer.

28. The method of claim 14, wherein the target tissue site comprises a paranasal sinus ostium, a paranasal sinus cavity, a paranasal sinus passageway, or a combination thereof, and wherein the paranasal sinus is a maxillary sinus, a frontal sinus, a sphenoid sinus, or an ethmoid sinus.

* * * * *